(12) United States Patent
deLong et al.

(10) Patent No.: US 8,394,826 B2
(45) Date of Patent: Mar. 12, 2013

(54) DUAL MECHANISM INHIBITORS FOR THE TREATMENT OF DISEASE

(75) Inventors: Mitchell A. deLong, Chapel Hill, NC (US); Jill Marie Sturdivant, Chapel Hill, NC (US); Susan M. Royalty, Cary, NC (US)

(73) Assignee: Aerie Pharmaceuticals, Inc., Research Triangle Park, NC (US)

( * ) Notice: Subject to any disclaimer, the term of this patent is extended or adjusted under 35 U.S.C. 154(b) by 287 days.

(21) Appl. No.: 12/694,965

(22) Filed: Jan. 27, 2010

(65) Prior Publication Data

US 2010/0280011 A1 Nov. 4, 2010

Related U.S. Application Data

(60) Provisional application No. 61/174,672, filed on May 1, 2009.

(51) Int. Cl.
*C07D 215/38* (2006.01)
*A61K 31/04* (2006.01)
(52) U.S. Cl. .................. 514/307; 546/141; 546/148
(58) Field of Classification Search .................. 514/307; 546/141, 148
See application file for complete search history.

(56) References Cited

U.S. PATENT DOCUMENTS

| | | | |
|---|---|---|---|
| 4,911,928 A | 3/1990 | Wallach | |
| 5,508,288 A | 4/1996 | Forbes et al. | |
| 5,519,036 A | 5/1996 | Himmelsbach et al. | |
| 5,798,380 A | 8/1998 | Kaufman et al. | |
| 5,891,646 A | 4/1999 | Barak et al. | |
| 6,110,693 A | 8/2000 | Barak et al. | |
| 6,110,912 A | 8/2000 | Kaufman et al. | |
| 6,362,177 B1 | 3/2002 | Shiota et al. | |
| 6,586,425 B2 | 7/2003 | Kaufman et al. | |
| 6,787,534 B2 | 9/2004 | Haneda et al. | |
| 7,268,143 B2 | 9/2007 | Jagtap et al. | |
| 7,329,684 B2 | 2/2008 | Mjalli et al. | |
| 7,345,158 B2 | 3/2008 | Egashira et al. | |
| 7,361,678 B2 | 4/2008 | Mjalli et al. | |
| 7,374,891 B2 | 5/2008 | Shahbaz | |
| 7,378,498 B2 | 5/2008 | Worley et al. | |
| 7,470,787 B2 | 12/2008 | deLong et al. | |
| 7,671,205 B2 | 3/2010 | deLong et al. | |
| 8,034,943 B2 | 10/2011 | deLong et al. | |
| 2004/0091946 A1 | 5/2004 | Oakley et al. | |
| 2005/0032125 A1 | 2/2005 | Oakley et al. | |
| 2005/0176712 A1 | 8/2005 | Wakabayashi et al. | |
| 2005/0282805 A1 | 12/2005 | Hangeland et al. | |
| 2006/0270670 A1 | 11/2006 | Chew et al. | |
| 2007/0111983 A1 | 5/2007 | Fong | |
| 2007/0123561 A1 | 5/2007 | Lee et al. | |
| 2007/0129404 A1 | 6/2007 | Hagihara et al. | |
| 2007/0135499 A1 | 6/2007 | deLong et al. | |
| 2007/0142429 A1 | 6/2007 | deLong et al. | |
| 2007/0149473 A1 | 6/2007 | Chatterton et al. | |
| 2007/0149548 A1 | 6/2007 | Hellberg et al. | |
| 2007/0167444 A1 | 7/2007 | Kuramochi et al. | |
| 2007/0173530 A1 | 7/2007 | deLong et al. | |
| 2007/0238741 A1 | 10/2007 | Nagarathnam et al. | |
| 2008/0021026 A1 | 1/2008 | Kahraman et al. | |
| 2008/0021217 A1 | 1/2008 | Borchardt | |
| 2008/0058384 A1 | 3/2008 | Lee et al. | |
| 2008/0096238 A1 | 4/2008 | Sharif et al. | |
| 2008/0125427 A1 | 5/2008 | Sehon et al. | |
| 2008/0139595 A1 | 6/2008 | Schirok et al. | |
| 2008/0153799 A1 | 6/2008 | Laurent et al. | |
| 2008/0153813 A1 | 6/2008 | Chen et al. | |
| 2008/0161297 A1 | 7/2008 | Bosanac et al. | |
| 2008/0167340 A1 | 7/2008 | deLong et al. | |
| 2008/0194584 A1 | 8/2008 | Birault et al. | |
| 2008/0275029 A1 | 11/2008 | Berdini et al. | |
| 2009/0005321 A1 | 1/2009 | Zimmer et al. | |
| 2009/0069371 A1 | 3/2009 | deLong et al. | |
| 2009/0186917 A1* | 7/2009 | deLong et al. ................. 514/310 |
| 2010/0022585 A1* | 1/2010 | deLong et al. ................. 514/312 |
| 2010/0093790 A1 | 4/2010 | deLong et al. | |
| 2010/0105650 A1 | 4/2010 | Plettenburg et al. | |
| 2010/0137364 A1 | 6/2010 | deLong et al. | |
| 2010/0144713 A1 | 6/2010 | deLong et al. | |
| 2010/0280011 A1 | 11/2010 | deLong et al. | |
| 2011/0183965 A1 | 7/2011 | deLong et al. | |
| 2012/0135984 A1 | 5/2012 | deLong et al. | |
| 2012/0196916 A1 | 8/2012 | deLong et al. | |

FOREIGN PATENT DOCUMENTS

| | | |
|---|---|---|
| EP | 0232569 | 8/1987 |
| EP | 0389995 | 10/1990 |
| EP | 0482939 | 4/1992 |
| EP | 1550660 | 7/2005 |
| JP | 2007236388 | 9/2007 |
| JP | 2007246466 | 9/2007 |
| WO | 00/76970 | 12/2000 |
| WO | WO 01/47891 | 7/2001 |
| WO | WO 01/53268 | 7/2001 |

(Continued)

OTHER PUBLICATIONS

Hazeldine, S.T. et al., "II. Synthesis and biological evaluation of some bioisosteres and cogeners of the antitumour agent, 2(4[7-chloro-2-quinoxalinyl)oxy]phenoxy)propionic acid (XK469)," J. Med. Chem. (2002) 45:3130-3137.

(Continued)

*Primary Examiner* — D M Seaman

(74) *Attorney, Agent, or Firm* — Michael Best & Friedrich LLP

(57) ABSTRACT

Provided are compounds that are inhibitors of both rho kinase and of a monoamine transporter (MAT) act to improve the disease state or condition. Further provided are compositions comprising the compounds. Further provided are methods for treating diseases or conditions, the methods comprising administering compounds according to the invention. One such disease may be glaucoma for which, among other beneficial effects, a marked reduction in intraocular pressure (IOP) may be achieved.

33 Claims, 21 Drawing Sheets

FOREIGN PATENT DOCUMENTS

| | | |
|---|---|---|
| WO | WO 01/53274 | 7/2001 |
| WO | WO 01/56607 | 8/2001 |
| WO | WO 02/22576 | 3/2002 |
| WO | WO 02/32864 | 4/2002 |
| WO | WO 03/073999 | 9/2003 |
| WO | WO 03/080578 | 10/2003 |
| WO | 2004/029045 | 4/2004 |
| WO | WO 2005/020921 | 3/2005 |
| WO | WO 2005/035503 | 4/2005 |
| WO | WO 2005/037257 | 4/2005 |
| WO | WO 2006/041119 | 4/2006 |
| WO | 2006/051290 | 5/2006 |
| WO | WO 2006/051290 | 5/2006 |
| WO | WO 2007/008926 | 1/2007 |
| WO | WO 2007/008942 | 1/2007 |
| WO | WO 2007/060028 | 5/2007 |
| WO | 2007/065916 | 6/2007 |
| WO | WO 2007/065916 | 6/2007 |
| WO | WO 2007/076360 | 7/2007 |
| WO | WO 2007/076367 | 7/2007 |
| WO | WO 2007/100880 | 9/2007 |
| WO | WO 2007/142323 | 12/2007 |
| WO | WO 2008/011557 | 1/2008 |
| WO | WO 2008/011560 | 1/2008 |
| WO | WO 2008/016016 | 2/2008 |
| WO | WO 2008/036459 | 3/2008 |
| WO | WO 2008/036540 | 3/2008 |
| WO | WO 2008/049000 | 4/2008 |
| WO | WO 2008/049919 | 5/2008 |
| WO | WO 2008/054599 | 5/2008 |
| WO | WO 2008/077057 | 6/2008 |
| WO | WO 2008/077550 | 7/2008 |
| WO | WO 2008/077551 | 7/2008 |
| WO | WO 2008/077552 | 7/2008 |
| WO | WO 2008/077553 | 7/2008 |
| WO | WO 2008/077554 | 7/2008 |
| WO | WO 2008/077555 | 7/2008 |
| WO | WO 2008/077556 | 7/2008 |
| WO | WO 2008/079880 | 7/2008 |
| WO | WO 2008/079945 | 7/2008 |
| WO | WO 2008/086269 | 7/2008 |
| WO | WO 2009/091898 | 7/2009 |
| WO | WO 2010/011853 | 1/2010 |
| WO | 2010/126626 | 11/2010 |
| WO | 2010/127329 | 11/2010 |
| WO | 2010/127330 | 11/2010 |
| WO | WO 2010/126626 | 11/2010 |
| WO | WO 2010/127329 | 11/2010 |
| WO | WO 2010/127330 | 11/2010 |

OTHER PUBLICATIONS

Parang, K. et al., "Design strategies for protein kinase inhibitors," Curr. Opin. In Drug Disc. & Dev. (2004) 7 (5):617-629.

International Search Report and Written Opinion for Application No. PCT/US2007/078343 dated Apr. 30, 2008 (12 pages).

European Patent Office Action for Application No. 09702189.3 dated Feb. 1, 2011 (5 pages).

European Patent Office Action for Application No. 09702189.3 dated Dec. 28, 2011 (5 pages).

Euoprean Patent Office Action for Application No. 09790775.2 dated Oct. 24, 2011 (5 pages).

United States Patent Office Final Rejection for U.S. Appl. No. 13/230,105 dated Jul. 9, 2012 (11 pages).

United States Patent Office Notice of Allowance for U.S. Appl. No. 13/017,708 dated Sep. 17, 2012 (8 pages).

Banker, G.S. et al., Modern Pharmaceutics, Marcel Dekker, Inc., New York, (1979) Chapters 9 and 10.

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Capdeville, R. et al., "Glivec (STI571, IMATINIB), A Rationally Developed, Targeted Anticancer Drug", Nature Reviews Drug Discovery (2002) 1:493-502.

Chen, P. et al., "Identification of novel and potent isoquinoline aminooxazole-based IMPDH inhibitors," Bioorg. Med. Chem. Lett. (2003) 13(7):1345-1348.

Dancey, J. et al., "Issues and Progress with Protein Kinase Inhibitors for Cancer Treatment", Nature Reviews Drug Discovery (2003) 2:296-313.

Dorwald, F.Z., Side Reactions in Organic Synthesis. A Guide to Successful Synthesis Design, Wiley-VCH, Weinheim (2005) IX of Preface and 1-15.

Hackam, A.S. et al., "The Wnt Signaling Pathway in Retinal Degenerations", IUBMB Life (2005) 57(6):381-388.

Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.

Inouye, Y. et al., "The Absolute Configurations of TRANS-1,2-Cyclopropanedicarboxylic Acid and TRANS-2-Phenylcyclopropanecarboxylic Acid", Int'l. J. Org. Chem. (1964) 20(5):1695-1699.

Liljebris, C. et al., "Derivatives of 17-Phenyl-18,19,20-trinorprostaglandin F2α Isopropyl Ester: Potential Antiglaucoma Agents," J. Med. Chem. (1995) 38(2):289-304.

McCutcheon's, "Emulsifiers & Detergents", North American Edition (1994) vol. 1:236-239.

Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1(1-1):21-30.

Penmetsa, K.V. et al., "Development of Reversed-Phase Chiral HPLC Methods Using Mass Spectrometry Compatible Mobile Phases", J. Liquid Chroma. Rel. Tech. (2000) 23(6-10):831-839.

Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.

Shankar, G. et al., "Protein-kinase-specific inhibitors block Langerhans' cell migration by inhibiting interleukin-1α release", Immunology (1999) 96:230-235.

Stirewalt, D.L. et al., "The Role of FLT3 in Haematopoietic Malignancies", Nature Reviews Cancer (2003) 3:650-665.

Webster, F.X. et al., "Following the Course of Resolution of Carboxylic Acids by 13C NMR Spectrometry of Amine Salts" J. Org. Chem. (1982) 47(26):5225-5226.

Westaway, S.M. et al., "N-tetrahydroquinolinyl, N-quinolinyl and N-isoquinolinyl biaryl carboxamides as antagonists of TRPV1," Biorg. Med. Chem. Lett. (2006) 16:4533-4536.

Westra, J. et al., "p38 Mitogen-Activated Protein Kinase (MAPK) in Rheumatoid Arthritis", Mini-Reviews in Medicinal Chemistry (2006) 6(8):867-874.

United States Office Action for U.S. Appl. No. 11/485,182 dated Apr. 16, 2009 (13 pages).

United States Office Action for U.S. Appl. No. 12/274,887 dated Jun. 16, 2009 (11 pages).

United States Patent Office Action for U.S. Appl. No. 11/621,887 dated May 18, 2010 (8 pages).

United States Office Action for U.S. Appl. No. 11/621,892 dated Aug. 8, 2008 (9 pages).

United States Office Action for U.S. Appl. No. 11/621,892 dated Mar. 9, 2009 (6 pages).

Partial International Search for Application No. PCT/US2009/031117 dated Apr. 16, 2009 (4 pages).

International Search Report and Written Opinion for Application No. PCT/US2006/026976 dated Feb. 15, 2007 (14 pages).

International Search Report for Application No. PCT/US2006/026947 dated Nov. 17, 2006 (4 pages).

International Preliminary Examination Report for Application No. PCT/US2006/026947 dated Jan. 24, 2008 (10 pages).

International Search Report for Application No. PCT/US08/50374 dated Oct. 28, 2008 (7 pages).

International Preliminary Report on Patentability for Application No. PCT/US08/50374 dated Jul. 14, 2009 (11 pages).

International Search Report and Written Opinion for Application No. PCT/US2009/031117 dated Sep. 24, 2009 (13 pages).

Invitation to Pay Additional Fees and Partial International Search Report for International Application No. PCT/US2009/051569 dated Oct. 15, 2009 (4 pages).

International Search Report and Written Opinion for Application No. PCT/US2009/051569 dated May 20, 2010 (11 pages).

International Search Report and Written Opinion for Application No. PCT/US2010/33316 dated Jul. 14, 2010 (10 pages).

Bird, G.J. et al., "N-methyl as a bioisostere for the oxygen link between the aromatic rings of aryloxyphenoxypropionate herbicides," Bioorg. Med. Chem. Lett. (1997) 7:1489-1492.

Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18): 4029-37.

Calmes et al., Eur. J. Org. Chem. 2000, 2459-2466.

Cheung, S.T. et al. Can. J. Chem. 1977, 55,906-910.

Dowton et al., "Influence of Liposomal Composition on Topical Delivery of Encapsulated Cyclosporin A", S.T.P. Pharma Sciences, vol. 3, pp. 404-407 (1993).

Foye, Foye's Principles of Medicinal Chemistry, 5th Edition (2002) Lippencott, Williams, Wilkins, p. 59-63.

G.E. Torres, R.R. Gainetdinov and M.G. Caron (2003). "Plasma membrane monoamine transporters: structure, regulation and function". Nat. Rev. Neurosci. 4 (1): 13-25.

Hazeldine, S.T. et al., "II. Synthesis and biological evaluation of some bioisosteres and cogeners of the antitumour agent, 2 {4[7-chloro-2-quinoxalinyl)oxy]phenoxy}propionic acid (XK469)," J. Med. Chem. (2002) 45:3130-3137.

He R, Kurome T, Giberson KM, Johnson KM, Kozikowski AP (2005). "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chem. 48 (25): 7970-9.

Hu, E. et al., "Rho kinase as potential therapeutic target for cardiovascular diseases: opportunities and challenges," Exp. Opin. Ther. Targets (2005) 9:715-736.

Karaman, M.W. et al., "A quantitative analysis of kinase inhibitor selectivity," Nature Biotech. (2008) 26(1):127-132.

Loge, C; Siomboing, X et al. J, of Enzy Inhib & Med Chem, 2003,18,127-128.

Matsui, T. et al., "Novel 5-HT3 antagonists. Isoquinolinones and 3-aryl-2-pyridones," J. Med. Chem. (1992) 35:3307-3319.

Parang, K. et al., "Design strategies for protein kinase inhibitors," Curr. Opin. in Drug Disc. & Dev. (2004) 7(5):617-629.

Van Muijlwijk-Koezen et al., "A novel class of adenosine A3 receptor-ligands. 2. Structure affinity profile of a series of isoquinoline and quinazoline compounds," J. Med. Chem. (1998) 41:3994-4000.

Wallach and Philippot, "New Type of Lipid Vesicle: Novasome®", Liposome Technology, vol. 1, pp. 141-156 (1993).

West, A.R., "Solid state chemistry and its applications," Wiley, New York (1988) pp. 358 and 365.

United States Patent Office Action for U.S. Appl. No. 12/639,670 dated Jan. 31, 2011 (8 pages).

United States Patent Office Action for U.S. Appl. No. 12/639,670 dated Jul. 27, 2011 (5 pages).

United States Patent Office Action for U.S. Appl. No. 11/621,887 dated Oct. 29, 2010 (14 pages).

United States Patent Office Action for U.S. Appl. No. 13/017,708 dated Apr. 3, 2012 (11 pages).

United States Patent Office Action for U.S. Appl. No. 12/701,963 dated May 10, 2011 (3 pages).

United States Patent Office Action for U.S. Appl. No. 13/230,105 dated Mar. 5, 2012 (8 pages).

United States Patent Office Action for U.S. Appl. No. 12/009,326 dated Feb. 3, 2011 (8 pages).

United States Patent Office Notice of Allowance for U.S. Appl. No. 12/009,326 dated Jan. 6, 2012 (5 pages).

United States Patent Office Action for U.S. Appl. No. 12/704,822 dated Apr. 30, 2012 (34 pages).

United States Patent Office Advisory Action for U.S. Appl. No. 11/856,740 dated Feb. 10, 2011 (3 pages).

United States Patent Office Action for U.S. Appl. No. 11/856,740 dated Dec. 6, 2010 (12 pages).

United States Patent Office Action for U.S. Appl. No. 11/856,740 dated Jun. 29, 2010 (10 pages).

United States Patent Office Action for U.S. Appl. No. 12/180,259 dated Jul. 5, 2011 (11 pages).

United States Patent Office Notice of Allowance for U.S. Appl. No. 12/180,259 dated Dec. 19, 2011 (6 pages).

United States Patent Office Action for U.S. Appl. No. 12/694,965 dated May 17, 2012 (13 pages).

International Preliminary Report on Patentability for Application No. PCT/US08/50374 dated Jul. 14, 2009 (12 pages).

International Search Report and Written Opinion for Application No. PCT/US2010/33317 dated Aug. 17, 2010 (10 pages).

International Search Report and Written Opinion for Application No. PCT/US2010/022246 dated Nov. 10, 2010 (7 pages).

International Search Report and Written Opinion for Application No. PCT/US2007/078343 dated Apr. 3, 2008 (12 pages).

United States Patent Office Notice of Allowance for U.S. Appl. No. 13/017,708 dated Oct. 23, 2012 (7 pages).

United States Patent Office Notice of Allowance for U.S. Appl. No. 13/442,263 dated Dec. 19, 2012 (13 pages).

Tamura, M., et al., "Development of specific Rho-kinase inhibitors and their clinical application," Biochimica et Biophysica Acta, 2005, vol. 1754, pp. 245-252.

United States Patent Office Notice of Allowability for U.S. Appl. No. 13/017,708 dated Dec. 12, 2012 (5 pages).

Ito, N. et al., "A medium-term rat liver bioassay for rapid in vivo detection of carcinogenic potential of chemicals," Cancer Science, Jan. 2003, vol. 94, No. 1, pp. 3-8.

STN Registry Database entry for CAS RN 309903-43-6, Published in database Dec. 20, 2000.

United States Patent Office Final Rejection for U.S. Appl. No. 12/704,822 dated Jan. 16, 2013 (16 pages).

* cited by examiner

US 8,394,826 B2

DUAL MECHANISM INHIBITORS FOR THE TREATMENT OF DISEASE

CROSS-REFERENCE TO RELATED APPLICATIONS

This application claims priority to U.S. Provisional Application No. 61/174,672, filed May 1, 2009, and incorporated herein by reference in its entirety.

FIELD OF THE INVENTION

The present invention relates to substituted isoquinoline amide compounds and substituted benzamide compounds that affect the function of kinases and the function of transporters in a cell and that are useful as therapeutic agents or in conjunction with therapeutic agents. In particular, these compounds are useful in the treatment of diseases and disorders of the eye, such as glaucoma, of the respiratory system, of the cardiovascular system, and for diseases characterized by abnormal growth, such as cancers.

BACKGROUND

A wide variety of hormones, neurotransmitters, and other biologically active substances control, regulate, or adjust the functions of the body via interaction with specific cellular receptors. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, adrenergic receptors, opioid receptors, cannabinoid receptors, and prostaglandin receptors. The biological effects of activating these receptors are not direct but are mediated by a host of intracellular proteins. The importance of these secondary proteins has only recently been recognized and investigated as intervention points in disease states. One of the most important classes of downstream effectors is the "kinase" class.

Various kinases play important roles in the regulation of many physiological functions. For example, kinases have been implicated in numerous disease states including, but not limited to, cardiac disorders such as angina pectoris, essential hypertension, myocardial infarction, supraventricular and ventricular arrhythmias, congestive heart failure, and atherosclerosis, respiratory disorders such as asthma, chronic bronchitis, bronchospasm, emphysema, airway obstruction, rhinitis, and seasonal allergies, inflammation, rheumatoid arthritis, renal failure, and diabetes. Other conditions include chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, pain, obesity, bulimia nervosa, depression, obsessive-compulsive disorder, organ malformations (e.g., cardiac malformations), neurodegenerative diseases such as Parkinson's Disease and Alzheimer's Disease, multiple sclerosis, Epstein-Barr infection, and cancer (*Nature Reviews Drug Discovery* 2002, 1: 493-502). In other disease states, the role of kinases is only now becoming clear.

The success of the tyrosine-kinase inhibitor ST1571 (Gleevec) in the treatment of chronic myelogenous leukemia (*Nature Reviews Drug Discovery* 2003, 2: 296-313) has spurred considerable efforts to develop other kinase inhibitors for the treatment of a wide range of other cancers (*Nature Reviews Cancer* 2003, 3: 650-665). Seven additional kinase inhibitor drugs have since been brought to market, establishing kinase inhibitors as an important new drug class. Currently more than 100 protein kinase inhibitors are in clinical development (*Kinase Inhibitor Drugs* 2009, Wiley Press).

In view of the role that kinases have in many disease states, there is an urgent and continuing need for small molecule ligands that inhibit or modulate the activity of kinases. Without wishing to be bound by theory, it is thought that modulation of the activity of kinases, including rho kinase (ROCK), by the compounds of the present invention is, in part, responsible for their beneficial effects.

An additional area of fruitful research in medicine is the study of monoamine transporters and the benefits of inhibition thereof. Monoamine transporters (MAT) are structures in cell membranes that transport monoamine-containing neurotransmitters into or out of cells. There are several distinct monoamine transporters, or MATs: the dopamine transporter (DAT), the norepinephrine transporter (NET), and the serotonin transporter (SERT). DAT, NET, and SERT are structurally-related, and each contains a structure of 12 trans-membrane helices. Modern antidepressants are thought to work by enhancing serotonergic, noradrenergic, or dopaminergic neurotransmission by binding to their respective transporter, and thereby inhibiting neurotransmitter reuptake and effectively raising the concentration of the neurotransmitter in synapses. Examples of drugs that are thought to operate by this mechanism include fluoxetine, a selective SERT inhibitor; reboxetine, a norepinephrine (NET) inhibitor; and bupropion, which inhibits both the NET and DAT (He, R. et al. *J. Med. Chem.* 2005, 48: 7970-9; Blough, B. E. et al. *J. Med. Chem.* 2002, 45: 4029-37; Blough, B. E., et al. *J. Med. Chem.* 1996, 39: 4027-35; Torres, G. E., et al. *Nat. Rev. Neurosci.* 2003, 4: 13-25).

Glaucoma causes deterioration of the eye's optic nerve, the nerve bundles that carry images from the ganglion cells of the eye to the brain. Increased IOP is a hallmark of the most common forms of glaucoma, and this increased intraocular pressure likely damages the optic nerve and ganglion cells through multiple mechanisms. Current glaucoma medications act by reducing intraocular pressure, either by slowing the flow of aqueous humor into the eye or by improving the drainage of this fluid from the eye. Inhibitors of rho kinase have been shown to reduce IOP in rabbits and monkeys by increasing aqueous humor drainage through the trabecular meshwork (Tian and Kaufman, *Arch Ophthalmol* 2004, 122: 1171-1178; Tokushige et al., *IOVS* 2007, 48(7): 3216-3222). Several lines of experimental evidence indicate that modulating the activity of rho kinase within the aqueous humor outflow pathway could be beneficial for the treatment of patients with glaucoma (Honjo et al., IOVS 2001; 42: 137-144; Waki et al., Curr Eye Res 2001; 22: 470-474; Rao et al., IOVS 2001; 42: 1029-1037). Considerable evidence suggests that the sympathetic nervous system plays a significant but complex role in the regulation of IOP (Nathanson, Proc. Natl. Acad. Sci. USA 1980; 77(12):7420-7424). Sympathetic nerve fibers innervate the ciliary process and trabecular meshwork (Ehinger, Acta Univ. Lund Sect 2 1964; 20:3-23; Sears, 1975, Handbook of Physiology, Endocrinology VI. Eds Astwood E & Greep R: 553-590) and both sympathetic stimulation and locally applied β-adrenergic agonists such as epinephrine decrease IOP (Sears, 1975, ibid; Dayson et al., J. Physiol. (London) 1951; 113:389-397).

SUMMARY OF THE INVENTION

In one aspect, the may invention provide compounds according to Formulas I, II, III, IV, V, or VI, as describe below.

In other aspects, the invention may provide pharmaceutical compositions, comprising a compound according to Formula I, II, III, IV, V, or VI as described below, and a carrier.

In further aspects, the invention may provide methods of treating a disease in a subject, the method comprising administering to a subject an effective amount of a compound according to Formula I, II, III, IV, V, or VI as described below. The disease may be selected from the group consisting of eye disease including glaucoma and retinal diseases such as Wet AMD Dry AMD (inflammation) and DME, bone disorder including osteoporosis, vascular disease including cerebral vasospasm, coronary vasospasm, hypertension, pulmonary hypertension, sudden death syndrome, angina, myocardial infarction, restenosis, stroke, hypertensive vascular disease, heart failure, cardiac allograft vasculopathy, vein graft disease, pulmonary disease including chronic obstructive pulmonary disease (COPD) and asthma, neurological disorder including spinal cord injury, Alzheimer's disease, multiple sclerosis, depression, attention deficit-hyperactivity disorder and neuropathic pain, neovascular disorders and cancer, obesity, and erectile dysfunction.

In further aspects, the invention may provide methods of modulating kinase activity, the methods comprising contacting a cell with a compound according to Formula I, II, III, IV, V, or VI as described below, in an amount effective to modulate kinase activity.

In further aspects, the invention may provide methods of reducing intraocular pressure, the methods comprising contacting a cell with a compound according to Formula I, II, III, IV, V or VI as described below, in an amount effective to reduce intraocular pressure.

DETAILED DESCRIPTION

Figure 1:
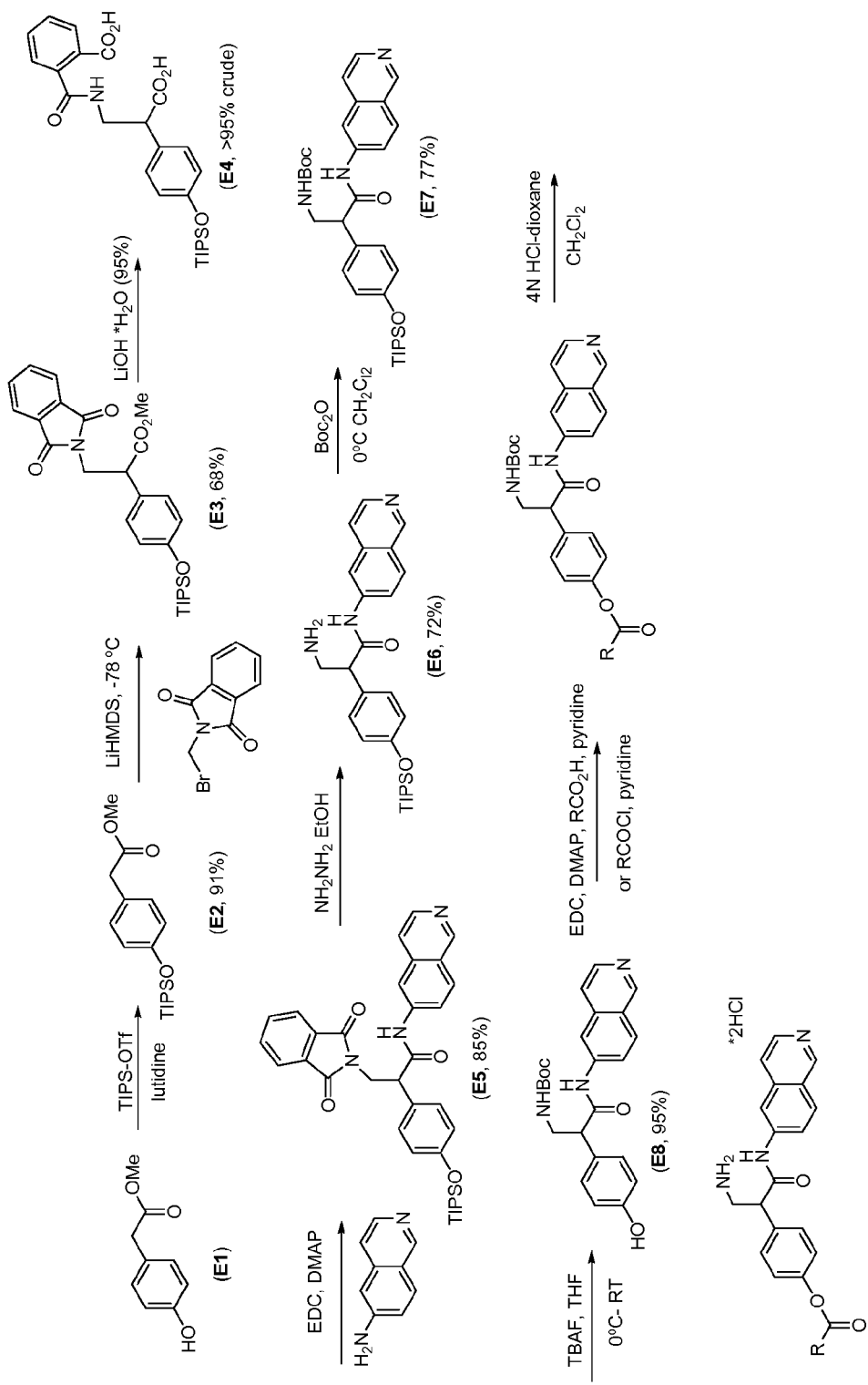
FIG. 1 is a scheme for the synthesis of compounds, including E1-E8.

Publications and patents are referred to throughout this disclosure. All U.S. patents cited herein are hereby incorporated by reference. All percentages, ratios, and proportions used herein are percent by weight unless otherwise specified.

Amino isoquinolyl amides and amino benzamidyl amides are provided. In some aspects, the compositions and methods for treating diseases and conditions wherein compounds that may be inhibitors of both rho kinase and of a monoamine transporter (MAT) act to improve the disease state or condition. One such disease may be glaucoma for which, among other beneficial effects, a marked reduction in intraocular pressure (IOP) may be achieved.

DEFINITIONS

"Alkyl" refers to a saturated aliphatic hydrocarbon moiety including straight chain and branched chain groups. "Alkyl" may be exemplified by groups such as methyl, ethyl, n-propyl, isopropyl, n-butyl and the like. Alkyl groups may be substituted or unsubstituted. Substituents may also be themselves substituted.

When substituted, the substituent group is preferably but not limited to $C_1$-$C_4$ alkyl, aryl, carbocyclyl, heterocarbocyclyl, heteroaryl, amino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. Substituents may also be themselves substituted. When substituted, the substituent group is preferably alkyl, aryl, carbocyclyl, heterocarbocyclyl, heteroaryl, halogen or alkoxy. Substituents may also be themselves substituted. Substituents may be placed on the alkene itself and also on the adjacent member atoms or the alkynyl moiety. "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. When substituted, the substituent group is preferably alkyl, aryl, carbocyclyl, heterocarbocyclyl, heteroaryl, amino, cyano, halogen, alkoxyl or hydroxyl. Substituents may also be themselves substituted. When substituted, substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the moiety —C(O)R wherein R is alkyl, alkenyl, alkynyl, aryl, heteroaryl, carbocyclic, heterocarbocyclic, $C_1$-$C_4$ alkyl aryl, or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the moiety —O—R wherein R is acyl, alkyl alkenyl, alkyl alkynyl, aryl, carbocyclic, heterocarbocyclic, heteroaryl, $C_1$-$C_4$ alkyl aryl, or $C_1$-$C_4$ alkyl heteroaryl.

"Amino" refers to the moiety —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl, or $C_1$-$C_4$ alkyl heteroaryl. The two R' groups may themselves be linked to form a ring. The R' groups may themselves be further substituted, in which case the group also known as guanidinyl is specifically contemplated under the term "amino".

"Aryl" or "aromatic ring" refers to an aromatic carbocyclic moiety. "Aryl" may be exemplified by phenyl. The aryl group may be substituted or unsubstituted. Substituents may also be themselves substituted. When substituted, the substituent group is preferably but not limited to alkoxyl, heteroaryl, acyl, carboxyl, carbonylamino, nitro, amino, cyano, halogen, or hydroxyl.

"Carboxyl" refers to the group —C(=O)O—R wherein R is chosen from hydrogen, alkyl, aryl, cycloalkyl, heterocycloalkyl, heteroaryl, $C_1$-$C_4$ alkyl aryl, or $C_1$-$C_4$ alkyl heteroaryl.

"Carbonyl" refers to the group —C(O)R wherein each R is, independently, hydrogen, alkyl, aryl, cycloalkyl, heterocycloalkyl, heteroaryl, $C_1$-$C_4$ alkyl aryl, or $C_1$-$C_4$ alkyl heteroaryl.

"Carbonylamino" refers to the group —C(O)NR'R' wherein each R' is, independently, hydrogen, alkyl, aryl, cycloalkyl, heterocycloalkyl, heteroaryl, $C_1$-$C_4$ alkyl aryl, or $C_1$-$C_4$ alkyl heteroaryl. The two R' groups may themselves be linked to form a ring. Carbonylamino is also known as an amide linkage.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl and phenethyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. Substituents may also be themselves substituted. Preferred carbocyclic groups include cyclopropyl, cyclobutyl, cyclopentyl, cyclohexyl, cyclohexenyl, and cycloheptyl. More preferred carbocyclic groups include cyclopentyl and cyclohexyl. The most preferred carbocyclic group is cyclohexyl. Carbocyclic groups are not aromatic.

"Halogen" refers to fluoro, chloro, bromo, or iodo moieties. Preferably, the halogen is fluoro, chloro, or bromo.

"Heteroaryl" or "heteroaromatic ring" refers to a monocyclic or bicyclic aromatic carbocyclic radical having one or more heteroatoms in the carbocyclic ring. Heteroaryl may be substituted or unsubstituted. When substituted, the substituents may themselves be substituted. Non-limiting examples of substituents may include aryl, $C_1$-$C_4$ alkylaryl, amino, halogen, hydroxy, cyano, nitro, carboxyl, carbonylamino, or $C_1$-$C_4$ alkyl. Preferred heteroaromatic groups include tetrazoyl, triazolyl, thienyl, thiazolyl, purinyl, pyrimidyl, pyridyl, and furanyl. More preferred heteroaromatic groups include benzothiofuranyl, thienyl, furanyl, tetrazoyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxyl is alcohol.

"Linker" means a linear chain of n member atoms where n is an integer of from about 1 to about 4 member atoms.

"Member atom" means a carbon, nitrogen, oxygen, or sulfur atom. Member atoms may be substituted up to their normal valence. If substitution is not specified the substituents required for valency are hydrogen.

"Ring" means a collection of member atoms that are cyclic. Rings may be carbocyclic, aromatic, heterocyclic, or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Sulfonyl" refers to the —S(O)$_2$R' group wherein R' is alkoxy, alkyl, aryl, carbocyclic, heterocarbocyclic, heteroaryl, $C_1$-$C_4$ alkyl aryl, or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl, or $C_1$-$C_4$ alkyl heteroaryl.

"Pharmaceutically acceptable carrier" means a carrier that is useful for the preparation of a pharmaceutical composition that is generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal, and oral administration. "Pharmaceutically acceptable carrier" also includes agents for preparation of aqueous dispersions and sterile powders for injection or dispersions.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

"Effective amount" as used herein refers to a dosage of the compounds or compositions effective for influencing, reducing, or inhibiting the activity of or preventing activation of a kinase or a transporter protein. This term as used herein may also refer to an amount effective at bringing about a desired in vivo effect in an animal, preferably, a human, such as reduction in intraocular pressure.

"Administering" as used herein refers to administration of the compounds as needed to achieve the desired effect.

"Eye disease" as used herein includes, but is not limited to, glaucoma, allergy, cancers of the eye, neurodegenerative diseases of the eye, and dry eye.

The term "disease or condition associated with kinase activity" is used to mean a disease or condition treatable, in whole or in part, by inhibition of one or more kinases. The diseases or conditions may include, but are not limited to, eye disease including glaucoma and retinal diseases such as Wet AMD Dry AMD (inflammation) and DME, ocular hypertension, bone disorder including osteoporosis, vascular disease including cerebral vasospasm, cardiovascular diseases, coronary vasospasm, hypertension, pulmonary hypertension, sudden death syndrome, angina, myocardial infarction, restenosis, stroke, hypertensive vascular disease, heart failure, cardiac allograft vasculopathy, vein graft disease, pulmonary disease including chronic obstructive pulmonary disease (COPD) and asthma, neurological disorder including spinal cord injury, Alzheimer's disease, multiple sclerosis, depression, attention deficit-hyperactivity disorder and neuropathic pain, neovascular disorders and cancer, obesity, and erectile dysfunction.

The term "controlling the disease or condition" is used to mean changing the activity of one or more kinases to affect the disease or condition.

The term "contacting a cell" is used to mean contacting a cell in vitro or in vivo (i.e. in a subject, such as a mammal, including humans, cats, and dogs).

Compounds

In a first aspect of the invention, provided are isoquinoline amide compounds. Compounds according to the inventions include those according to Formula I:

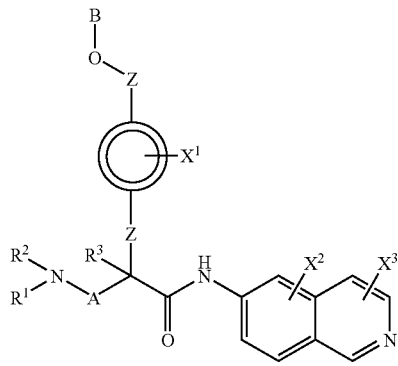

(I)

wherein $R^1$, $R^2$, and $R^3$ are independently hydrogen, $C_1$-$C_4$ alkyl, aryl, $C_1$-$C_4$ alkyl aryl, $C_1$-$C_4$ alkyl heteroaryl, $C_1$-$C_4$ alkyl heterocyclyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, $C_1$-$C_4$ carboxyl, or form a ring with each other or with A;

wherein A is $C_1$-$C_4$ alkyl, $C_1$-$C_4$ alkyl aryl, $C_1$-$C_4$ alkyl heteroaryl, or forms a ring structure with $R^1$, $R^2$ or $R^3$;

wherein B is hydrogen, an aryl group, a heteroaryl group, a cycloalkyl group, a heterocycloalkyl group, $C_1$-$C_{22}$ alkyl, $C_1$-$C_{22}$ alkyl aryl, $C_1$-$C_{22}$ alkyl heteroaryl, $C_2$-$C_{22}$ alkenyl, $C_2$-$C_{22}$ alkynyl, $C_1$-$C_{22}$ carbonyl, $C_1$-$C_{22}$ carbonylamino, $C_1$-$C_{22}$ alkoxy, $C_1$-$C_{22}$ sulfonyl, $C_1$-$C_{22}$ sulfonylamino, $C_1$-$C_{22}$ thioalkyl, or $C_1$-$C_{22}$ carboxyl, the stereocenters present, if any, being either 'R' or 'S' in configuration independently;

wherein $X^1$, $X^2$, and $X^3$ are, independently, hydrogen, hydroxyl, halogen, $C_1$-$C_4$ alkyl, $C_2$-$C_4$ alkenyl, $C_2$-$C_4$ alkynyl, amino, aminocarbonyl, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl;

wherein the double circle

indicates an aromatic or heteroaromatic ring; and wherein each Z is independently a bond, $C_1$-$C_4$ alkyl, heteroalkyl, or an O atom.

In Formula I, any and all of the stereocenters may be independently either 'R' or 'S' in configuration.

Certain embodiments of Formula I include compounds of Formula III:

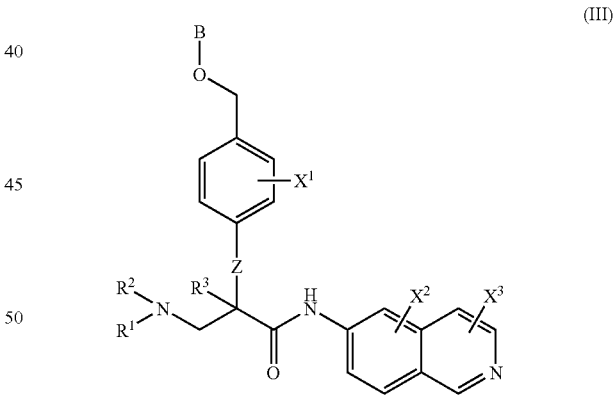

(III)

wherein $R^1$ and $R^2$ are independently hydrogen, $C_1$-$C_4$ alkyl, $C_1$-$C_4$ alkyl aryl, $C_1$-$C_4$ alkyl heteroaryl, $C_1$-$C_4$ alkyl heterocyclyl, or $R^1$ and $R^2$ together form a ring, either cycloalkyl or heterocycloalkyl;

wherein $R^3$ is hydrogen, $C_1$-$C_4$ alkyl, $C_1$-$C_4$ alkyl aryl, $C_1$-$C_4$ alkyl heteroaryl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl, or $R^3$ may from a ring with itself or $R^1$ or $R^2$, and the stereocenters present, if any, being either 'R' or 'S' in configuration independently;

wherein $X^1$, $X^2$, and $X^3$ are, independently, hydrogen, hydroxyl, halogen, $C_1$-$C_4$ alkyl, $C_2$-$C_4$ alkenyl, $C_2$-$C_4$ alkynyl, amino, aminocarbonyl, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl; and wherein B is hydrogen, $C_1$-$C_{18}$ alkyl, $C_1$-$C_{18}$ alkyl aryl, $C_1$-$C_{18}$ alkyl heteroaryl, $C_1$-$C_{18}$ carbonyl, $C_1$-$C_{18}$ carbonylamino, $C_1$-$C_{18}$ sulfonyl, $C_1$-$C_{18}$ sulfonylamino, or $C_1$-$C_{18}$ carboxyl, and the stereocenters present, if any, being either 'R' or 'S' in configuration independently.

Certain embodiments of Formula III include those wherein $R^1$, $R^2$, and $R^3$ are independently methyl or hydrogen, and wherein $X^1$, $X^2$, and $X^3$ are hydrogen. In another preferred embodiment of Formula III, B is an aliphatic carbonyl group. In another preferred embodiment of Formula III, B is a benzoic carbonyl group.

In other embodiments of Formula III, B is an aliphatic carbonyl group. In another preferred embodiment of Formula III, B is a benzoic carbonyl group.

Certain embodiments of Formula I are compounds of Formula IV:

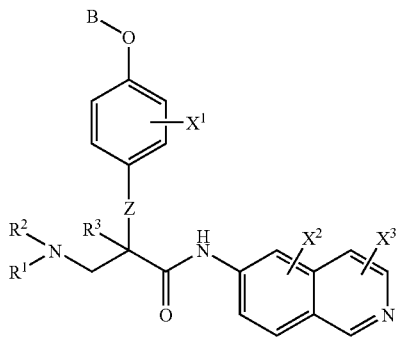

(IV)

wherein $R^1$ and $R^2$ are independently hydrogen, $C_1$-$C_4$ alkyl, $C_1$-$C_4$ alkyl aryl, $C_1$-$C_4$ alkyl heteroaryl, $C_1$-$C_4$ alkyl heterocyclyl, or $R^1$ and $R^2$ together form a ring, either cycloalkyl or heterocyclyl;

wherein $R^3$ is a hydrogen, $C_1$-$C_4$ alkyl, $C_1$-$C_4$ alkyl aryl, $C_1$-$C_4$ alkyl heteroaryl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl, and the stereocenters present, if any, being either 'R' or 'S' in configuration independently;

wherein $X^1$, $X^2$, and $X^3$ are, independently, hydrogen, hydroxyl, halogen, $C_1$-$C_4$ alkyl, $C_2$-$C_4$ alkenyl, $C_2$-$C_4$ alkynyl, amino, aminocarbonyl, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl;

wherein B is hydrogen, $C_1$-$C_{18}$ alkyl, $C_1$-$C_{18}$ alkyl aryl, $C_1$-$C_{18}$ alkyl heteroaryl, $C_1$-$C_{18}$ carbonyl, $C_1$-$C_{18}$ carbonylamino, $C_1$-$C_{18}$ sulfonyl, $C_1$-$C_{18}$ sulfonylamino, or $C_1$-$C_{18}$ carboxyl, and the stereocenters present, if any, being either 'R' or 'S' in configuration independently; and wherein Z is a bond, $C_1$-$C_4$ alkyl, heteroalkyl, or an O atom.

Certain embodiments of Formula IV are those wherein $R^1$, $R^2$, and $R^3$ are independently methyl or hydrogen, and wherein $X^1$, $X^2$, and $X^3$ are hydrogen.

In other embodiments of Formula IV, B is an aliphatic carbonyl group. In other embodiments of Formula IV, B is a benzoic, pyridyl, naphthyl, benzothiophene, or thiazole carbonyl group. In other embodiments of Formula IV, B is $C_1$-$C_2$ alkyl aryl, $C_2$-carbonyl, $C_2$-carbonyl amino, $C_2$-carboxyl, or $C_2$-hydroxyl aryl.

Benzamide compounds according to the invention may include those represented by Formula II:

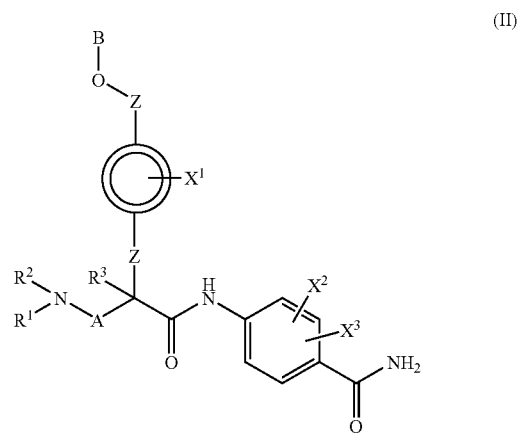

(II)

wherein $R^1$, $R^2$, and $R^3$ are independently hydrogen, $C_1$-$C_4$ alkyl, aryl, $C_1$-$C_4$ alkyl aryl, $C_1$-$C_4$ alkyl heteroaryl, $C_1$-$C_4$ alkyl heterocyclyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, $C_1$-$C_4$ carboxyl, or form a ring with each other or with A;

wherein A is $C_1$-$C_4$ alkyl, or forms a ring structure with $R^1$, $R^2$, or $R^3$;

wherein B is hydrogen, an aryl group, a heteroaryl group, a cycloalkyl group, a heterocycloalkyl group, $C_1$-$C_{22}$ alkyl, $C_1$-$C_{22}$ alkyl aryl, $C_1$-$C_{22}$ alkyl heteroaryl, $C_2$-$C_{22}$ alkenyl, $C_2$-$C_{22}$ alkynyl, $C_1$-$C_{22}$ carbonyl, $C_1$-$C_{22}$ carbonylamino, $C_1$-$C_{22}$ alkoxy, $C_1$-$C_{22}$ sulfonyl, $C_1$-$C_{22}$ sulfonylamino, $C_1$-$C_{22}$ thioalkyl, or $C_1$-$C_{22}$ carboxyl, and the stereocenters present, if any, being either 'R' or 'S' in configuration independently;

wherein $X^1$, $X^2$, and $X^3$ are, independently, hydrogen, hydroxyl, halogen, $C_1$-$C_4$ alkyl, $C_2$-$C_4$ alkenyl, $C_2$-$C_4$ alkynyl, amino, aminocarbonyl, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl;

wherein the double circle

indicates an aromatic or heteroaromatic ring; and wherein each Z is independently a bond, $C_1$-$C_4$ alkyl, heteroalkyl, or an O atom.

In Formula II, any and all of the stereocenters may be independently either 'R' or 'S' in configuration.

In certain embodiments of Formula II, $R^1$ is hydrogen or $C_1$-$C_4$ alkyl; B is $C_1$-$C_{22}$ carbonyl; the stereocenters present, if any, are either 'R' or 'S' in configuration independently; $X_1$, $X_2$, and $X_3$ are independently hydrogen or halogen; the double circle

indicates an aromatic or heteroaromatic ring; and Z is a bond, $C_1$-$C_4$ alkyl, heteroalkyl, or an O atom.

Compounds according to the invention include those according to Formula V:

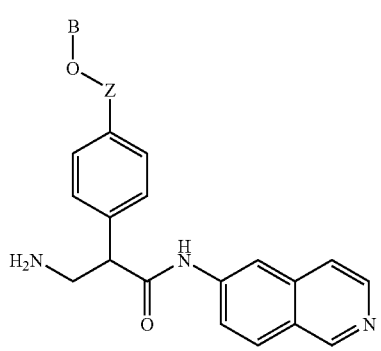

(V)

wherein Z is a bond or —$CH_2$—; and

B is an aryl group, a heteroaryl group, a cycloalkyl group, a heterocycloalkyl group, $C_1$-$C_{22}$ alkyl, $C_1$-$C_{22}$ alkyl aryl, $C_1$-$C_{22}$ alkyl heteroaryl, $C_2$-$C_{22}$ alkenyl, $C_2$-$C_{22}$ carbonyl, $C_1$-$C_{22}$ carbonylamino, $C_1$-$C_{22}$ alkoxy, $C_1$-$C_{22}$ sulfonyl, $C_1$-$C_{22}$ sulfonylamino, $C_1$-$C_{22}$ thioalkyl, or $C_1$-$C_{22}$ carboxyl.

Compounds according to the invention include those according to Formula (VI):

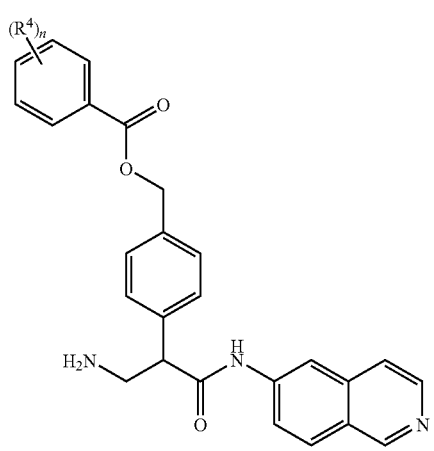

(VI)

wherein $R^4$ is $C_1$-$C_4$ alkyl and n is 0-3.

In some embodiments, $R^4$ is methyl and n is 2.

Compounds according to the invention may include salts and solvates of the compounds according to Formulas I, II, III, IV, V, or VI. When racemates exists, each enantiomer or diastereomer may be separately used, or they may be combined in any proportion. Where tautomers exist all possible tautomers are specifically contemplated.

Compounds according to the invention include compounds E482-E496 shown below:

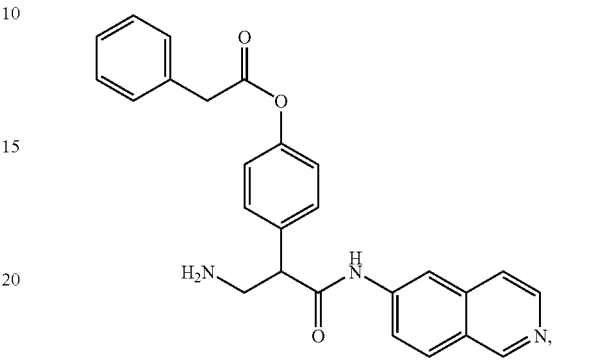

E482

4-(3-amino-1-(isoquinolin-6-ylamino)-1-oxopropan-2-yl)phenyl 2-phenylacetate

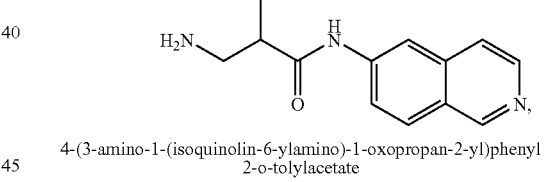

E483

4-(3-amino-1-(isoquinolin-6-ylamino)-1-oxopropan-2-yl)phenyl 2-o-tolylacetate

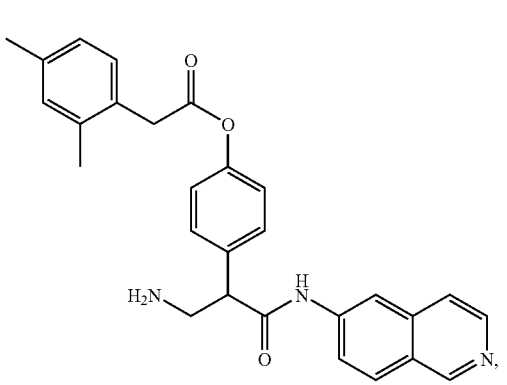

E484

4-(3-amino-1-(isoquinolin-6-ylamino)-1-oxopropan-2-yl)phenyl 2-(2,4-dimethylphenyl)acetate

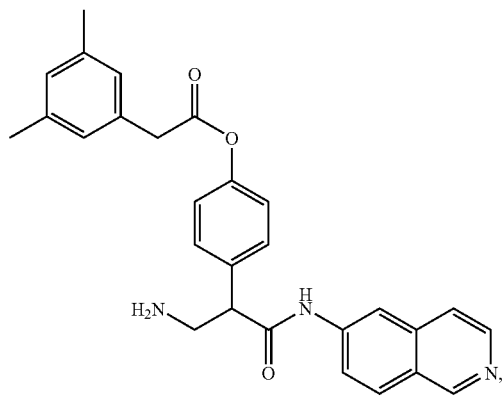

4-(3-amino-1-(isoquinolin-6-ylamino)-1-oxopropan-2-yl)phenyl
2-(3,5-dimethylphenyl)acetate

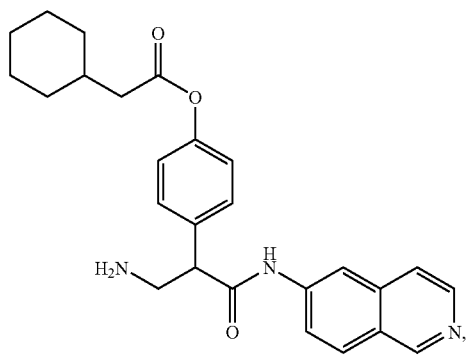

4-(3-amino-1-(isoquinolin-6-ylamino)-1-oxopropan-2-yl)phenyl
2-cyclohexylacetate

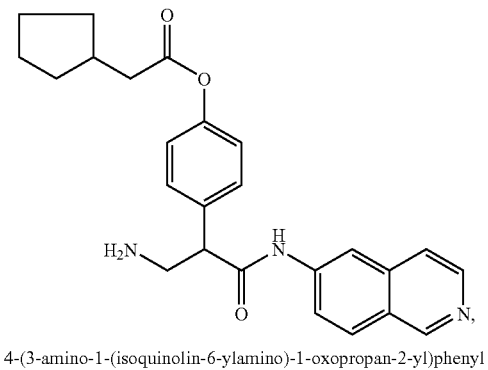

4-(3-amino-1-(isoquinolin-6-ylamino)-1-oxopropan-2-yl)phenyl
2-cyclopentylacetate

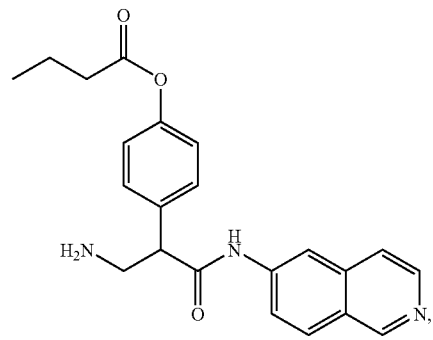

4-(3-amino-1-(isoquinolin-6-ylamino)-1-oxopropan-2-yl)phenyl
butyrate

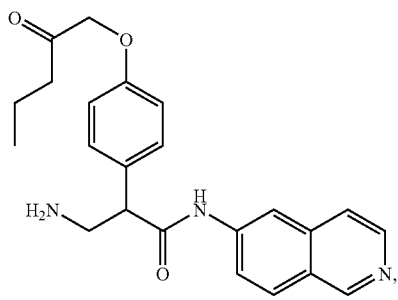

4-(3-amino-1-(isoquinolin-6-ylamino)-1-oxopropan-2-yl)benzyl
butyrate

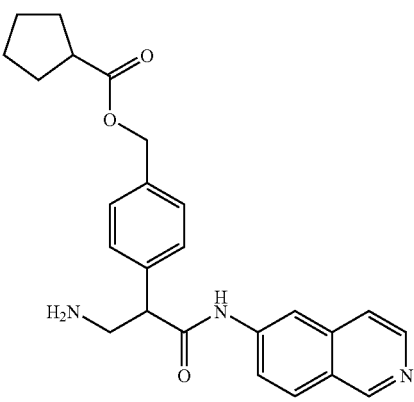

4-(3-amino-1-(isoquinolin-6-ylamino)-1-oxopropan-2-yl)benzyl
cyclopentanecarboxylate

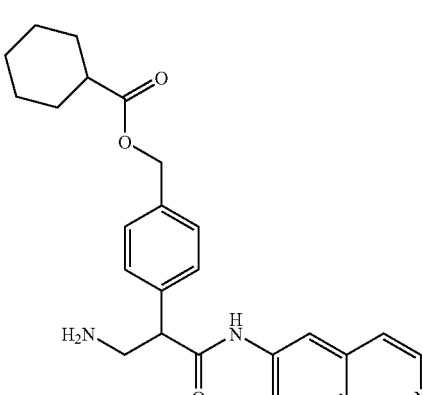

4-(3-amino-1-(isoquinolin-6-ylamino)-1-oxopropan-2-yl)benzyl
cyclohexanecarboxylate

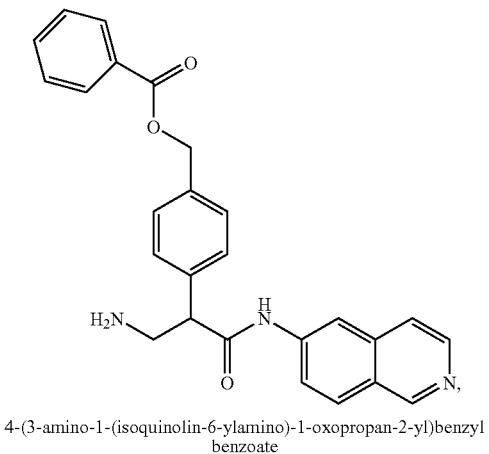

4-(3-amino-1-(isoquinolin-6-ylamino)-1-oxopropan-2-yl)benzyl benzoate

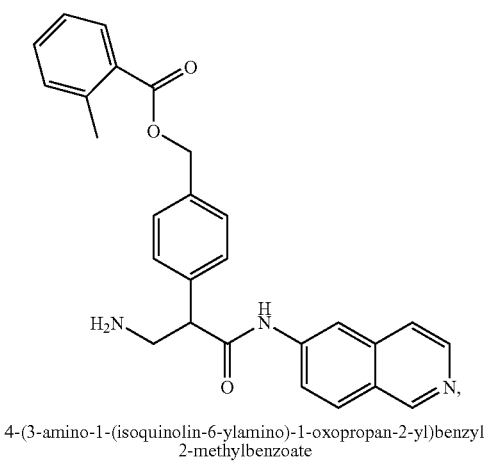

4-(3-amino-1-(isoquinolin-6-ylamino)-1-oxopropan-2-yl)benzyl 2-methylbenzoate

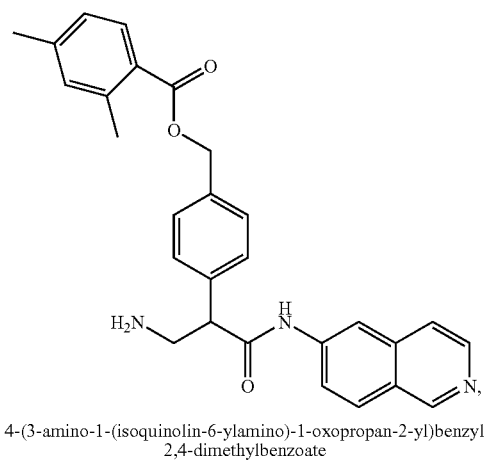

4-(3-amino-1-(isoquinolin-6-ylamino)-1-oxopropan-2-yl)benzyl 2,4-dimethylbenzoate

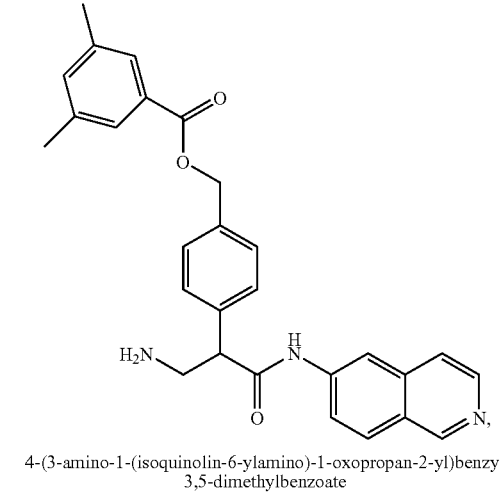

4-(3-amino-1-(isoquinolin-6-ylamino)-1-oxopropan-2-yl)benzyl 3,5-dimethylbenzoate

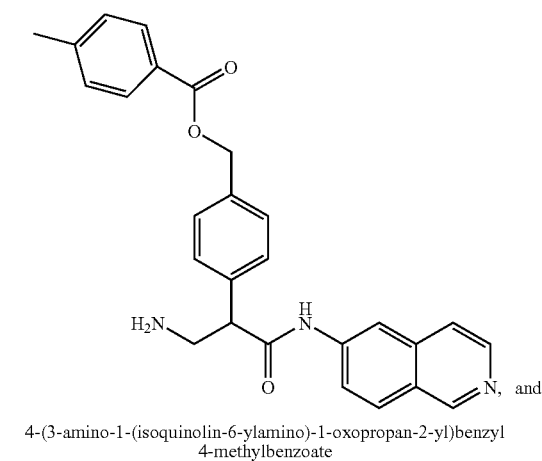

4-(3-amino-1-(isoquinolin-6-ylamino)-1-oxopropan-2-yl)benzyl 4-methylbenzoate

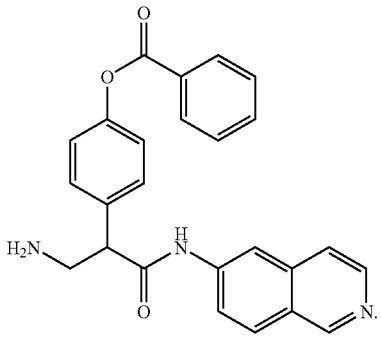

Synthesis of Compounds

The amino isoquinoline amide or substituted benzamide compounds may be synthesized according to the general schemes shown in FIGS. 1-5.

According to the synthesis scheme in FIG. 1, ester (1) may be protected with the TIPS group and alkylated with bromomethylphthalimide to give compound (3). The ester may be then hydrolyzed with LiOH*H$_2$O to give diacid (4) and coupled with 6-aminoisoquinoline using EDC as the coupling agent. The amine (6) may be accomplished using hydrazine which may be then protected with Boc$_2$O to give (7). Deprotection of the hydroxyl group may be carried out with TBAF, and coupling with the appropriate acid may be achieved with EDC or using the acid chloride. Deprotection of the amine may be accomplished with HCl to give the final amino isoquinoline amides.

Figure 2:
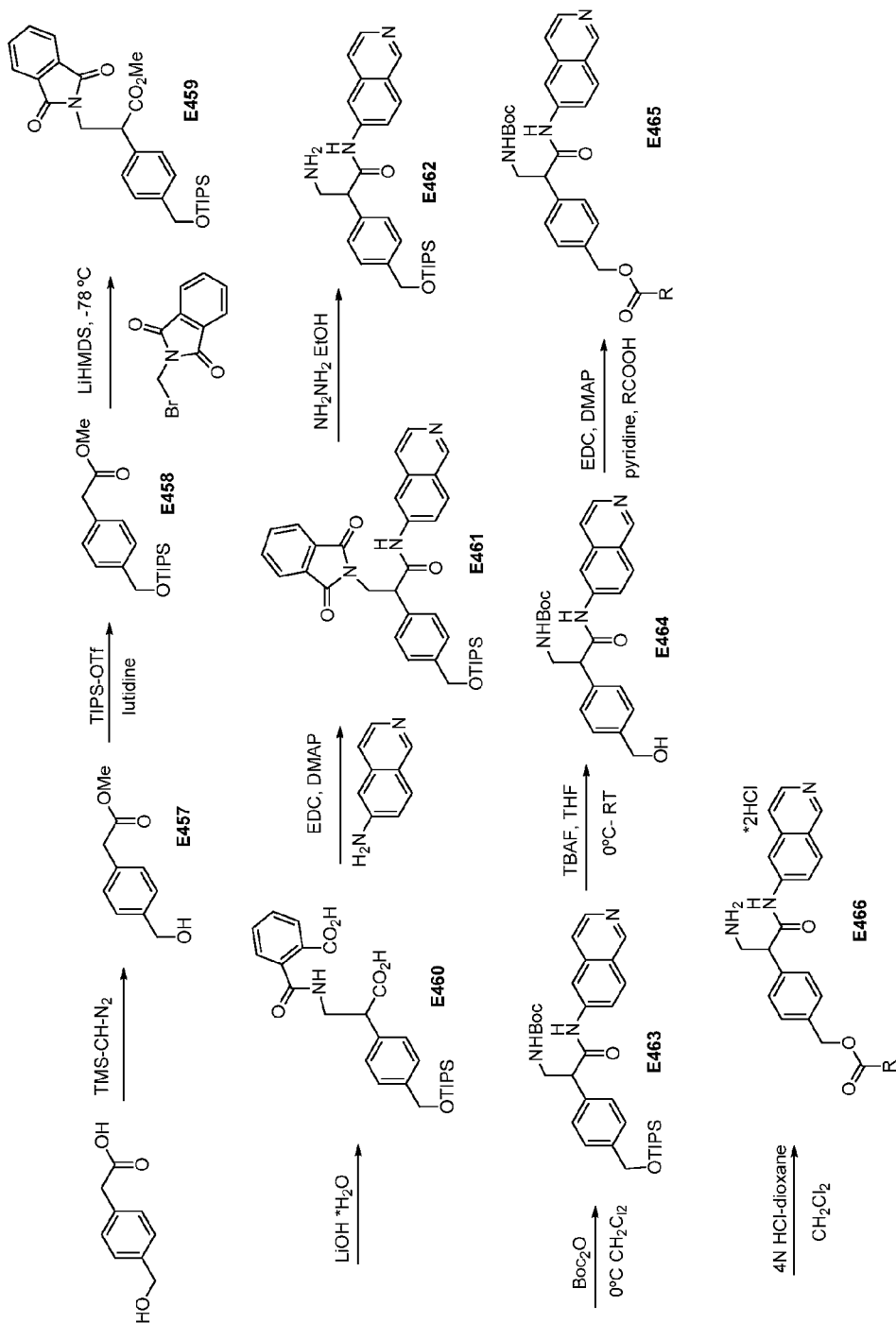
FIG. 2 is a scheme for the synthesis of compounds, including E457-E466.

As in FIG. 1, the synthesis scheme in FIG. 2 may begin by protecting 2-(4-(hydroxymethyl)phenyl)acetic acid as the methyl ester and the TIPS alcohol to give E457. This methyl ester may be then alkylated with bromomethylphthalimide to give compound E459. The ester may be hydrolyzed with LiOH*H$_2$O to give diacid E460 and coupled with 6-aminoisoquinoline using EDC as the coupling agent giving compound E461. Formation of the amine E462 may be accomplished using hydrazine which may be then protected with Boc$_2$O to give E463. Deprotection of the hydroxyl group may be carried out with TBAF, and coupling with the appropriate acid may be achieved with EDC or using the acid chloride. Deprotection of the amine may be accomplished with HCl to give the final amino isoquinoline amides.

Figure 3:
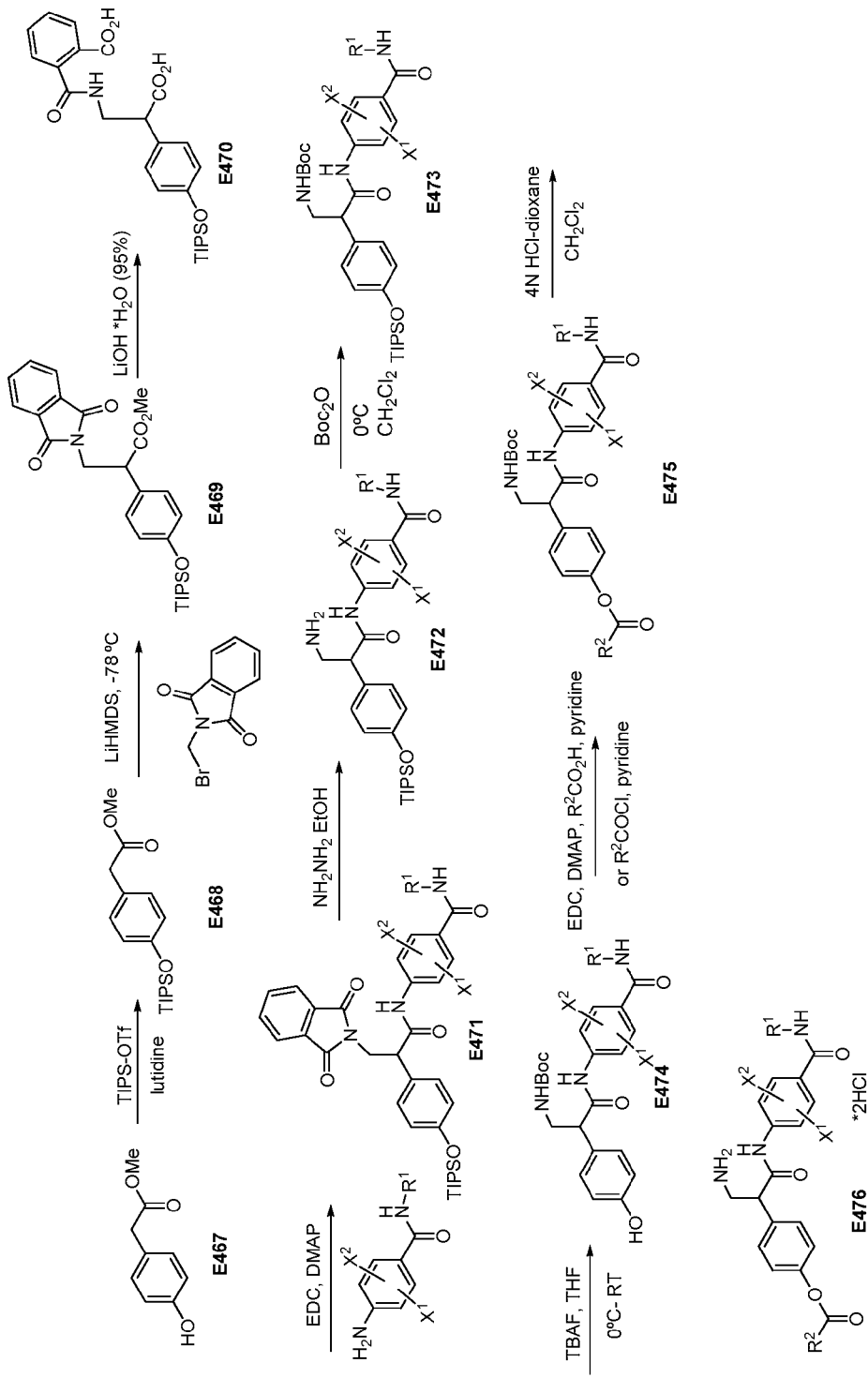
FIG. 3 is a scheme for the synthesis of benzamidines, E467-E476.

Benzamides may be synthesized using the procedures outlined in FIG. 2, but by substituting the para-amino benzamide of choice for the amino isoquinoline, as shown in the synthesis scheme in FIG. 3.

Figure 4:
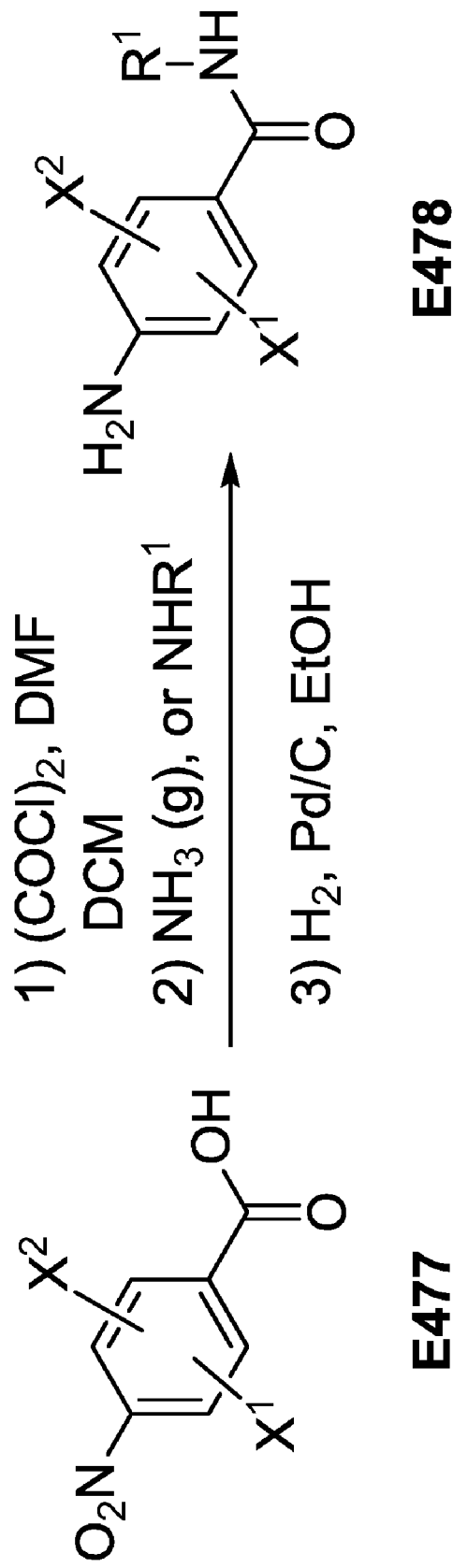
FIG. 4 is a scheme for the synthesis of para-aminobenzamide precursors, E477-E478, for the synthesis scheme of FIG. 3.
Figure 5:
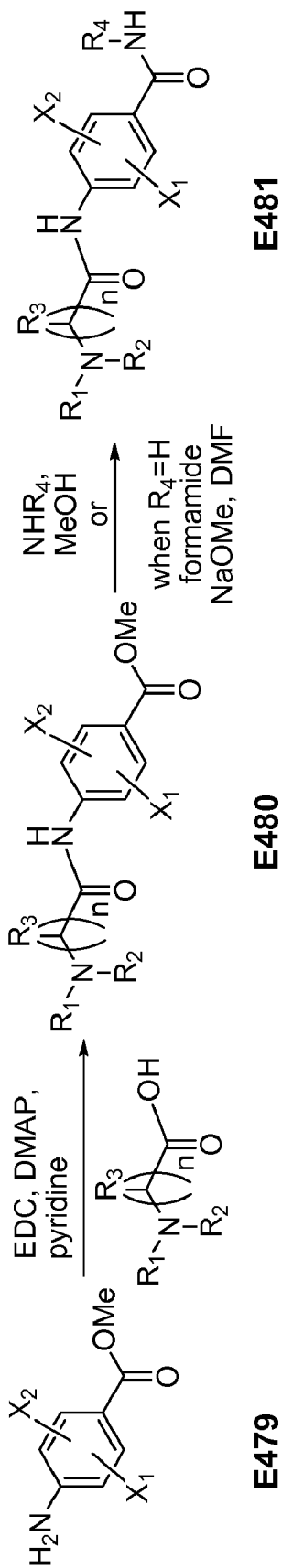
FIG. 5 is a scheme for the synthesis of para-aminobenzamide precursors, E479-E481, for the synthesis scheme of FIG. 3.

The para-aminobenzamide precursors of the synthesis scheme in FIG. 3 may be commercially-available, or may be synthesized by the general synthesis schemes of FIGS. 4-5.

According to FIG. 4, the appropriate acid may be converted to its acid chloride with oxalyl chloride then reacted with ammonia gas or another amine to give the amide. The nitro group may be reduced to the aniline with hydrogen or another reducing agent. The aniline may be then coupled with an appropriate acid using standard coupling procedures such as EDC and DMAP in pyridine as shown in FIG. 3.

An alternative synthetic route is outlined in the synthesis scheme of FIG. 5. According to FIG. 5, the aniline may be coupled with an appropriate acid using standard coupling procedures such as EDC and DMAP in pyridine. The ester may be then converted to the corresponding primary amide using formamide and NaOMe in DMF or to a substituted amide by heating with the appropriate amine in a solvent such as MeOH.

The abbreviations used in the synthetic schemes shown in the figures have the following meanings: Boc$_2$O is di-tert-butyl-dicarbonate, DMAP is dimethyl aminopyridine, DMSO is Dimethyl Sulfoxide, HATU is 2-(7-Aza-1H-benzotriazole-1-yl)-1,1,3,3-tetramethyluronium hexafluorophosphate, LDA is lithium diisopropyl amide, DMF is dimethylformamide, THF is tetrahydrofuran, and EDC is N-(3-dimethylaminopropyl)-N'-ethylcarbodiimide hydrochloride.

Compositions

The compounds of Formulas I-VI may be provided or formulated in a composition. The compounds may be administered in a pharmaceutically acceptable formulation, such as in or with a pharmaceutically acceptable carrier.

Compounds according to the invention may be administered in conjunction with one or more additional therapeutic agents. Suitable additional therapeutic agents may include, but are not limited to, beta blockers, alpha-agonists, carbonic anhydrase inhibitors, prostaglandin-like compounds, miotic or cholinergic agents, or epinephrine compounds.

Beta blockers reduce the production of aqueous humor. Examples include levobunolol (BETAGAN®), timolol (BETIMOL®, TIMOPTIC®), betaxolol (BETOPTIC®) and metipranolol (OPTIPRANOLOL®).

Alpha-agonists reduce the production of aqueous humor and increase drainage. Examples include apraclonidine (IOPIDINE®) and brimonidine (ALPHAGAN®).

Carbonic anhydrase inhibitors reduce the production of aqueous humor. Examples include dorzolamide (TRUSOPT®) and brinzolamide (AZOPT®).

Prostaglandins and prostaglandin-like compounds increase the outflow of aqueous humor. Examples include latanoprost (XALATAN®), bimatoprost (LUMIGAN®), and travoprost (TRAVATAN™).

Miotic or cholinergic agents increase the outflow of aqueous humor. Examples include pilocarpine (ISOPTO CARPINE®, PILOPINE®) and carbachol (ISOPTO CARBACHOL®).

Epinephrine compounds, such as dipivefrin (PROPINE®), also increase the outflow of aqueous humor.

The additional therapeutic agent or agents may be administered simultaneously or sequentially with the compounds of the present invention. Sequential administration includes administration before or after the compounds of the present invention. In some embodiments, the additional therapeutic agent or agents may be administered in the same composition as the compounds of the present invention. In other embodiments, there may be an interval of time between administration of the additional therapeutic agent and the compounds of the present invention.

In some embodiments, the administration of an additional therapeutic agent with a compound of the present invention may enable lower doses of the other therapeutic agents and/or administration at less frequent intervals.

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

Compositions of the present invention may comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of treatment, the nature of concurrent therapy, the particular pharmaceutically-acceptable carrier utilized, and like factors within the knowledge and expertise of the attending physician.

The route by which the compounds of the present invention (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic or topical composition is typically about 1 to about 8%.

Ingredient o) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions may vary depending on the type of systemic composition prepared, the specific derivative selected for component A and the ingredients of component B, in general, system compositions comprise 0.01% to 50% of component A and 50% to 99.99% of component B.

Compositions for parenteral administration typically comprise A) 0.1% to 10% of the compounds of the present invention and B) 90% to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50% to about 95% of component B), and more particularly, from about 50% to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the compounds of the present invention are topically administered. Topical compositions that can be applied locally to the eye may be in any form known in the art, non-limiting examples of which include solids, liquid drops, gelable drops, sprays, ointments, or a sustained or non-sustained release unit placed in the conjunctival cul-du-sac of the eye or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the skin. Component B may further comprise one or more optional components.

The amount of the carrier employed in conjunction with component A is sufficient to provide a practical quantity of composition for administration per unit dose of the medicament. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5% to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0% to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0% to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0% to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0% to about 95%.

Ingredient v) is a powder. The amount of ingredient v) in the topical composition is typically 0% to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0% to about 0.5%, particularly, about 0.001% to about 0.1%. For ocular applications a fragrance is not typically used.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0% to about 10%. For ocular applications a pigment is generally not used.

In other certain embodiments of the invention, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, Tris(hydroxymethyl) aminomethane hydrochloride, sodium chloride, potassium chloride, and combinations thereof.

Examples of cc) pH adjusting additives include HCl or NaOH in amounts sufficient to adjust the pH of the topical pharmaceutical composition for ocular administration to 5.0-7.5.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

Methods of Use

Compounds according to Formulas I-VI and compositions including them may have kinase inhibitory activity and thus may be useful in influencing or inhibiting the action of kinases, and in the treatment and/or prevention of diseases or conditions influenced by kinases. At a minimum, they may have NET activity and this may be useful for influencing the action of NET. In some embodiments, methods are provided that may comprise administering a composition comprising a specific ligand that interacts strongly with a kinase, specifically and at minimum a rho kinase, and that also interacts with monoamine transporter proteins (MATs), specifically and at minimum with NET proteins.

According to certain embodiments, provided are methods of influencing and/or inhibiting the action of a kinase in a cell or medium. In certain embodiments, provided are methods of influencing and/or inhibiting NET in a cell or medium. A cell may be in vitro, in a body in vivo, or in a living body in vivo. A medium may include an assay medium. The methods may comprise applying to a medium or contacting a cell with an effective amount of a compound according to Formula I, II, III, IV, V, or VI. The methods may comprise applying to a medium or contacting a cell with composition comprising an effective amount of a compound according to Formula I, II, III, IV, V, or VI, and a pharmaceutically acceptable carrier. In some embodiments, the kinase inhibited may be a rho kinase.

According to certain embodiments, provided are methods of treating a disease, disorder, or condition. The methods may comprise administering to a subject a compound according to Formula I, II, III, IV, V, or VI. The methods may comprise administering to a subject a composition comprising a compound according to Formula I, II, III, IV, V, or VI, and a pharmaceutically acceptable carrier. Diseases, disorders, or conditions may include any of the diseases or conditions associated with kinase activity or diseases or conditions affected by kinases. For example, the disease may be selected from the group consisting of eye disease including glaucoma and retinal diseases such as Wet AMD Dry AMD (inflammation) and DME, bone disorder including osteoporosis, vascular disease including cerebral vasospasm, coronary vasospasm, hypertension, pulmonary hypertension, sudden death syndrome, angina, myocardial infarction, restenosis, stroke, hypertensive vascular disease, heart failure, cardiac allograft vasculopathy, vein graft disease, pulmonary disease including chronic obstructive pulmonary disease (COPD) and asthma, neurological disorder including spinal cord injury, Alzheimer's disease, multiple sclerosis, depression, attention deficit-hyperactivity disorder and neuropathic pain, neovascular disorders and cancer, obesity, and erectile dysfunction. The compounds of the present invention may also be useful in decreasing intraocular pressure. Thus, these compounds may be useful in the treatment of glaucoma. The preferred route of administration for treating glaucoma is topically.

In further aspects, the invention provides methods of modulating kinase activity, the methods comprising contacting a cell with a compound according to Formula I, II, III, IV, V, or VI as described above, in an amount effective to modulate kinase activity.

In further aspects, the invention provides methods of reducing intraocular pressure, the methods comprising contacting a cell with a compound according to Formula I, II, III, IV, V, or VI as described above, in an amount effective to reduce intraocular pressure.

The dosage range of the compound for systemic administration is from about 0.001 to about 100 mg/kg body weight, preferably from about 0.01 to about 10 mg/kg per body weight, most preferably form about 0.05 to about 5 mg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.1 to 1000 ng/mL, more preferably from 0.5 to 500 ng/mL and most preferably from 1 to 100 ng/mL. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The invention will be further explained by the following illustrative examples that are to be considered to be non-limiting.

Examples

Reference Example 1

All temperatures were in degrees Centigrade. Reagents and starting materials were purchased from commercial sources or prepared following published literature procedures.

Unless otherwise noted, HPLC purification, when appropriate, was performed by redissolving the compound in a small volume of DMSO and filtering through a 0.45 micron (nylon disc) syringe filter. The solution was then purified using, for example, a 50 mm Varian Dynamax HPLC 21.4 mm Microsorb Guard-8 $C_8$ column. A typical initial eluting mixture of 40-80% MeOH:$H_2O$ was selected as appropriate for the target compound. This initial gradient was maintained for 0.5 min then increased to 100% MeOH:0% $H_2O$ over 5 min. 100% MeOH was maintained for 2 more min before re-equilibration back to the initial starting gradient. A typical total run time was 8 min. The resulting fractions were analyzed, combined as appropriate, and then evaporated to provide purified material.

Proton magnetic resonance ($^1$H NMR) spectra were recorded on either a Varian INOVA 600 MHz ($^1$H) NMR spectrometer, Varian INOVA 500 MHz ($^1$H) NMR spectrometer, Varian Mercury 300 MHz ($^1$H) NMR spectrometer, or a Varian Mercury 200 MHz ($^1$H) NMR spectrometer. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

Analytical LCMS spectra were obtained using a Waters ZQ MS ESI instrument with an Alliance 2695 HPLC and a 2487 dual wavelength UV detector. Spectra were analyzed at 254 and 230 nm. Samples were passed through a Waters Symmetry C18 4.6×75 mm 3.5µ column with or without a guard column (3.9×20 mm 5µ). Gradients were run with mobile phase A: 0.1% formic acid in $H_2O$ and mobile phase B: ACN with a flow rate of 0.8 mL/min. Two gradients will illustrate:

| Gradient A | | |
|---|---|---|
| Time | A % | B % |
| 0.00 | 80.0 | 20.0 |
| 1.00 | 80.0 | 20.0 |
| 6.00 | 25.0 | 75.0 |
| 7.00 | 5.0 | 95.0 |
| 8.00 | 5.0 | 95.0 |
| 9.00 | 80.0 | 20.0 |
| 12.00 | 80.0 | 20.0 |

| Gradient B | | |
|---|---|---|
| Time | A % | B % |
| 0.00 | 95.0 | 20.0 |
| 1.00 | 9.0 | 25.0 |
| 6.00 | 40.0 | 75.0 |
| 7.00 | 5.0 | 95.0 |
| 8.00 | 5.0 | 95.0 |
| 9.00 | 95.0 | 20.0 |
| 12.00 | 95.0 | 20.0 |

The settings for the MS probe were a cone voltage at 38 mV and a desolvation temperature at 250° C. Any variations in these methods are noted below.

The following preparations illustrate procedures for the preparation of intermediates and methods for the preparation of an amino isoquinoline amide derivatives or substituted benzamide derivatives.

Examples 1-12

Figure 6:
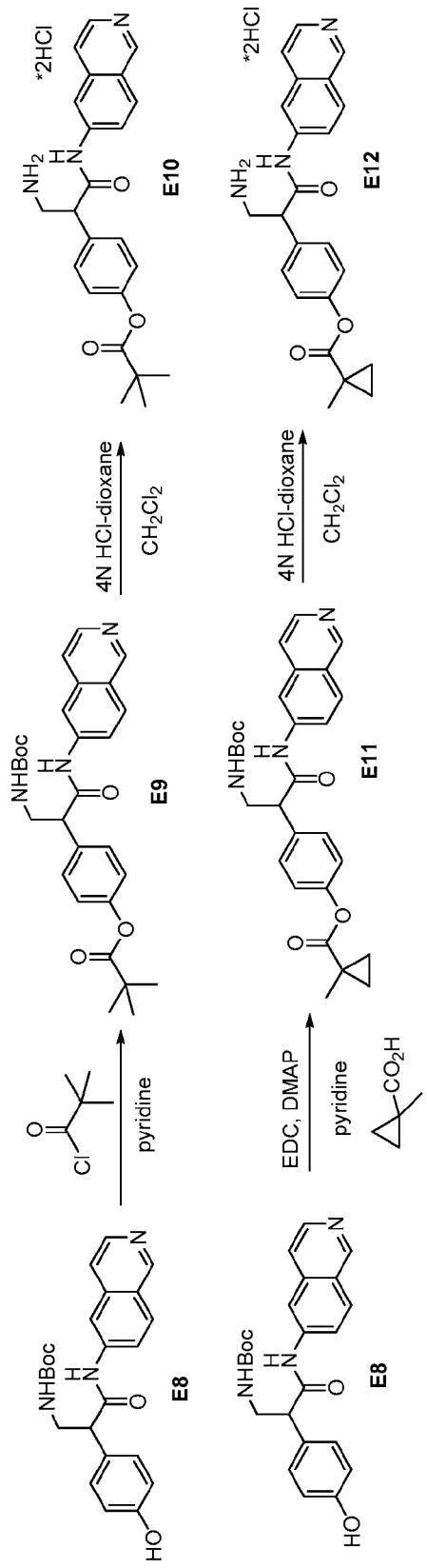
FIG. 6 is a scheme for the synthesis of compounds, including E8-E12.

Compounds E1-E12 may be synthesized according to the scheme shown in FIG. 1 and FIG. 6. For example, methyl 2-(4-(triisopropylsilyloxy)phenyl)acetate (E2) was synthesized from E1 according to the below:

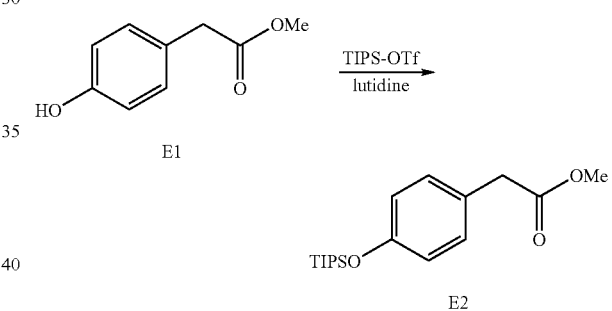

To methyl 2-(4-hydroxyphenyl)acetate (E1) in $CH_2Cl_2$ at 0° C. was added 2,6-lutidine and TIPS-OTf. The ice bath was removed and the solution was allowed to warm to room temperature and stirred. After 4 h the solution was poured into $NH_4Cl_{(sat)}$ and $CH_2Cl_2$ and the organic layer was further extracted with $NH_4Cl_{(sat)}$. The organics were dried ($Na_2SO_4$) filtered and evaporated. Column chromatography (0-15% EtOAc/Hexanes) gave pure methyl-2-(4-(triisopropylsilyloxy)phenyl)acetate (E2).

Methyl 3-(1,3-dioxoisoindolin-2-yl)-2-(4-(triisopropylsilyloxy)phenyl)propanoate (E3) was prepared from E2 according to the below:

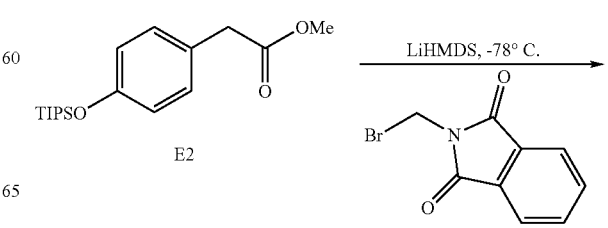

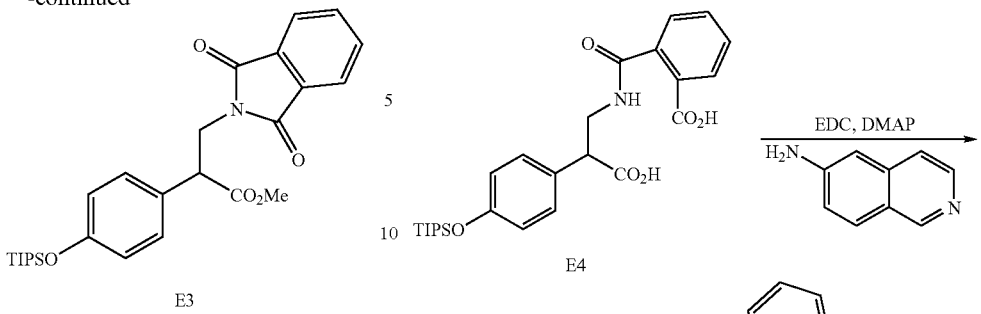

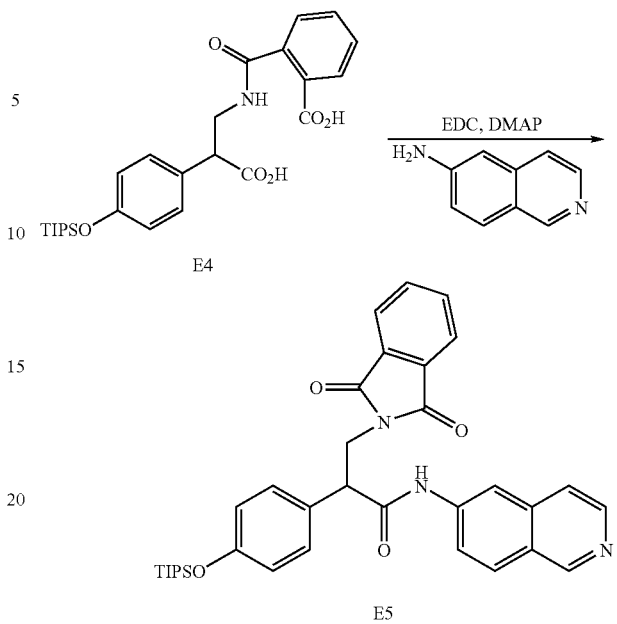

To a solution of LiHMDS in THF cooled to −78° C. was added a cooled solution (approx −78° C.) of methyl-2-(4-(triisopropylsilyloxy)phenyl)acetate (E2) in THF via syringe. The solution was stirred at −78° C. for 30 min. Bromo-methyl phthalimide was added directly to the anion, and the solution was immediately removed from the −78° C. bath and placed in an ice bath and stirred for 2 h. The reaction was then poured into NH$_4$Cl$_{(sat)}$ and extracted with EtOAc. The organics were dried (Na$_2$SO$_4$), filtered, and evaporated. Column chromatography 0-20% EtOAc/Hexanes gave pure methyl 3-(1,3-dioxoisoindolin-2-yl)-2-(4-(triisopropylsilyloxy)phenyl)propanoate (E3).

2-(2-Carboxy-2-(4-(triisopropylsilyloxy)phenyl)ethylcarbamoyl)benzoic acid (E4) was prepared from E3 according to the below:

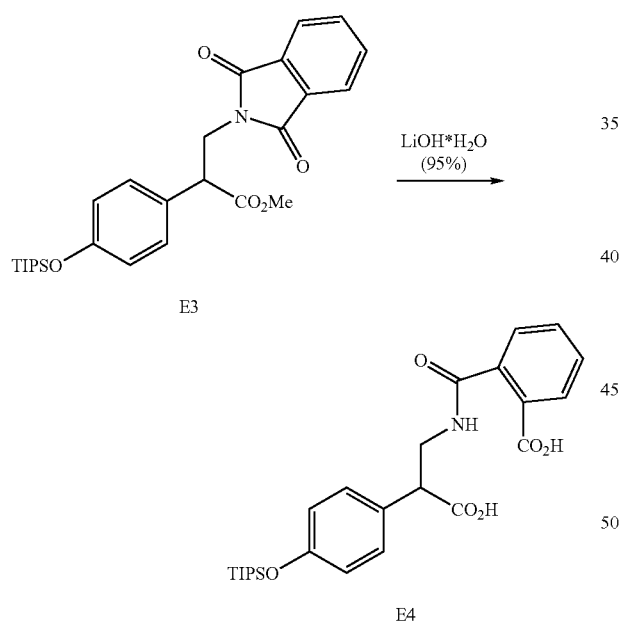

To methyl 3-(1,3-dioxoisoindolin-2-yl)-2-(4-(triisopropylsilyloxy)phenyl)propanoate (E3) in THF/H$_2$O was added LiOH.H$_2$O, and the solution was stirred for 1.5 h or until conversion to product was visible by LC-MS. The solution was then poured into EtOAc/NH$_4$Cl(sat)/1 N HCl (3:1), and the aqueous layer was further extracted with EtOAc. The organics were dried (Na$_2$SO$_4$), filtered, evaporated, and dried to give crude 2-(2-carboxy-2-(4-(triisopropylsilyloxy)phenyl)ethylcarbamoyl)benzoic acid (E4).

3-(1,3-Dioxoisoindolin-2-yl)-N-(isoquinolin-6-yl)-2-(4-(triisopropylsilyloxy phenyl)propanamide (E5) was prepared from E4 according to the below:

To 2-(2-carboxy-2-(4-(triisopropylsilyloxy)phenyl)ethylcarbamoyl)benzoic acid (E4) in pyridine was added EDC, DMAP, and 6-aminoisoquinoline, and the solution was flushed with N$_2$, capped, and stirred overnight. The mixture was poured into EtOAc/NaHCO$_{3(sat)}$ and the aqueous layer was further extracted with EtOAc. The organics were dried (Na$_2$SO$_4$), filtered, and evaporated. Column chromatography 5% MeOH/CH$_2$Cl$_2$ gave pure 3-(1,3-dioxoisoindolin-2-yl)-N-(isoquinolin-6-yl)-2-(4-(triisopropylsilyloxy phenyl)propanamide (E5).

3-amino-N-(isoquinolin-6-yl)-2-(4-(triisopropylsilyloxy) phenyl)propanamide (E6) was prepared from E5 according to the below:

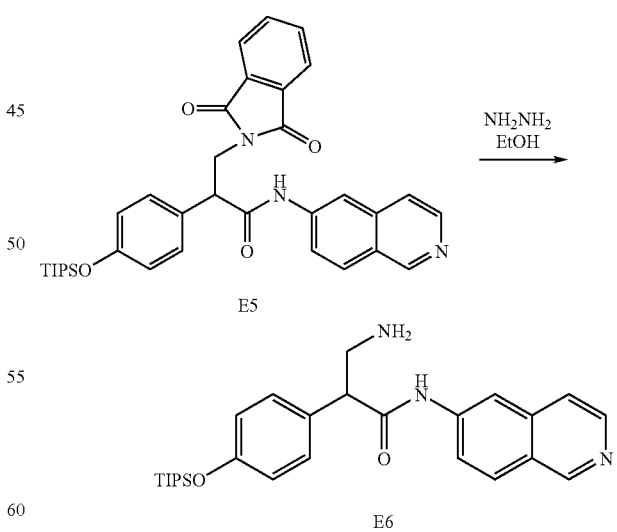

To 3-(1,3-dioxoisoindolin-2-yl)-N-(isoquinolin-6-yl)-2-(4-(triisopropylsilyloxy phenyl)propanamide (E5) in EtOH was added NH$_2$—NH$_2$, and the solution was refluxed for 1.2 hrs-2 hrs. The solids were filtered and the solvents were evaporated. Column chromatography 5% 2N NH$_3$-MeOH/CH$_2$Cl$_2$ gave pure 3-amino-N-(isoquinolin-6-yl)-2-(4-(triisopropylsilyloxy)phenyl)propanamide (E6).

Tert-butyl 3-(isoquinolin-6-ylamino)-3-oxo-2-(4-(triisopropylsilyloxy)phenyl)propyl carbamate (E7) was prepared from E6 according to the below:

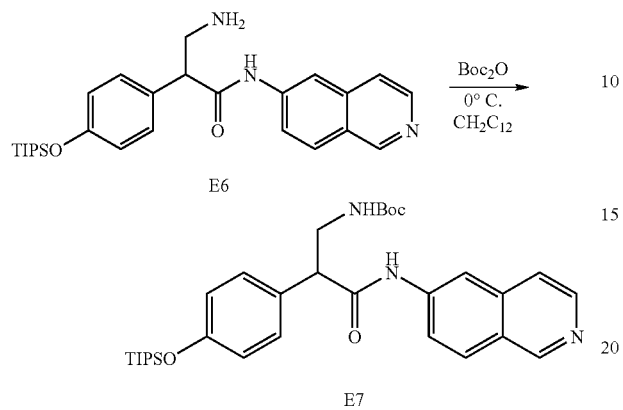

To 3-amino-N-(isoquinolin-6-yl)-2-(4-(triisopropylsilyloxy)phenyl)propanamide (E6) in CH$_2$Cl$_2$ (7.3 mL) at 0° C. was added a solution of Boc$_2$O in CH$_2$Cl$_2$ also cooled to 0° C. before addition. The solution stirred for 30 min at 0° C. and additional Boc$_2$O was added, and the solution was stirred for 30 min more then poured into CH$_2$Cl$_2$/NaHCO$_{3(sat)}$. The aqueous layers were further extracted with CH$_2$Cl$_2$, dried (Na$_2$SO$_4$), filtered, and evaporated. Column chromatography (3% MeOH/CH$_2$Cl$_2$) gave pure tert-butyl 3-(isoquinolin-6-ylamino)-3-oxo-2-(4-(triisopropylsilyloxy)phenyl)propylcarbamate (E7).

Tert-Butyl 2-(4-hydroxyphenyl)-3-(isoquinolin-6-ylamino)-3-oxopropylcarbamate (E8) was prepared from E7 according to the below:

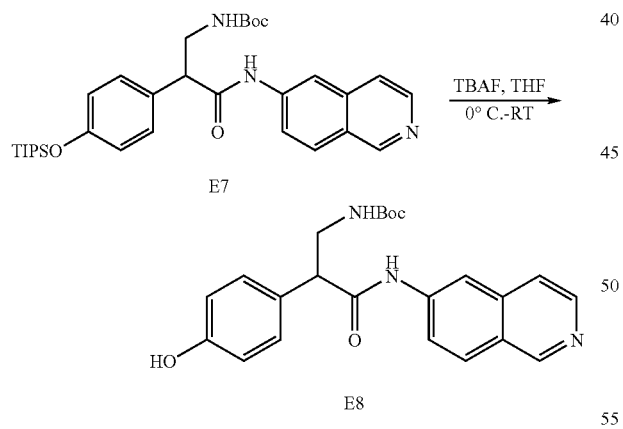

To tert-butyl 3-(isoquinolin-6-ylamino)-3-oxo-2-(4-(triisopropylsilyloxy)phenyl)propylcarbamate (E7) in THF at 0° C. was added TBAF, and the solution was stirred for 45 min at 0° C. The compound was poured into EtOAc and washed with NH$_4$Cl$_{(sat)}$, dried (Na$_2$SO$_4$), filtered, and evaporated. Column chromatography 6% MeOH/CH$_2$Cl$_2$ gave pure tert-butyl 2-(4-hydroxyphenyl)-3-(isoquinolin-6-ylamino)-3-oxopropylcarbamate (E8).

4-(3-tert-butoxycarbonylamino)-1-(isoquinolin-6-ylamino)-1-oxopropan-2-yl)phenylpivalate (E9) was prepared from E8 according to the below:

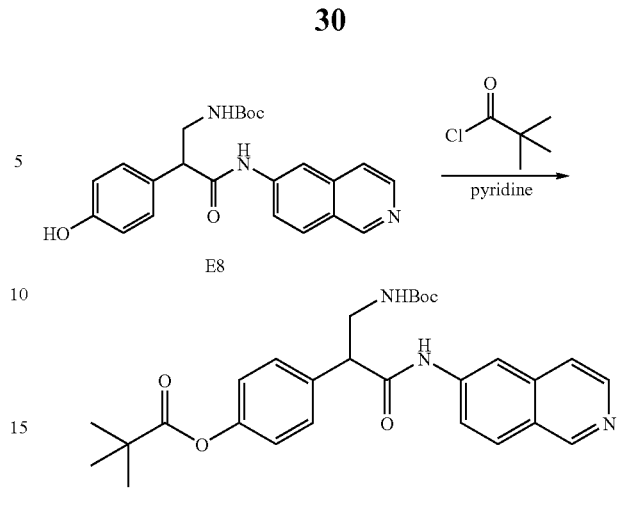

To tert-butyl 2-(4-hydroxyphenyl)-3-(isoquinolin-6-ylamino)-3-oxopropylcarbamate (E8) in pyridine was added pivaloyl chloride, and the solution was stirred for 2 h at room temperature. The mixture was poured into NaHCO$_3$ and extracted with EtOAc. The organics were dried (Na$_2$SO$_4$), filtered, and evaporated. Column chromatography 5% MeOH/CH$_2$Cl$_2$ gave pure 4-(3-tert-butoxycarbonylamino)-1-(isoquinolin-6-ylamino)-1-oxopropan-2-yl)phenylpivalate (E9).

4-(3-amino-1-(isoquinolin-6-ylamino)-1-oxopropan-2-yl)phenyl pivalate (E10) was prepared from E9 according to the below:

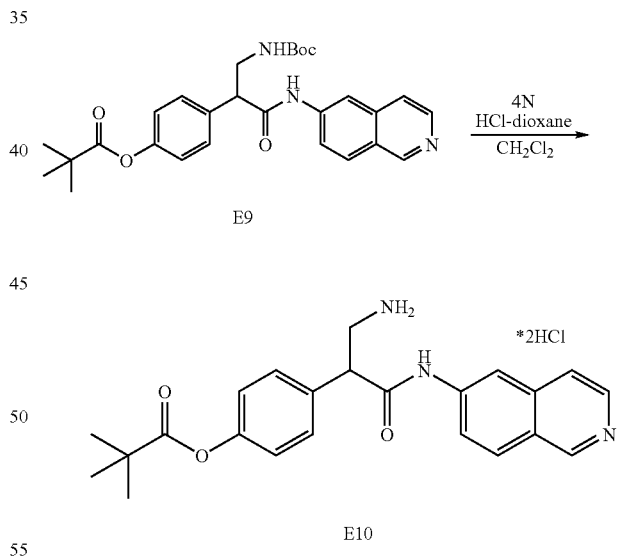

To 4-(3-tert-butoxycarbonylamino)-1-(isoquinolin-6-ylamino)-1-oxopropan-2-yl)phenylpivalate (E9) in CH$_2$Cl$_2$ was added HCl (4N in dioxane) and the solution was stirred for 8-10 h. The solvents were evaporated to give pure 4-(3-amino-1-(isoquinolin-6-ylamino)-1-oxopropan-2-yl)phenyl pivalate (E10).

4-(3-(tert-butoxycarbonylamino)-1-(isoquinolin-6-ylamino)-1-oxopropan-2-yl)phenyl 1-methylcyclopropanecarboxylate (E11) was prepared from E8 according to the below:

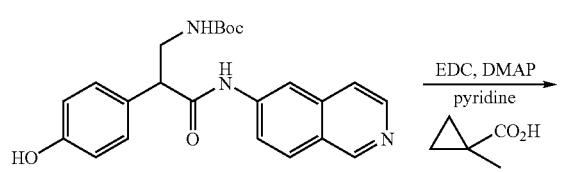

E8

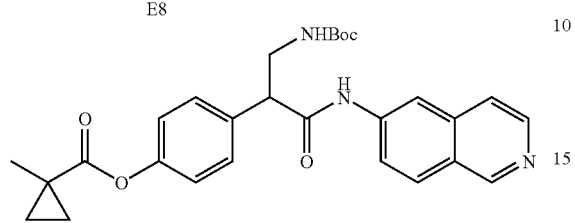

E11

To tert-butyl 2-(4-hydroxyphenyl)-3-(isoquinolin-6-ylamino)-3-oxopropylcarbamate (E8) in pyridine was added EDC, DMAP, and 1-methylcyclopropanecarboxylic acid, and the solution was flushed with N$_2$, capped, and stirred overnight. The mixture was poured into EtOAc/NaHCO$_{3(sat)}$ and the aqueous layer was further extracted with EtOAc. The organics were dried (Na$_2$SO$_4$), filtered, and evaporated. Column chromatography 5% MeOH/CH$_2$Cl$_2$ gave pure 4-(3-(tert-butoxycarbonylamino)-1-(isoquinolin-6-ylamino)-1-oxopropan-2-yl)phenyl 1-methylcyclopropanecarboxylate (E11).

4-(3-amino-1-(isoquinolin-6-ylamino)-1-oxopropan-2-yl)phenyl 1-methylcyclopropanecarboxylate dihydrochloride (E12) was prepared from E11 according to the below:

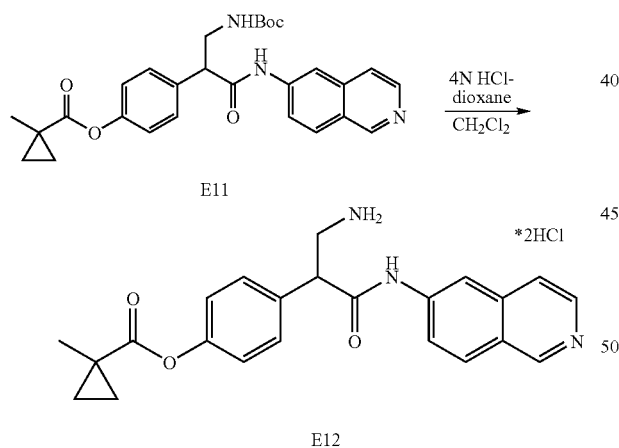

To 4-(3-(tert-butoxycarbonylamino)-1-(isoquinolin-6-ylamino)-1-oxopropan-2-yl)phenyl 1-methylcyclopropanecarboxylate (E11) in CH$_2$Cl$_2$ was added HCl (4N in dioxane) and the solution was stirred for 8-10 h. The solvents were evaporated to give pure 4-(3-amino-1-(isoquinolin-6-ylamino)-1-oxopropan-2-yl)phenyl 1-methylcyclopropanecarboxylate dihydrochloride (E12).

Examples 13-122

Using commercially available compounds and largely the procedures set forth in Examples 2-12 and substituting the appropriate starting materials, the compounds E13-E91 were made and E92-E122 could be synthesized, shown in Tables 1 and 2, respectively.

TABLE 1

Compounds E13-E91.

| Example | R$_2$ | R$_1$ |
|---|---|---|
| 10 | H | -i-Pr |
| 12 | H | (cyclopropyl-methyl with methyl) |
| 13 | H | Me |
| 14 | H | t-Bu |
| 15 | H | —C(CH$_3$)$_2$CH$_2$CH$_3$ |
| 16 | H | —(CH$_2$)$_6$CH$_3$ |
| 17 | H | (1-phenylcyclopropyl with methyl) |
| 18 | H | (cyclopropyl) |
| 19 | H | (cyclopentyl) |
| 20 | H | (cyclohexyl) |
| 21 | H | (4-piperidinyl) |
| 22 | H | Ph |
| 23 | H | 2-MePh |
| 24 | H | 3-MePh |
| 25 | H | 4-MePh |

TABLE 1-continued

Compounds E13-E91.

[Structure: 4-(acyloxy)phenyl group attached to CH bearing CH2NHR2 and C(=O)NH-isoquinolin-6-yl]

| Example | R2 | R1 |
|---|---|---|
| 26 | H | 2,3-diMePh |
| 27 | H | 2,4-diMePh |
| 28 | H | 2,5-diMePh |
| 29 | H | 3,4-diMePh |
| 30 | H | 3,5-diMePh |
| 31 | H | 2-F—Ph |
| 32 | H | 3-F—Ph |
| 33 | H | 4-F—Ph |
| 34 | H | 2-Me,3-F—Ph |
| 35 | H | 2-Me,4-F—Ph |
| 36 | H | 2-Me,5-F—Ph |
| 37 | H | 4-t-BuPh |
| 38 | H | 2-MeOPh |
| 39 | H | 4-MeOPh |
| 40 | H | 2,4-diMeOPh |
| 41 | H | 2-MeO,4-MePh |
| 42 | H | 2-MeO-5-MePh |
| 43 | H | 3,4-O—CH2—O—Ph |
| 44 | H | 3-PhOPh |
| 45 | H | —CH2-2-MeOPh |
| 46 | H | 2-NH2—Ph |
| 47 | H | 3-NH2—Ph |
| 48 | H | 4-NH2—Ph |
| 49 | H | 3-N(Me2)—Ph |
| 50 | H | 4-N(Me2)—Ph |
| 51 | H | 2-CN—Ph |
| 52 | H | 4-CN—Ph |
| 53 | H | 4-(CH2NH2)—Ph |
| 54 | H | 2-CF3—Ph |
| 55 | H | 2-pyridyl |
| 56 | H | 3-pyridyl |
| 57 | H | 4-pyridyl |
| 58 | H | 2-Me-3-pyridyl |
| 59 | H | 2-Ph—Ph |
| 60 | H | 3-(COPh)—Ph |
| 61 | H | 1-naphthyl |
| 62 | H | benzothiophen-2-yl |
| 63 | H | —CH2NH2 |
| 64 | H | —CH(Ph)CH2NH2 |
| 65 | H | 1-adamantyl |
| 66 | H | 2-adamantyl |
| 67 | H | 2,4-dimethylthiazol-5-yl |
| 68 | H | 4-methylthiazol-5-yl |
| 69 | H | —Bn |
| 70 | H | 4-(CH2NMe2)—Ph |
| 71 | H | 3-oxo-indan-1-yl |
| 72 | H | —CH(Me)Ph |
| 73 | H | —CH2-3,4-diMeOPh |
| 74 | H | —CH2CH2Ph |
| 75 | H | —CH2CH2CH2Ph |
| 76 | H | —CH2-2-MePh |
| 77 | H | —CH2-3-MePh |
| 78 | H | —CH2-4-MePh |
| 79 | H | 1-phenylcyclopentyl |

TABLE 1-continued

Compounds E13-E91.

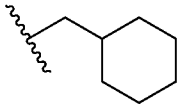 [SMILES: *CC1CCCCC1]

| Example | R₂ | R₁ |
|---|---|---|
| 80 | H | 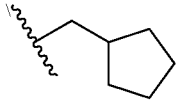 |
| 81 | H | 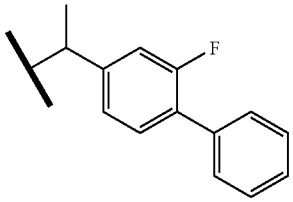 |
| 82 | H | —CH2-4-FPh |
| 83 | H | —CH₂CO₂tBu |
| 84 | H | —CHEtPh |
| 85 | H | —(CH₂)₁₀CH₃ |
| 86 | H | —(CH₂)₇(Z)CH=CH(CH₂)₇CH₃ |
| 87 | H | 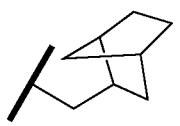 |
| 88 | H | —CH₂CH₂CO₂Me |
| 89 | H | —(E)CH=CHCO₂Me |
| 90 | H |  |
| 91 | H | -3-MeOPh |

TABLE 2

Compounds E92-E122.

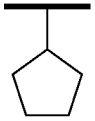

| Example | R₂ | R₁ |
|---|---|---|
| 92 | Me | Me |
| 93 | Me | 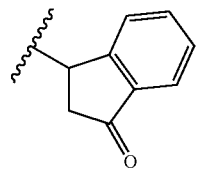 |
| 94 | Me | cyclopentyl |
| 95 | Me | Ph |
| 96 | Me | 2-MePh |
| 97 | Et | 2,5-diMePh |
| 98 | Et | 3,4-diMePh |
| 99 | Et | 2-Me,3-F—Ph |
| 100 | Et | 2-Me,4-F—Ph |
| 101 | Propyl | 2-MeOPh |
| 102 | Et | 2,4-diMeOPh |
| 103 | Me | 3,4-O—CH₂—O— |
| 104 | Allyl | 2-NH₂—Ph |
| 105 | Allyl | 3-NH₂—Ph |
| 106 | H | —CH₂NH₂ |
| 107 | Me | —CH(Ph)CH₂NH₂ |
| 108 | Propyl | —CH(Ph)CH₂NH₂ |
| 109 | Et | —CH(Ph)CH₂NH₂ |
| 110 | Me | Bn |
| 111 | Et | Bn |
| 112 | Allyl | Bn |
| 113 | Me | indanone-yl |
| 114 | Me | —CH(Me)Ph |
| 115 | Et | —CH(Me)Ph |
| 116 | Propyl | —CH(Me)Ph |
| 117 | Me | —CH₂CH₂Ph |
| 118 | Et | —CH₂CH₂CH₂Ph |
| 119 | Me | —CH₂-2-MePh |
| 120 | Me | —CH₂-3-MePh |
| 121 | Me | —CH(Et)Ph |

TABLE 2-continued

Compounds E92-E122.

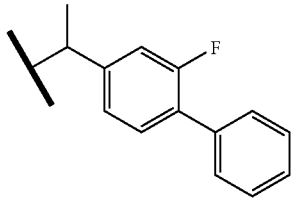

| Example | R₂ | R₁ |
|---------|-----|-----|
| 122 | Me | (4'-phenyl-2'-fluorobiphenyl isopropyl group) |

Examples 123-131

Using commercially available compounds and largely the procedures set forth in Examples 2-12 and substituting the appropriate starting materials, the compounds E123-E131 were made, shown in Table 3.

TABLE 3

Compounds E123-E131.

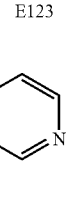

E123 *2HCl
4-(3-amino-1-(isoquinolin-6-ylamino)-1-oxopropan-2-yl)-2-methoxyphenyl benzoate

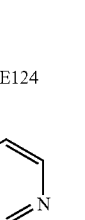

E124 *2HCl
4-(3-amino-1-(isoquinolin-6-ylamino)-1-oxopropan-2-yl)-2-methoxyphenyl pivalate

TABLE 3-continued

Compounds E123-E131.

E125 *2HCl
3-amino-2-(4-hydroxy-3-methoxyphenyl)-N-(isoquinolin-6-yl)propanamide

E126 *2HCl
4-(3-amino-1-(isoquinolin-6-ylamino)-1-oxopropan-2-yl)-2-methylphenyl benzoate

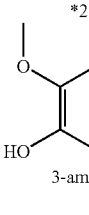

E127 *2HCl
4-(3-amino-1-(isoquinolin-6-ylamino)-1-oxopropan-2-yl)-2-methylphenyl pivalate

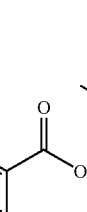

E128 *2HCl
3-amino-2-(4-hydroxy-3-methoxyphenyl)-N-(isoquinolin-6-yl)propanamide

E129 *2HCl
3-(3-amino-1-(isoquinolin-6-ylamino)-1-oxopropan-2-yl)phenyl benzoate

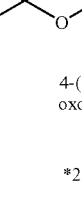

E130 *2HCl
3-(3-amino-1-(isoquinolin-6-ylamino)-1-oxopropan-2-yl)phenyl pivalate

TABLE 3-continued

Compounds E123-E131.

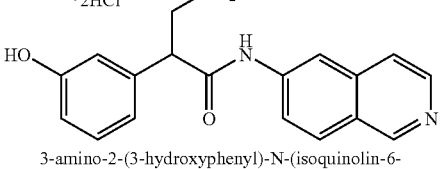

3-amino-2-(3-hydroxyphenyl)-N-(isoquinolin-6-yl)propanamide | E131

Examples 132-139

Figure 7:
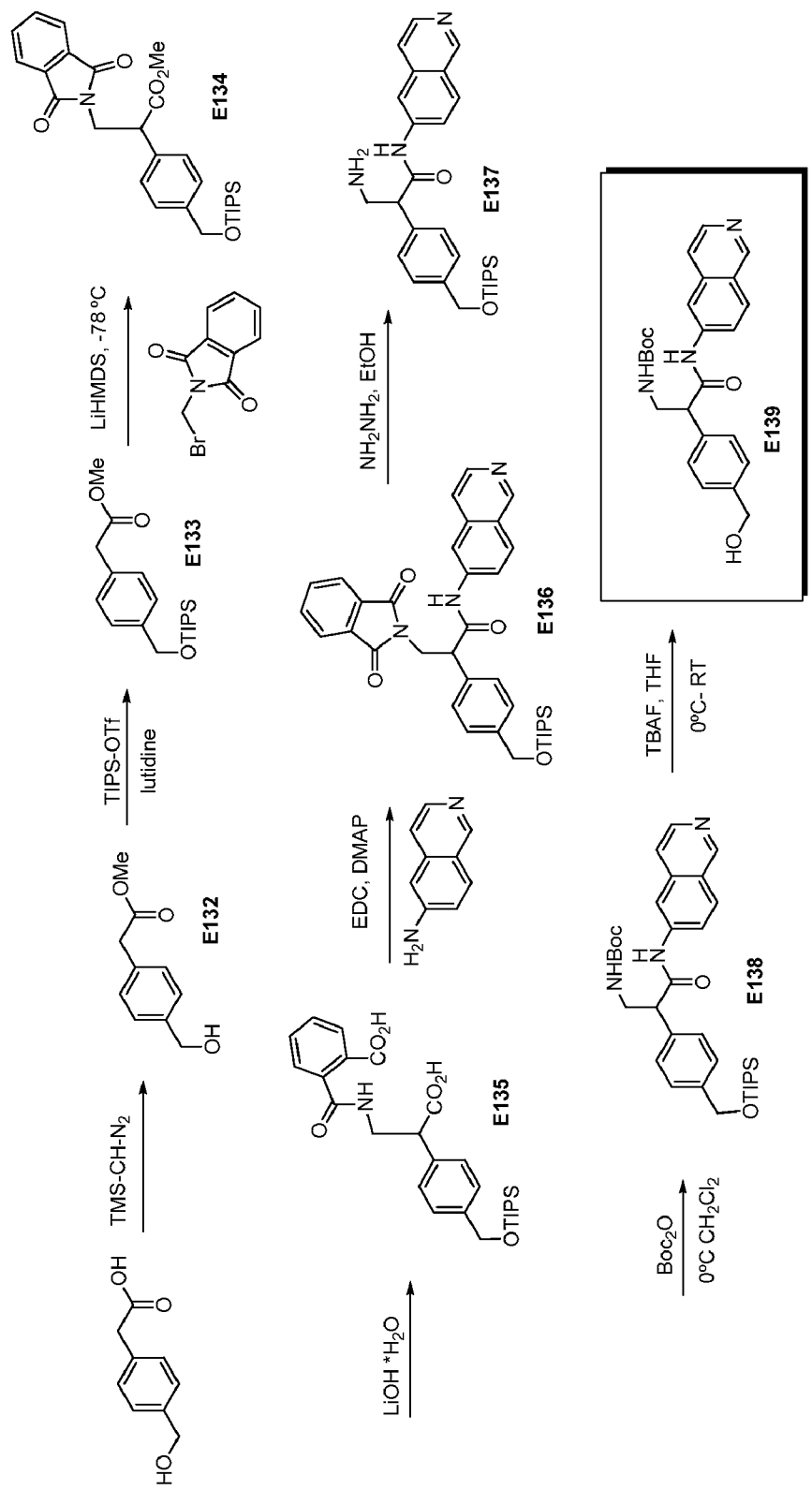
FIG. 7 is a scheme for the synthesis of compounds, including E132-E139.

Compounds E132-E139 were prepared according to the scheme in FIG. 7.

Methyl 2-(4-(hydroxymethyl)phenyl)acetate (E132) was prepared according to the below:

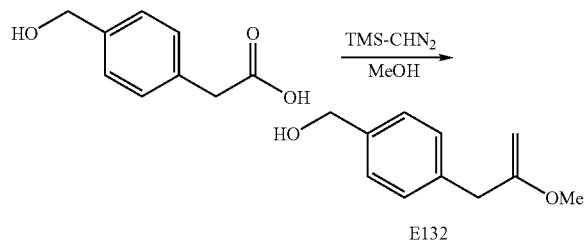

To 2-(4-(hydroxymethyl)phenyl)acetic acid in MeOH at 0° C. was added TMS-CHN₂. The solution was stirred for 3 h then quenched with a few drops of AcOH. The solvents were evaporated. Column chromatography (SiO₂, 3-15% EtOAc/Hex) gave pure methyl 2-(4-(hydroxymethyl)phenyl)acetate (E132).

Methyl 2-(4-((triisopropylsilyloxy)methyl)phenyl)acetate (E133) was prepared from E132 according to the below:

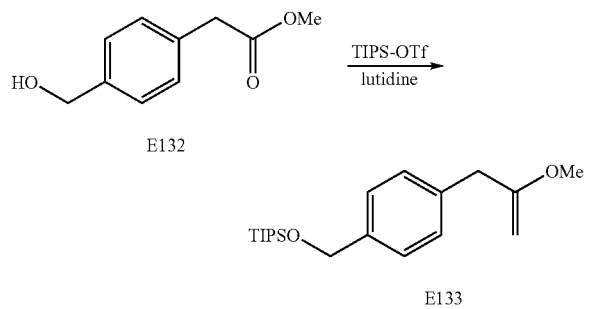

To methyl 2-(4-(hydroxymethyl)phenyl)acetate (E132) in CH₂Cl₂ at 0° C. was added 2,6-lutidine and TIPS-OTf. The ice bath was removed and the solution was allowed to warm to room temperature and stir. After 4 h the solution was poured into NH₄Cl(sat) and CH₂Cl₂ and the organic layer was further extracted with NH₄Cl(sat). The organics were dried (MgSO₄) filtered and evaporated. Column chromatography (SiO₂, 0-15% EtOAc/Hexanes) gave pure methyl 2-(4-((triisopropylsilyloxy)methyl)phenyl)acetate (E133).

Methyl 3-(1,3-dioxoisoindolin-2-yl)-2-(4-((triisopropylsilyloxy)methyl)phenyl)propanoate (E134) was prepared from E133 according to the below:

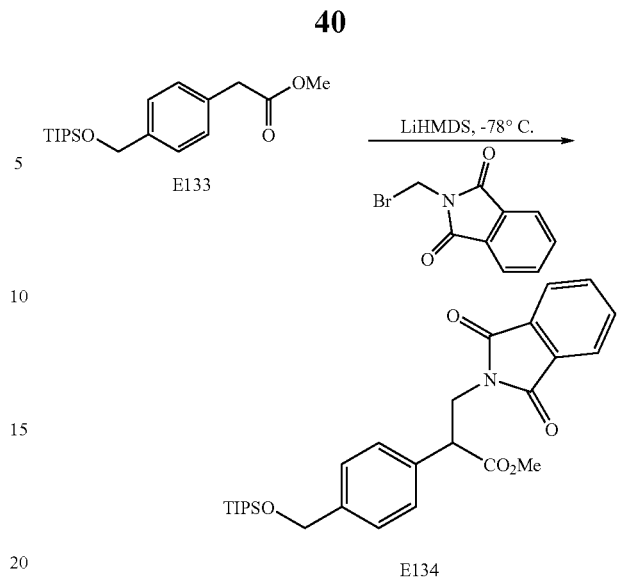

To a solution of LiHMDS in THF cooled to −78° C. was added a cooled solution (−78° C.) of methyl 2-(4-((triisopropylsilyloxy)methyl)phenyl)acetate (E133) in THF via syringe. The solution was stirred at −78° C. for 30 min. Bromo-methyl phthalimide was added directly to the anion and the solution stirred for 2 h at −78° C. The reaction was then poured into NH₄Cl(sat) and extracted with EtOAc. The organics were dried (MgSO₄), filtered, and evaporated. Column chromatography (SiO₂, 0-20% EtOAc/Hexanes) gave pure methyl 3-(1,3-dioxoisoindolin-2-yl)-2-(4-((triisopropylsilyloxy) methyl) phenyl)propanoate (E134).

2-(2-carboxy-2-(4-((triisopropylsilyloxy)methyl)phenyl) ethylcarbamoyl)benzoic acid (E135) was prepared from E134 according to the below:

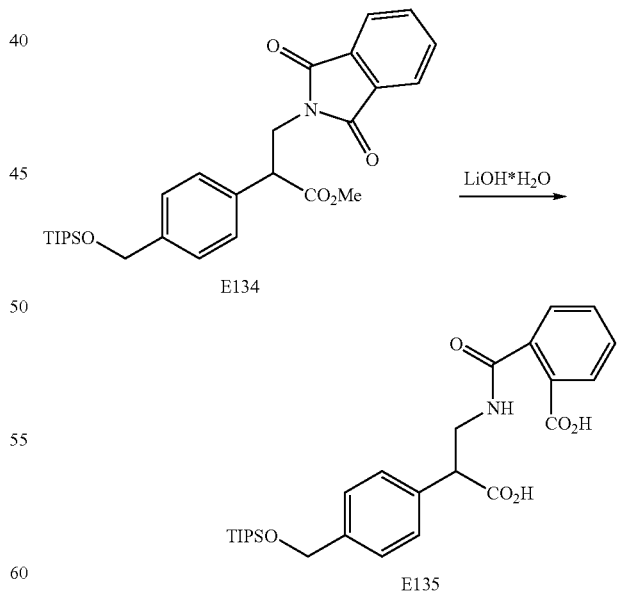

To methyl 3-(1,3-dioxoisoindolin-2-yl)-2-(4-((triisopropylsilyloxy)methyl)phenyl)propanoate (E134) in THF/H₂O was added LiOH.H₂O, and the solution was stirred for 1.5 h or until conversion to product was visible by LC-MS. The solution was then poured into EtOAc/NH₄Cl(sat)/1 N HCl (3:1)

and the aqueous layer was further extracted with EtOAc. The organics were dried (MgSO₄), filtered, and evaporated to give crude 2-(2-carboxy-2-(4-((triisopropylsilyloxy)methyl)phenyl)ethylcarbamoyl)benzoic acid (E135).

3-(1,3-dioxoisoindolin-2-yl)-N-(isoquinolin-6-yl)-2-(4-((triisopropylsilyloxy)methyl)phenyl)propanamide (E136) was prepared from E135 according to the below:

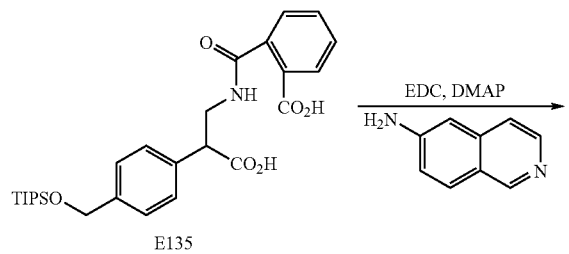

E135

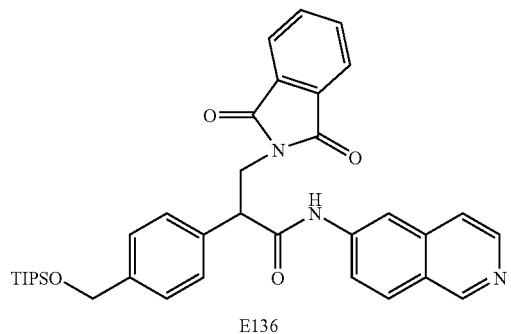

E136

To 2-(2-carboxy-2-(4-((triisopropylsilyloxy)methyl)phenyl)ethylcarbamoyl)benzoic acid (E135) in pyridine was added EDC, DMAP and 6-aminoisoquinoline and the solution was flushed with N₂, capped, and stirred overnight. The mixture was poured into EtOAc/NaHCO₃(sat) and the aqueous layer was further extracted with EtOAc. The organics were dried (MgSO₄), filtered, and evaporated. Column chromatography (SiO₂, 5% MeOH/CH₂Cl₂) gave pure 3-(1,3-dioxoisoindolin-2-yl)-N-(isoquinolin-6-yl)-2-(4-((triisopropylsilyloxy)methyl)phenyl)propanamide (E136).

3-amino-N-(isoquinolin-6-yl)-2-(4-((triisopropylsilyloxy)methyl)phenyl)propanamide (E137) was prepared from E136 according to the below:

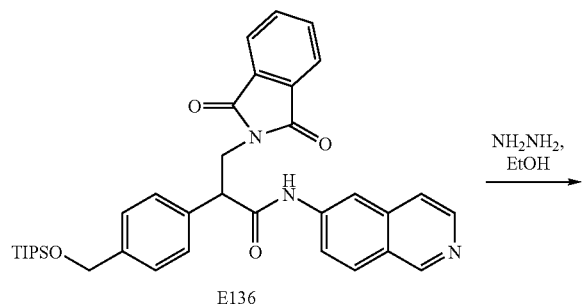

E136

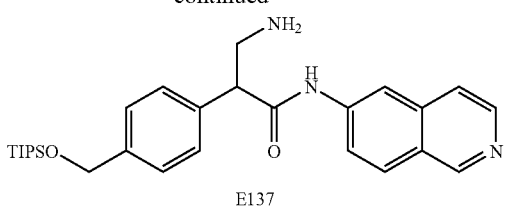

E137

To 3-(1,3-dioxoisoindolin-2-yl)-N-(isoquinolin-6-yl)-2-(4-((triisopropylsilyloxy)methyl)phenyl)propanamide (E136) in EtOH was added NH₂—NH₂ and the solution was refluxed for 1.2-2 h. The solids were filtered, and the solvents were evaporated. Column chromatography (SiO₂, 5% 2N NH₃-MeOH/CH₂Cl₂) gave pure 3-amino-N-(isoquinolin-6-yl)-2-(4-((triisopropylsilyloxy)methyl)phenyl)propanamide (E137).

Tert-butyl 3-(isoquinolin-6-ylamino)-3-oxo-2-(4-((triisopropylsilyloxy)methyl)phenyl)propylcarbamate (E138) was prepared from E137 according to the below:

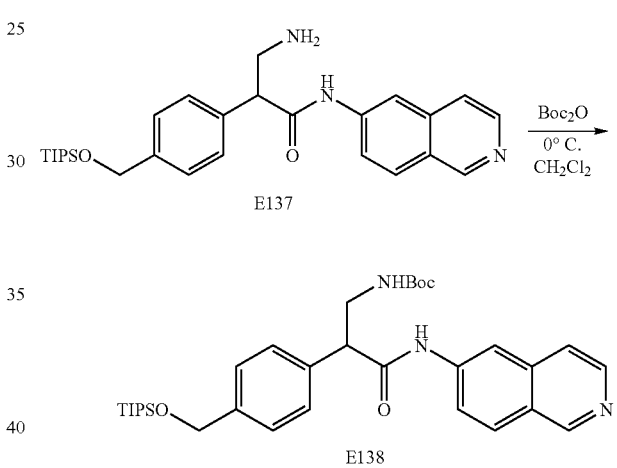

To 3-amino-N-(isoquinolin-6-yl)-2-(4-((triisopropylsilyloxy)methyl)phenyl)propanamide (E137) in CH₂Cl₂ at 0° C. was added a solution of Boc₂O in CH₂Cl₂ also cooled to 0° C. before addition. The solution was stirred for 30 min at 0° C. and additional Boc₂O was added and the solution was stirred for 30 min more then poured into CH₂Cl₂/NaHCO₃(sat). The aqueous layers were further extracted with CH₂Cl₂, dried (MgSO₄), filtered, and evaporated. Column chromatography (SiO₂, 3% MeOH/CH₂Cl₂) gave tert-butyl 3-(isoquinolin-6-ylamino)-3-oxo-2-(4-((triisopropylsilyloxy)methyl)phenyl)propylcarbamate (E138).

Tert-butyl 2-(4-(hydroxymethyl)phenyl)-3-(isoquinolin-6-ylamino)-3-oxopropylcarbamate (E139).

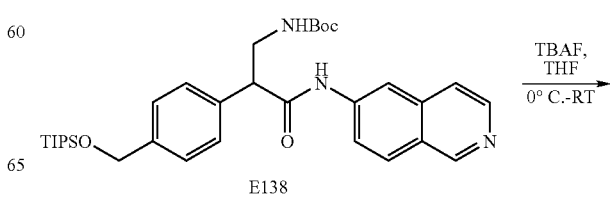

E138

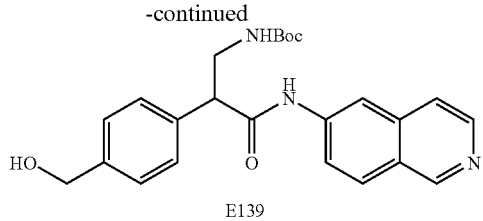

E139

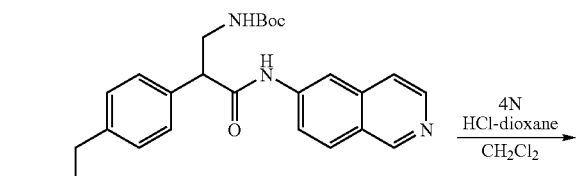

E140

To tert-butyl 3-(isoquinolin-6-ylamino)-3-oxo-2-(4-((triisopropylsilyloxy)methyl)phenyl)propylcarbamate (E138) in THF at 0° C. was added TBAF, and the solution was stirred for 45 min at 0° C. The compound was poured into EtOAc and washed with NH₄Cl(sat), dried (MgSO₄), filtered, and evaporated. Column chromatography (SiO₂, 6% MeOH/CH₂Cl₂) gave pure tert-butyl 2-(4-(hydroxymethyl)phenyl)-3-(isoquinolin-6-ylamino)-3-oxopropylcarbamate (E139).

Examples 140-143

Figure 8:
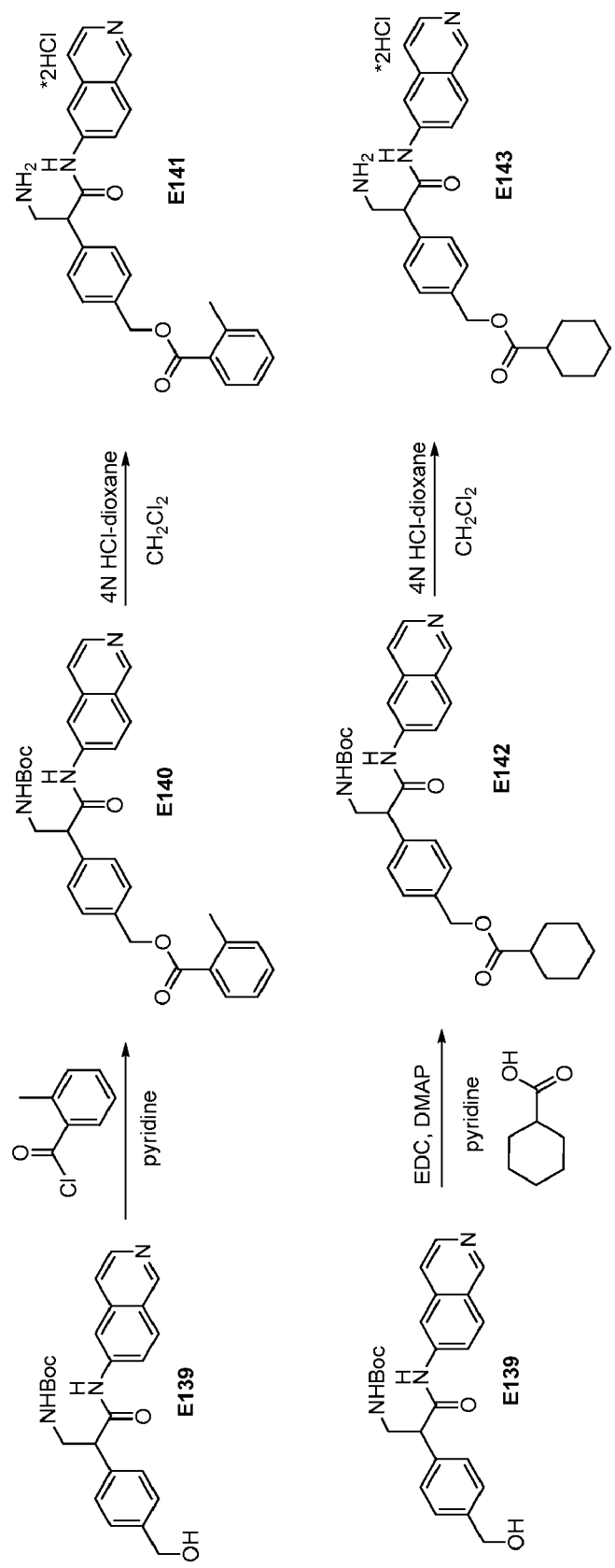
FIG. 8 is a scheme for the synthesis of compounds, including E140-E143.

Compounds E140-E143 were prepared according to the scheme in FIG. 8.

4-(3-(tert-butoxycarbonylamino)-1-(isoquinolin-6-ylamino)-1-oxopropan-2-yl)benzyl 2-methylbenzoate (E140) was prepared from E139 according to the below:

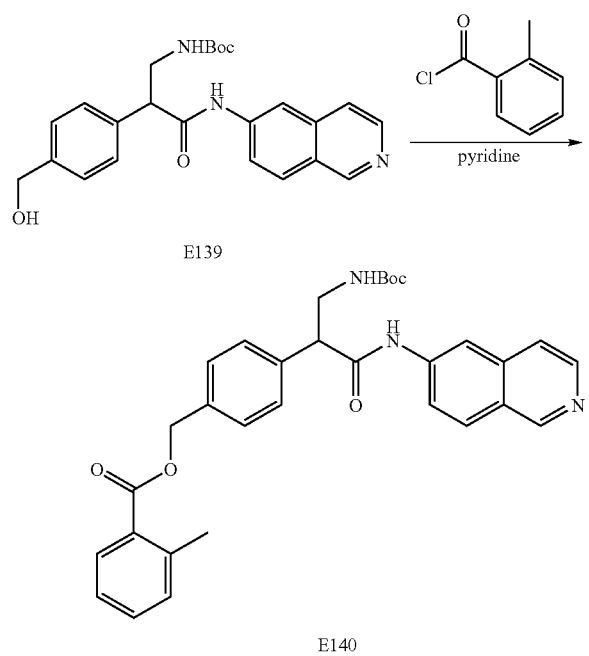

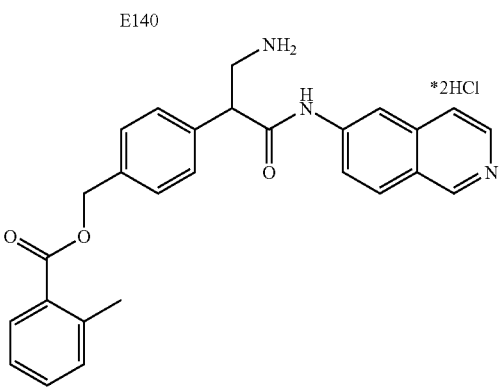

E141

To 4-(3-(tert-butoxycarbonylamino)-1-(isoquinolin-6-ylamino)-1-oxopropan-2-yl)benzyl 2-methylbenzoate (E140) in CH₂Cl₂ was added HCl (4N in dioxane) and the solution was stirred for 8-10 h. The solvents were evaporated to give pure 4-(3-amino-1-(isoquinolin-6-ylamino)-1-oxopropan-2-yl)benzyl 2-methylbenzoate dihydrochloride (E141).

4-(3-(tert-butoxycarbonylamino)-1-(isoquinolin-6-ylamino)-1-oxopropan-2-yl)benzyl cyclohexanecarboxylate (E142) was prepared from E139 according to the below:

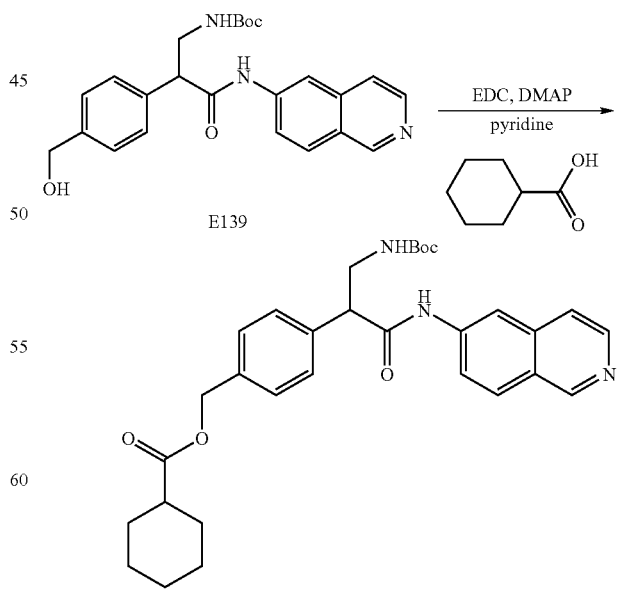

E142

To tert-butyl 2-(4-(hydroxymethyl)phenyl)-3-(isoquinolin-6-ylamino)-3-oxopropylcarbamate (E139) in pyridine was added 2-methylbenzoyl chloride and the solution was stirred for 2 h at room temperature. The mixture was poured into NaHCO₃ and extracted with EtOAc. The organics were dried (MgSO₄), filtered, and evaporated. Column chromatography (SiO₂, 5% MeOH/CH₂Cl₂) gave pure 4-(3-(tert-butoxycarbonylamino)-1-(isoquinolin-6-ylamino)-1-oxopropan-2-yl) benzyl 2-methylbenzoate (E140).

4-(3-amino-1-(isoquinolin-6-ylamino)-1-oxopropan-2-yl) benzyl 2-methylbenzoate dihydrochloride (E141) was prepared from E140 according to the below:

To tert-butyl 2-(4-(hydroxymethyl)phenyl)-3-(isoquinolin-6-ylamino)-3-oxopropylcarbamate (E139) in pyridine was added EDC, DMAP, and cyclohexanecarboxylic acid, and the solution was flushed with N₂, capped, and stirred overnight. The mixture was poured into EtOAc/NaHCO₃(sat) and the aqueous layer was further extracted with EtOAc. The organics were dried (MgSO₄), filtered, and evaporated. Column chromatography (SiO₂, 5% MeOH/CH₂Cl₂) gave pure 4-(3-(tert-butoxycarbonylamino)-1-(isoquinolin-6-ylamino)-1-oxopropan-2-yl)benzyl cyclohexanecarboxylate (E142).

4-(3-amino-1-(isoquinolin-6-ylamino)-1-oxopropan-2-yl)benzyl cyclohexanecarboxylate dihydrochloride (E143) was prepared from E142 according to the below:

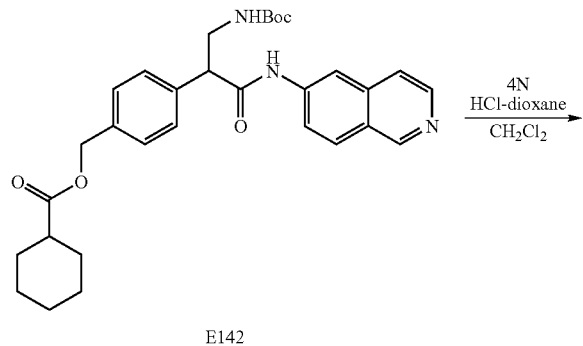

To 4-(3-(tert-butoxycarbonylamino)-1-(isoquinolin-6-ylamino)-1-oxopropan-2-yl)benzyl cyclohexanecarboxylate (E142) in CH₂Cl₂ was added HCl (4 N in dioxane) and the solution was stirred for 8-10 h. The solvents were evaporated to give pure 4-(3-amino-1-(isoquinolin-6-ylamino)-1-oxopropan-2-yl)benzyl cyclohexanecarboxylate dihydrochloride (E143).

Example 144

3-amino-2-(4-(hydroxymethyl)phenyl)-N-(isoquinolin-6-yl)propanamide dihydrochloride (E144) was prepared from E139 according to the below:

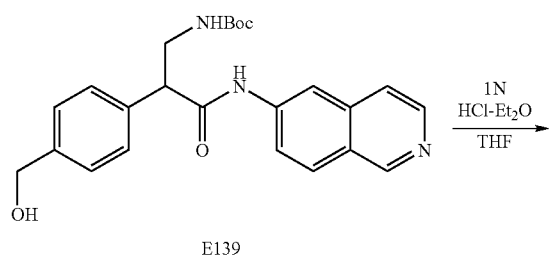

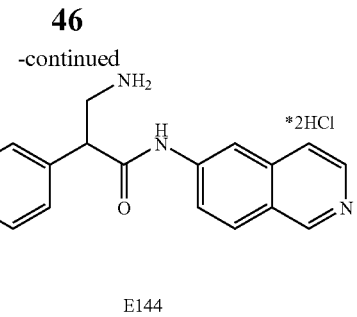

To tert-butyl 2-(4-(hydroxymethyl)phenyl)-3-(isoquinolin-6-ylamino)-3-oxopropylcarbamate (E139) in THF and water and cooled to 0° C. was added HCl (1 N in Et₂O). After 30 min the mixture was warmed to room temperature and the solution was stirred for 48 h. 2 M NH₃ in MeOH was added. The solvents were evaporated and the mixture purified by column chromatography (SiO₂, 0-5-10% (2 M NH₃ in MeOH)/CH₂Cl₂). The compound was dissolved in DCM/MeOH and 1 N HCl in Et₂O added. The solvents were evaporated to give pure 3-amino-2-(4-(hydroxymethyl)phenyl)-N-(isoquinolin-6-yl)propanamide dihydrochloride (E144).

Examples 145-148

Figure 9:
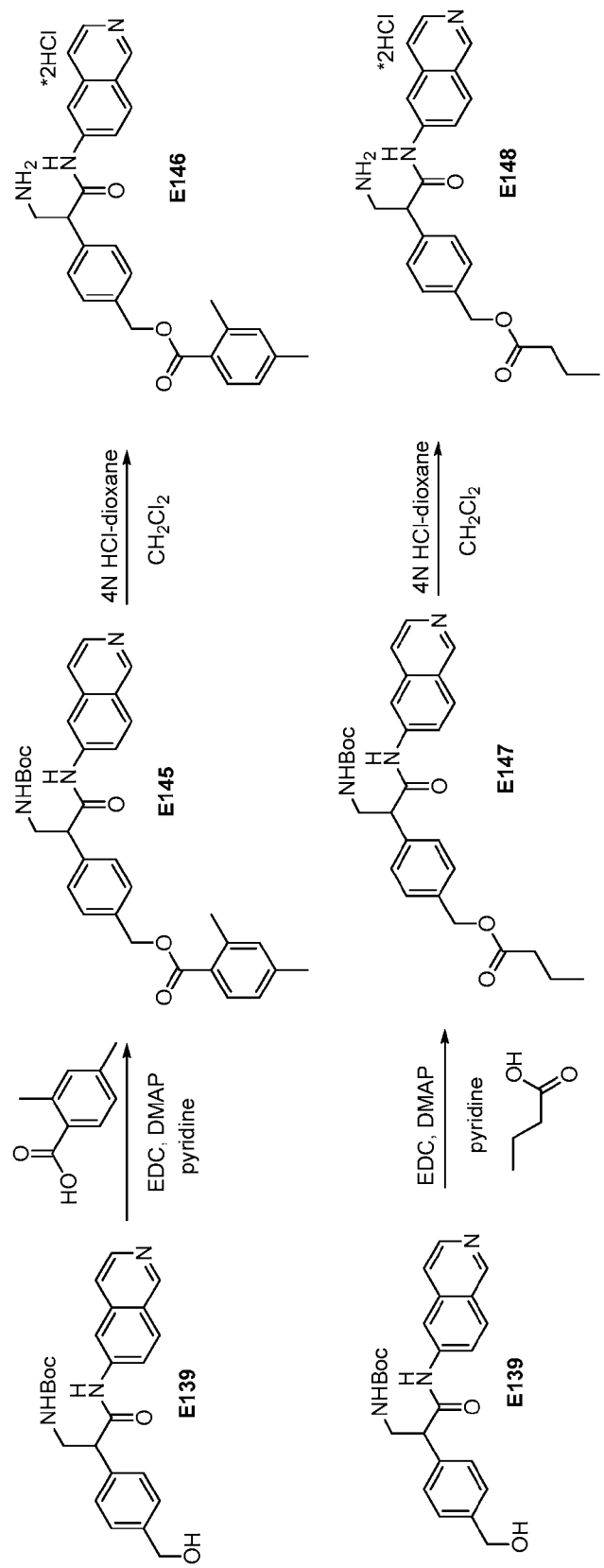
FIG. 9 is a scheme for the synthesis of compounds, including E145-E148.

Compounds E145-E148 were prepared according to the scheme in FIG. 9.

4-(3-(tert-butoxycarbonylamino)-1-(isoquinolin-6-ylamino)-1-oxopropan-2-yl)benzyl 2,4-dimethylbenzoate (E145) was prepared E139 according to the below:

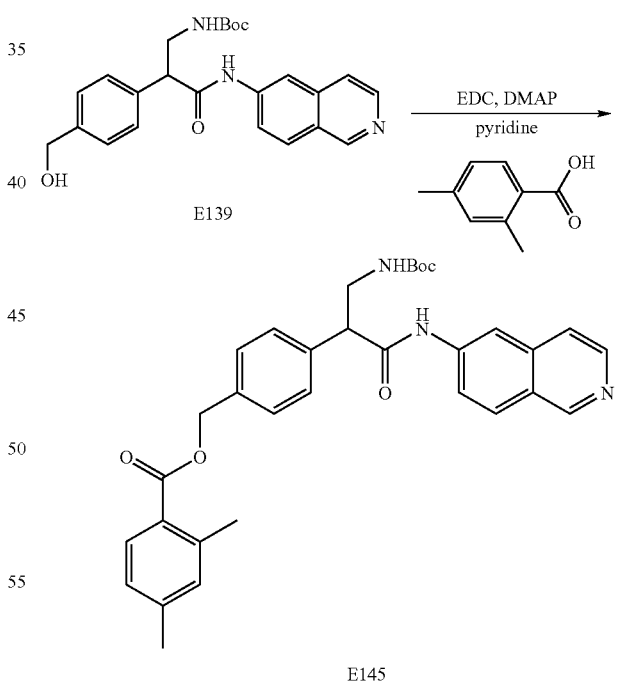

To 2,4-dimethylbenzoic acid in pyridine was added EDC, DMAP, and tert-butyl 2-(4-(hydroxymethyl)phenyl)-3-(isoquinolin-6-ylamino)-3-oxopropylcarbamate (E139), and the solution was capped and stirred overnight. The mixture was poured into EtOAc/NaHCO₃(sat) and the aqueous layer was further extracted with EtOAc. The organics were dried (MgSO₄), filtered, and evaporated. Column chromatography (SiO$_2$, 0-5% MeOH/CH$_2$Cl$_2$ gradient) gave pure 4-(3-(tert-butoxycarbonylamino)-1-(isoquinolin-6-ylamino)-1-oxopropan-2-yl)benzyl 2,4-dimethylbenzoate (E145).

4-(3-amino-1-(isoquinolin-6-ylamino)-1-oxopropan-2-yl) benzyl 2,4-dimethylbenzoate dihydrochloride (E146) was prepared from E145 according to the below:

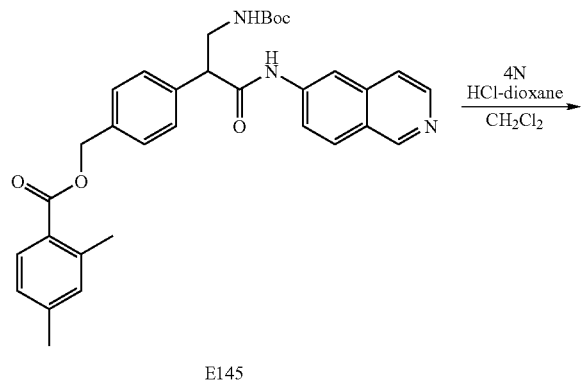

E145

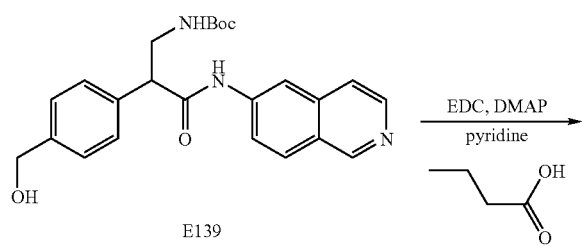

E146

To 4-(3-(tert-butoxycarbonylamino)-1-(isoquinolin-6-ylamino)-1-oxopropan-2-yl)benzyl 2,4-dimethylbenzoate (E145) in CH$_2$Cl$_2$ was added HCl (4 N in dioxane) and the solution was stirred for 8-10 h. The solvents were evaporated to give pure 4-(3-amino-1-(isoquinolin-6-ylamino)-1-oxopropan-2-yl)benzyl 2,4-dimethylbenzoate dihydrochloride (E146).

4-(3-(tert-butoxycarbonylamino)-1-(isoquinolin-6-ylamino)-1-oxopropan-2-yl)benzyl butyrate (E148) was prepared from E139 according to the below:

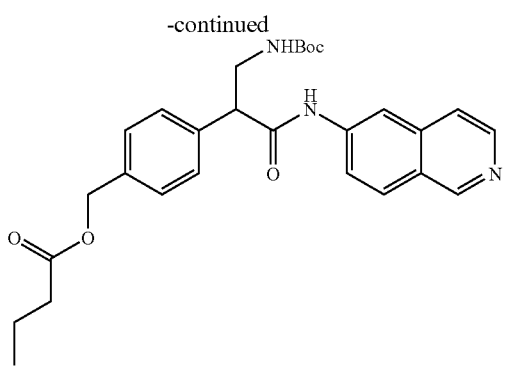

-continued

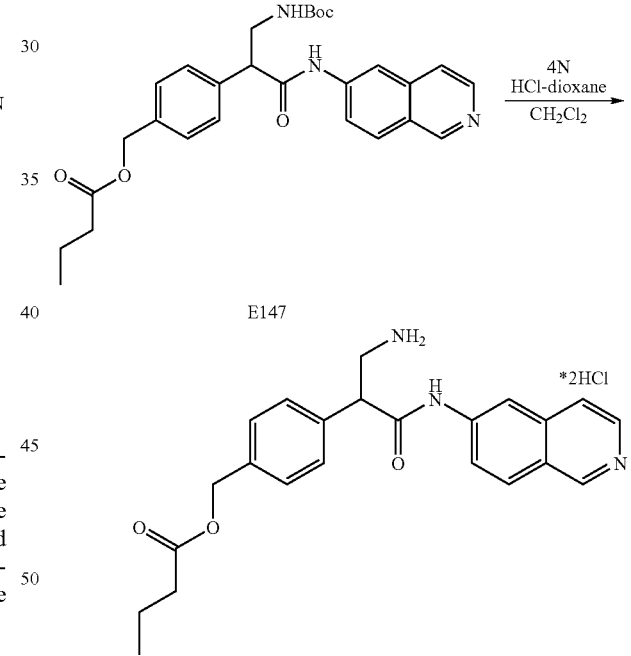

E148

To butyric acid in pyridine was added EDC, DMAP, and tert-butyl 2-(4-(hydroxymethyl)phenyl)-3-(isoquinolin-6-ylamino)-3-oxopropylcarbamate (E139), and the solution was capped and stirred overnight. The mixture was poured into EtOAc/NaHCO$_{3(sat)}$ and the aqueous layer was further extracted with EtOAc. The organics were dried (MgSO$_4$), filtered, and evaporated. Column chromatography (SiO$_2$, 0-5% MeOH/CH$_2$Cl$_2$ gradient) gave pure 4-(3-(tert-butoxycarbonylamino)-1-(isoquinolin-6-ylamino)-1-oxopropan-2-yl)benzyl butyrate (E148).

4-(3-amino-1-(isoquinolin-6-ylamino)-1-oxopropan-2-yl) benzyl butyrate dihydrochloride (E148) was prepared from E147 according to the below:

To 4-(3-(tert-butoxycarbonylamino)-1-(isoquinolin-6-ylamino)-1-oxopropan-2-yl)benzyl butyrate (E147) in CH$_2$Cl$_2$ was added HCl (4 N in dioxane) and the solution was stirred for 8-10 h The solvents were evaporated to give pure 4-(3-amino-1-(isoquinolin-6-ylamino)-1-oxopropan-2-yl) benzyl butyrateate dihydrochloride (E148).

Examples 149-175

Using commercially available compounds and largely the procedures set forth in Examples 140-143 and substituting the appropriate starting materials, the compounds E149-E175 have been made, shown in Table 4.

TABLE 4

Compounds E149-E175.

| Example | R |
|---|---|
| 149 | 2-phenyl-2-methylpropan-2-yl (cumyl-like, C(CH₃)₂Ph with extra methyl) |
| 150 | -iPr |
| 151 | -tBu |
| 152 | —(CH₂)₆CH₃ |
| 153 | adamantyl-methyl |
| 154 | long unsaturated alkyl chain (oleyl-type) |
| 155 | —CH₂-cyclohexyl |
| 156 | -Ph |
| 157 | -Bn |
| 158 | —CH₂CH₂Ph |
| 159 | —CH₂—OPh |
| 160 | 1-phenylcyclohexyl |
| 161 | 3,5-diMePh |
| 162 | (1-methylcyclopropyl)methyl-cyclopropyl |
| 163 | —(CH₂)₁₀CH₃ |
| 164 | —CH₂CH₂-cyclohexyl |

TABLE 4-continued

Compounds E149-E175.

[Structure: R-C(=O)-O-CH2-(phenyl)-CH(CH2NH2)-C(=O)-NH-(isoquinolin-6-yl) *X—HCl]

| Example | R |
|---|---|
| 165 | 3-MeOPh |
| 166 | 4-MeOPh |
| 167 | 2,4-diOMePh |
| 168 | 3,4-O—CH₂—O—Ph |
| 169 | cyclopentyl |
| 170 | —CHPh₂ |
| 171 | 2-Ph—Ph |
| 172 | 1-phenylcyclopentyl |
| 173 | 2-methylbenzyl (CH(CH₃)-(2-methylphenyl)) |
| 174 | 1-(naphthalen-2-yl)ethyl |
| 175 | 1-adamantyl |

Examples 176-196

Using commercially available compounds and largely the procedures set forth in Examples 140-143 and substituting the appropriate starting materials, the compounds E176-E196, could be made, shown in Table 5.

TABLE 5

Compounds E176-E196.

| Example | R |
|---|---|
| 176 | 2-MeOPh |
| 177 | 4-NHMePh |
| 178 | 4-NMe$_2$Ph |
| 179 | 4-OEtPh |
| 180 | 3-MePh |
| 181 | 4-MePh |
| 182 | 2,3-diMePh |
| 183 | 2,6-MePh |
| 184 | 3,4-MePh |
| 185 | (indanyl) |
| 186 | 2-ClPh |
| 187 | 3-ClPh |
| 188 | 4-ClPh |
| 189 | 2-FPh |
| 190 | 3-FPh |
| 191 | 4-FPh |
| 192 | 2,4-diClPh |
| 193 | 2,4-diFPh |
| 194 | (4-methoxybenzyl) |
| 195 | (2,4-dimethylbenzyl) |
| 196 | (2,3-difluorobenzyl) |

Example 197

Figure 10:
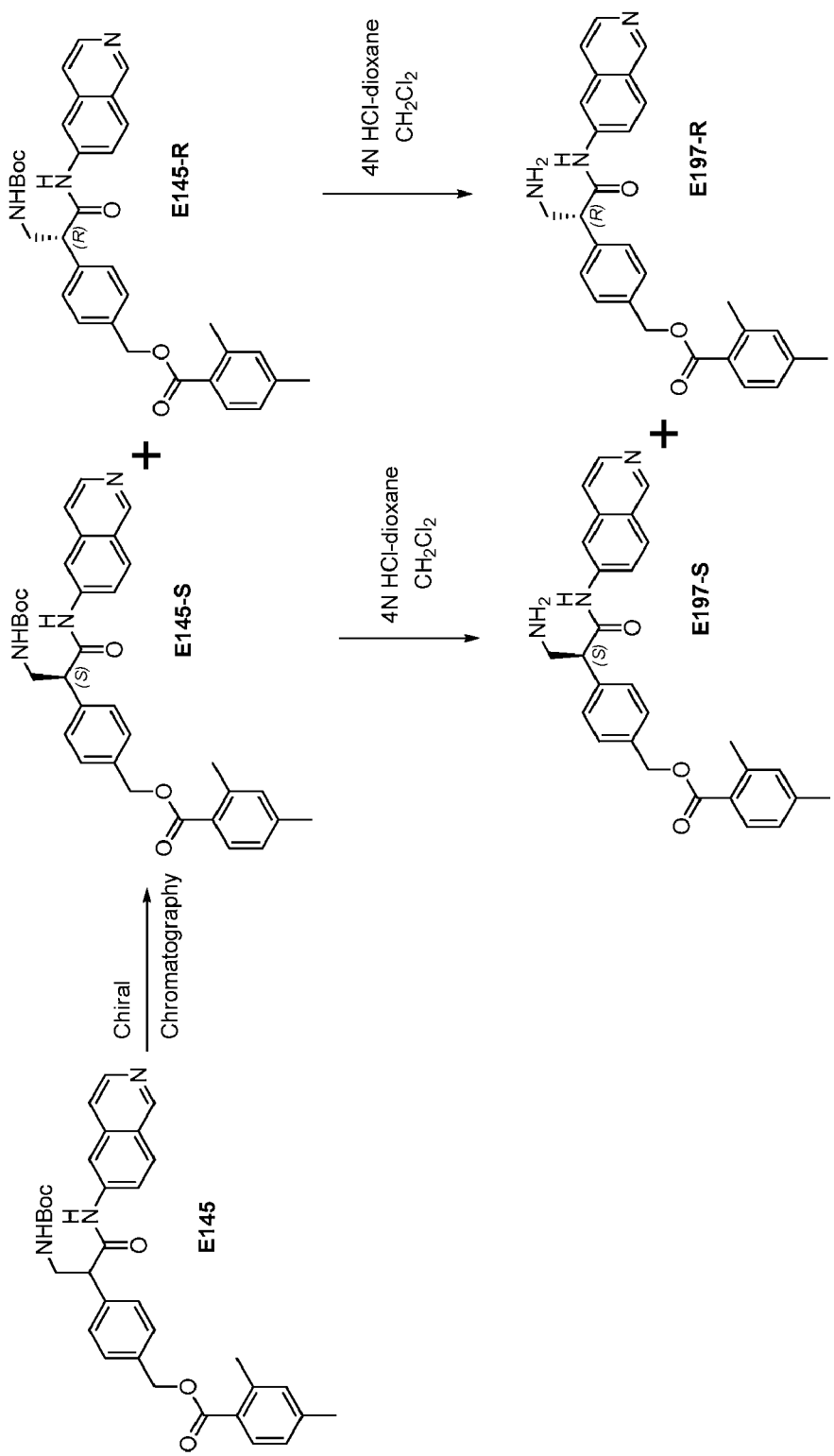
FIG. 10 is a scheme for the synthesis of compounds, including E197-S and E197-R.

(S)-4-(3-(tert-butoxycarbonylamino)-1-(isoquinolin-6-ylamino)-1-oxopropan-2-yl)benzyl 2,4-dimethylbenzoate (E145-S) and (R)-4-(3-(tert-butoxycarbonylamino)-1-(isoquinolin-6-ylamino)-1-oxopropan-2-yl)benzyl 2,4-dimethylbenzoate (E145-R) were prepared from E145 according to the scheme in FIG. 10. 4-(3-(tert-butoxycarbonylamino)-1-(isoquinolin-6-ylamino)-1-oxopropan-2-yl)benzyl 2,4-dimethylbenzoate was dissolve in methanol and the R and S enantiomers separated by supercritical fluid chromatography (Chiralpak AS-H column, eluent: 18.8% MeOH, 0.2% dimethylethylamine, 80% CO$_2$). The enantiomers were then each purified by column chromotagraphy (SiO$_2$, 0-5% MeOH/CH$_2$Cl$_2$gradient). The enantiomeric excess for each enantiomer was >98%.

(S)-4-(3-amino-1-(isoquinolin-6-ylamino)-1-oxopropan-2-yl)benzyl 2,4-dimethylbenzoate dihydrochloride (E197-S) was prepared from E145-S according to the scheme in FIG. 6. To (S)-4-(3-(tert-butoxycarbonylamino)-1-(isoquinolin-6-ylamino)-1-oxopropan-2-yl)benzyl 2,4-dimethylbenzoate (E145-S) in CH$_2$Cl$_2$ was added HCl (4 N in dioxane) and the solution was stirred for 8-10 h. The solvents were evaporated to give pure (S)-4-(3-amino-1-(isoquinolin-6-ylamino)-1-oxopropan-2-yl)benzyl 2,4-dimethylbenzoate dihydrochloride (E197-S). Analysis by chiral HPLC (Chiralpak AS-H, eluent: 90:10:0.1 EtOH:H$_2$O:diethylamine) showed enantiomeric excess >98%.

(R)-4-(3-amino-1-(isoquinolin-6-ylamino)-1-oxopropan-2-yl)benzyl 2,4-dimethylbenzoate dihydrochloride (E197-R) was prepared from E145-R according to the scheme in FIG. 6. To (S)-4-(3-(tert-butoxycarbonylamino)-1-(isoquinolin-6-ylamino)-1-oxopropan-2-yl)benzyl 2,4-dimethylbenzoate (E145-R) in CH$_2$Cl$_2$ was added HCl (4 N in dioxane) and the solution was stirred for 8-10 h. The solvents were evaporated to give pure (R)-4-(3-amino-1-(isoquinolin-6-ylamino)-1-oxopropan-2-yl)benzyl 2,4-dimethylbenzoate dihydrochloride (E197-R). Analysis by chiral HPLC (Chiralpak AS-H, eluent:90:10:0.1 EtOH:H$_2$O:diethylamine) showed enantiomeric excess >98%.

Examples 198-203

Figure 11:
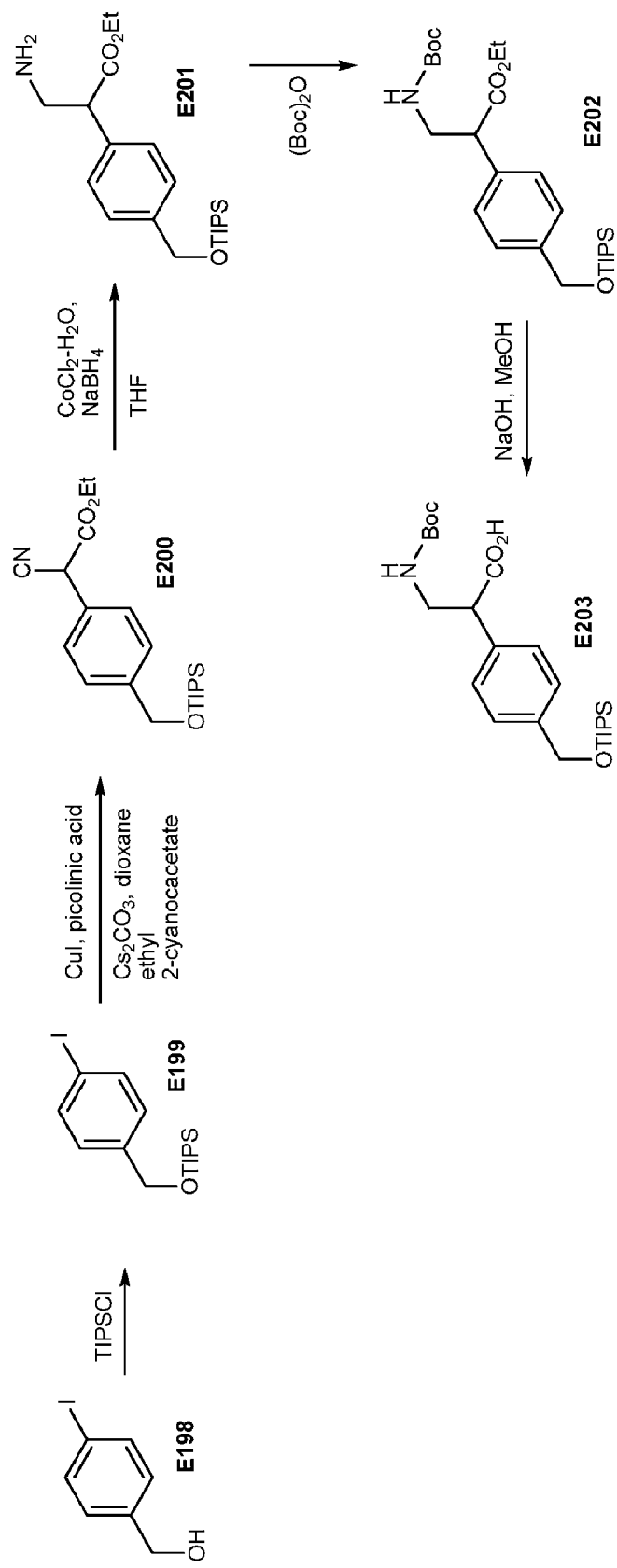
FIG. 11 is a scheme for the synthesis of compounds, including E199-E203.

Compounds E199-E203 were prepared according to the scheme in FIG. 11.

(4-iodobenzyloxy)triisopropylsilane (E199) was prepared from E198 according to the below:

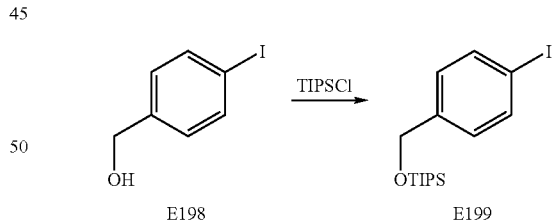

To a solution of (4-iodophenyl)methanol (E198) and imidazole in CH$_2$Cl$_2$ at 0° C. was added dropwise TIPSCl. The reaction mixture was stirred overnight. The solution was quenched with H$_2$O and the CH$_2$Cl$_2$ layer separated. The organic layer was further washed with 0.5N HCl and NaHCO$_{3(sat)}$. The combined organic layers were dried (MgSO$_4$), filtered, and evaporated. The crude yellow oil, (4-iodobenzyloxy)triisopropylsilane (E199), was used directly in the next step.

Ethyl 2-cyano-2-(4-((triisopropylsilyloxy)methyl)phenyl) acetate (E200) was prepared from E199 according to the below:

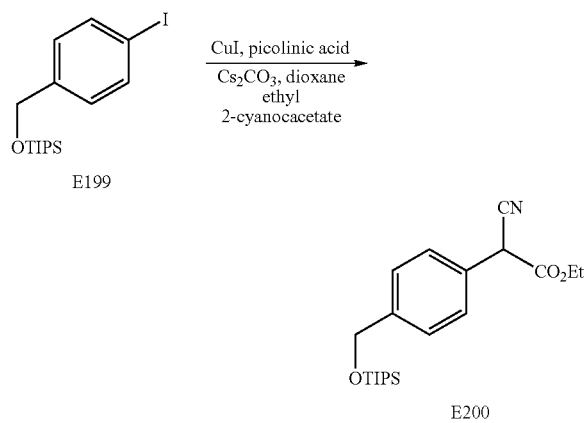

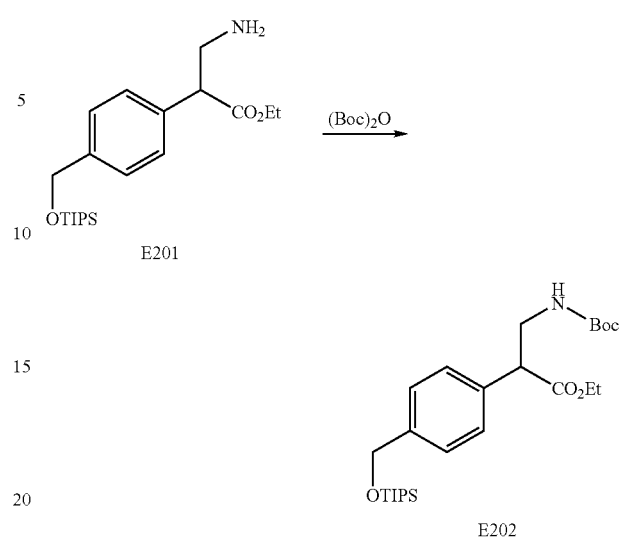

To a solution of ethyl 2-cyanoacetate and (4-iodobenzyloxy) triisopropylsilane (E199) in dioxane were added $Cs_2CO_3$, CuI, and picolinic acid. The mixture was stirred overnight at 90° C. The solid was removed by filtration and the dioxane concentrated under reduced pressure. Column chromatography ($SiO_2$, hexane:ethyl acetate 25:1) gave pure ethyl 2-cyano-2-(4-((triisopropylsilyloxy)methyl)phenyl)acetate (E200) as a yellow oil.

Ethyl 3-amino-2-(4-((triisopropylsilyloxy)methyl)phenyl) propanoate (E201) was prepared from E200 according to the below:

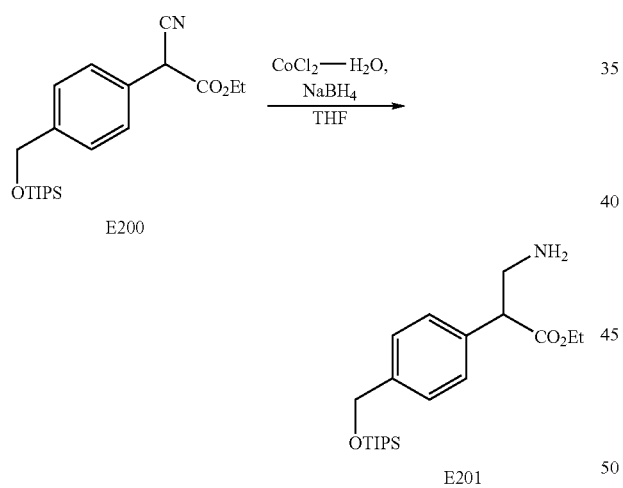

To a suspension of $CoCl_2.6H_2O$ in THF was added ethyl 2-cyano-2-(4-((triisopropylsilyloxy)methyl)phenyl)acetate (E200). The mixture was cooled to 0° C. and $NaBH_4$ was added to the mixture in several portions over 30 min. The mixture was stirred at room temperature for 4 h. The reaction was quenched with water. The mixture was filtered and the filtrate extracted twice with ether. The organics were dried ($MgSO_4$), filtered, and evaporated. Column chromatography ($SiO_2$, DCM:EtOH=50:1) gave pure ethyl 3-amino-2-(4-((triisopropylsilyloxy)methyl)phenyl)propanoate (E201) as a yellow oil.

Ethyl 3-(tert-butoxycarbonylamino)-2-(4-((triisopropylsilyloxy)methyl)phenyl)propanoate (E202) was prepared from E201 according to the below:

To a solution of ethyl 3-amino-2-(4-((triisopropylsilyloxy) methyl)phenyl)propanoate (E201) in DCM was added $(Boc)_2O$ and triethylamine. The mixture was stirred for 2 h, then washed with 0.5 N HCl and $NaHCO_{3(sat)}$. The organic layer was dried ($MgSO_4$) and concentrated to give ethyl 3-(tert-butoxycarbonylamino)-2-(4-((triisopropylsilyloxy) methyl)phenyl)propanoate (E202).

3-(tert-butoxycarbonylamino)-2-(4-((triisopropylsilyloxy)methyl)phenyl)propanoic acid (E203) was prepared from E202 according to the below:

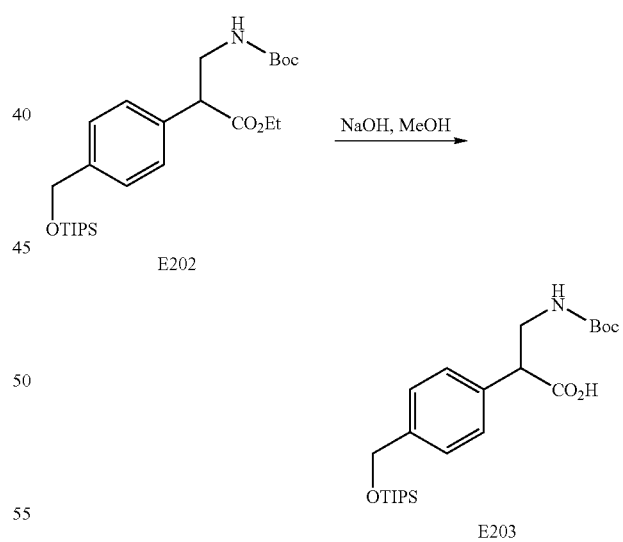

To a solution of ethyl 3-(tert-butoxycarbonylamino)-2-(4-((triisopropylsilyloxy)methyl)phenyl)propanoate (E202) in methanol was added dropwise 4 N NaOH. The mixture was stirred for 2 h, adjusted the pH to 7 with 2 N HCl, and extracted with ethyl acetate. The combined organic layers were washed with 0.5 N HCl and brine, dried ($MgSO_4$), and concentrated in vacuo to afford 3-(tert-butoxycarbonylamino)-2-(4-((trisopropylsilyloxy)methyl)phenyl)propanoic acid (E203) as white solid.

Examples 204-206

Figure 12:
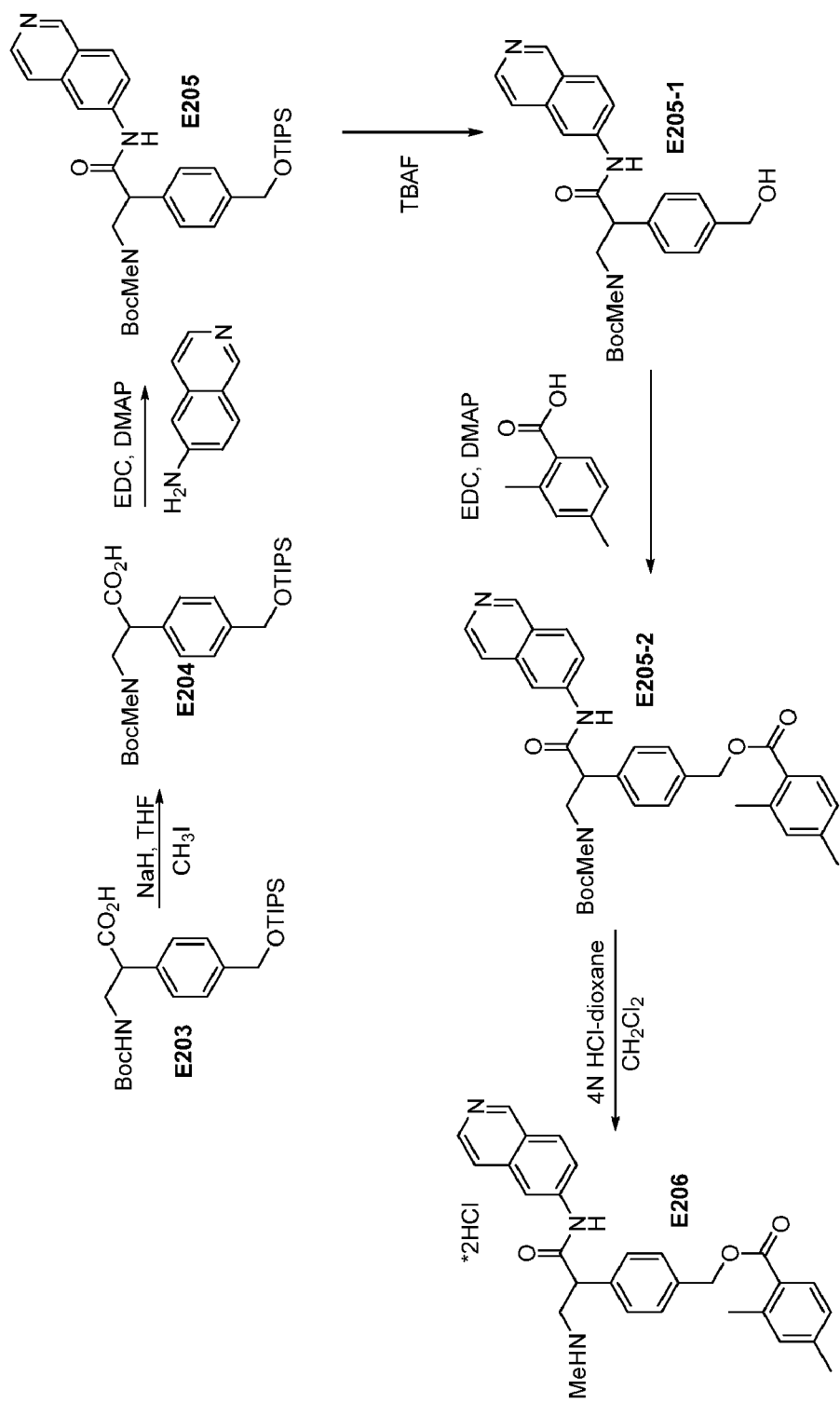
FIG. 12 is a scheme for the synthesis of compounds, including E204-E206.

Compounds E204-E206 were prepared according to the scheme in FIG. 12, which is a modified procedure by Cheung, S. T. et al. *Can. J. Chem.* 1977, 55, 906-910.

3-(tert-butoxycarbonyl(methyl)amino)-2-(4-((triisopropylsilyloxy)methyl)phenyl)propanoic acid (E204) was prepared from E203 according to the below:

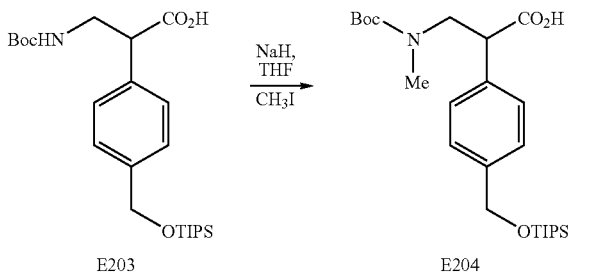

To 3-(tert-butoxycarbonylamino)-2-(4-((triisopropylsilyloxy)methyl)phenyl)propanoic acid (E203) in THF under $N_2$ and cooled to 0° C. was added $CH_3I$ followed by NaH and the solution was warmed and allowed to stir for 18 h. The mixture was taken up in EtOAc and extracted with $NH_4Cl_{(sat)}$, dried ($MgSO_4$), filtered, and evaporated. Column chromatography ($SiO_2$, 0-10% MeOH/$CH_2Cl_2$ gradient) gave pure 3-(tert-butoxycarbonyl(methyl)amino)-2-(4-((tnisopropylsilyloxy)methyl)phenyl)propanoic acid (E204).

Tert-butyl 3-(isoquinolin-6-ylamino)-3-oxo-2-(4-((triisopropylsilyloxy)methyl)phenyl)propyl(methyl)carbamate (E205) was prepared from E204 according to the below:

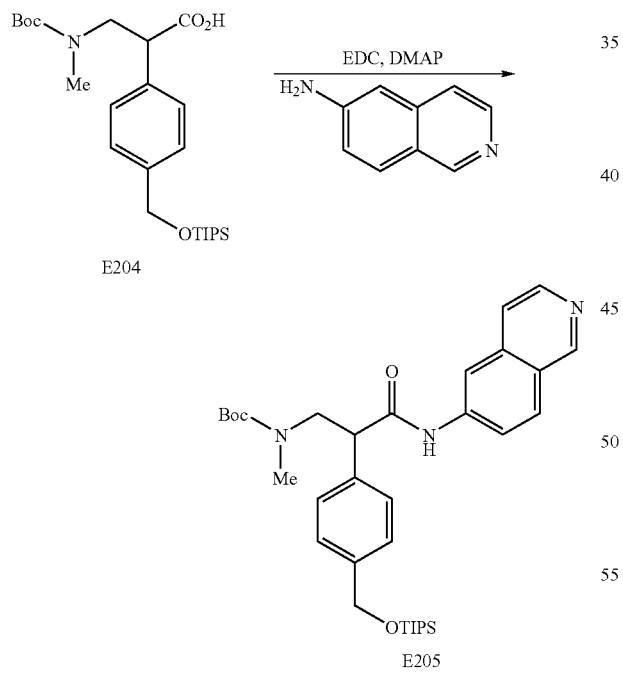

To 3-(tert-butoxycarbonyl(methyl)amino)-2-(4-((triisopropylsilyloxy)methyl)phenyl)propanoic acid (E204) in pyridine was added was added EDC, DMAP, and 6-aminoisoquinoline, and the solution was stirred overnight at room temperature. The mixture was poured into $NaHCO_{3(sat)}$ and extracted with EtOAc. The organics were dried ($MgSO_4$), filtered, and evaporated. Column chromatography ($SiO_2$, 0-6% MeOH/$CH_2Cl_2$ gradient) gave pure tert-butyl 3-(isoquinolin-6-ylamino)-3-oxo-2-(4-((triisopropylsilyloxy)methyl)phenyl)propyl(methyl)carbamate (E205).

Tert-butyl 2-(4-(hydroxymethyl)phenyl)-3-(isoquinolin-6-ylamino)-3-oxopropyl(methyl)carbamate (E205-1) was prepared from E205 according to the below:

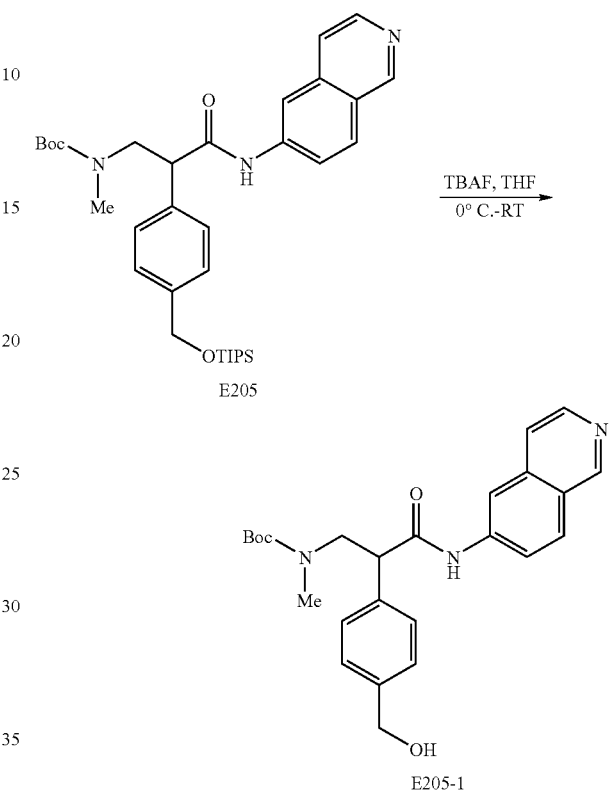

To tert-butyl 3-(isoquinolin-6-ylamino)-3-oxo-2-(4-((thisopropylsilyloxy)methyl)phenyl)Propyl(methyl)carbamate (E205) in THF under $N_2$ at 0° C. was added TBAF, and the solution was stirred for 30 min at 0° C. The reaction was warmed to room temperature and stirred another 4.5 h. The compound was poured into EtOAc and washed with $NH_4Cl_{(sat)}$, dried ($MgSO_4$), filtered, and evaporated. Column chromatography ($SiO_2$, 0-20% MeOH/$CH_2Cl_2$ gradient) gave pure tert-butyl 2-(4-(hydroxymethyl)phenyl)-3-(isoquinolin-6-ylamino)-3-oxopropyl(methyl)carbamate (E205-1)

4-(3-(tert-butoxycarbonyl(methyl)amino)-1-(isoquinolin-6-ylamino)-1-oxopropan-2-yl)benzyl 2,4-dimethylbenzoate (E205-2) was prepared from E205-1 according to the below:

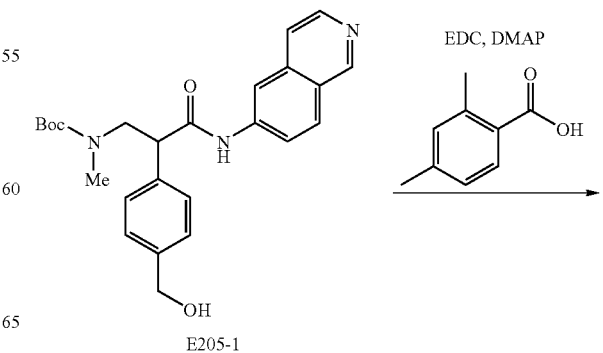

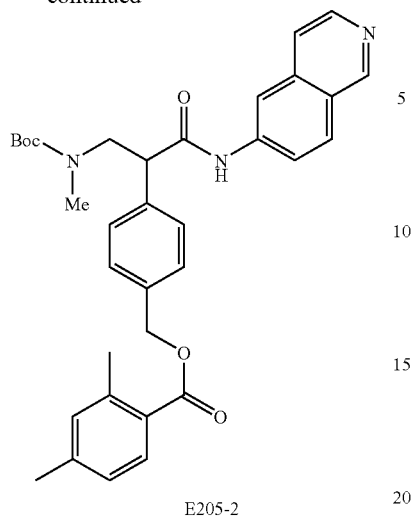

E205-2

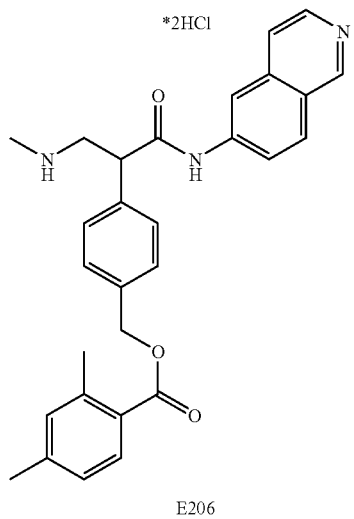

E206

To tert-butyl 2-(4-(hydroxymethyl)phenyl)-3-(isoquinolin-6-ylamino)-3-oxopropyl(methyl)carbamate (E205-1) in pyridine was added was added EDC, DMAP, and 2,4-dimethylbenzoic acid, and the solution was stirred overnight at room temperature. The mixture was poured into NaHCO$_{3(sat)}$ and extracted with EtOAc. The organics were dried (MgSO$_4$), filtered, and evaporated. Column chromatography (SiO$_2$, 0-5% MeOH/CH$_2$Cl$_2$ gradient) gave pure 4-(3-(tert-butoxycarbonyl(methyl)amino)-1-(isoquinolin-6-ylamino)-1-oxopropan-2-yl)benzyl 2,4-dimethylbenzoate (E205-2).

4-(1-(isoquinolin-6-ylamino)-3-(methylamino)-1-oxopropan-2-yl)benzyl 2,4-dimethylbenzoate (E206) was prepared from E205-2 according to the below:

To 4-(3-(tert-butoxycarbonyl(methyl)amino)-1-(isoquinolin-6-ylamino)-1-oxopropan-2-yl)benzyl 2,4-dimethylbenzoate (E205-2) in CH$_2$Cl$_2$ was added HCl (4 N in dioxane) and the solution was stirred for 8-10 h. The solvents were evaporated to give pure 4-(1-(isoquinolin-6-ylamino)-3-(methylamino)-1-oxopropan-2-yl)benzyl 2,4-dimethylbenzoate (E206).

Examples 207-211

Using commercially available compounds and largely the procedures set forth in Examples 204-206 and substituting the appropriate starting materials, the compounds E206-E211 have been made, shown in Table 6.

TABLE 6

Compounds E206-E211.

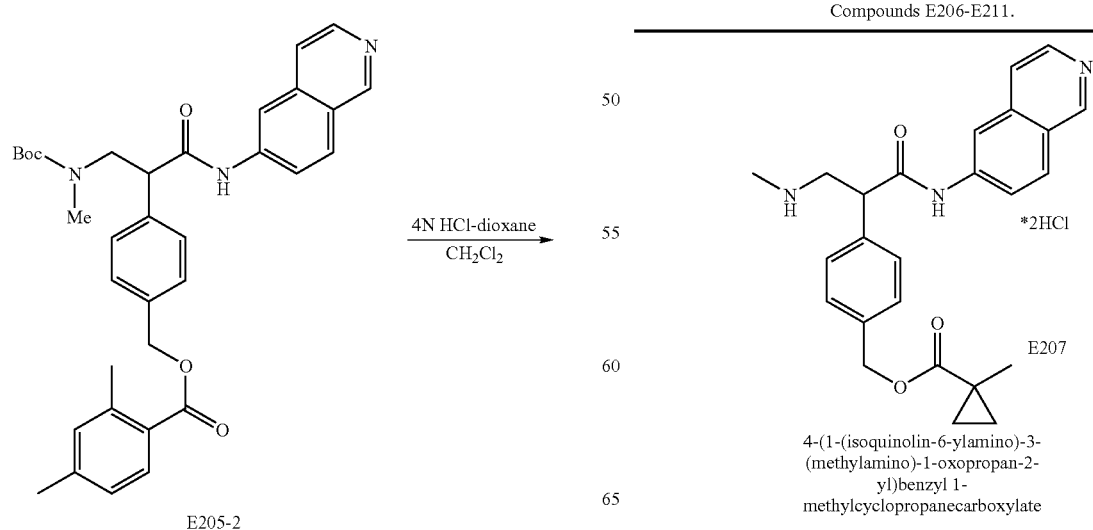

E207

4-(1-(isoquinolin-6-ylamino)-3-(methylamino)-1-oxopropan-2-yl)benzyl 1-methylcyclopropanecarboxylate

TABLE 6-continued

Compounds E206-E211.

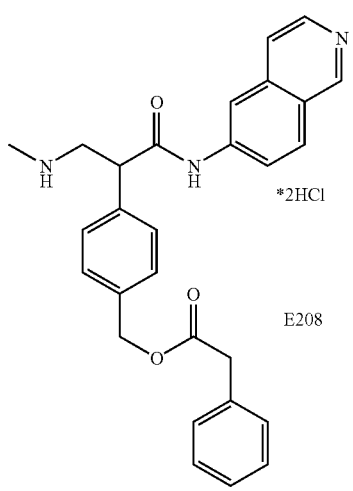 [SMILES: CNCC(C(=O)Nc1ccc2cnccc2c1)c1ccc(COC(=O)Cc2ccccc2)cc1]

E208

4-(1-(isoquinolin-6-ylamino)-3-
(methylamino)-1-oxopropan-2-
yl)benzyl 2-phenylacetate

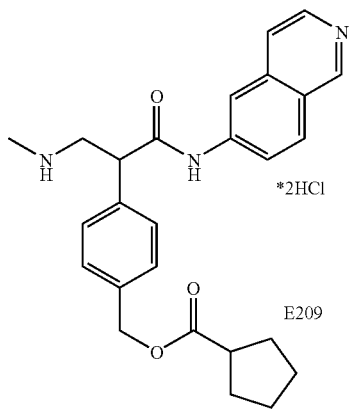 [SMILES: CNCC(C(=O)Nc1ccc2cnccc2c1)c1ccc(COC(=O)C2CCCC2)cc1]

E209

4-(1-(isoquinolin-6-ylamino)-3-
(methylamino)-1-oxopropan-2-
yl)benzyl
cyclopentanecarboxylate

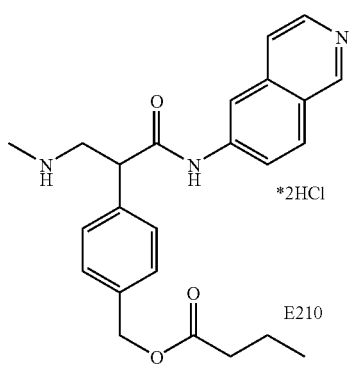 [SMILES: CCCC(=O)OCc1ccc(C(CNC)C(=O)Nc2ccc3cnccc3c2)cc1]

E210

4-(1-(isoquinolin-6-ylamino)-3-
(methylamino)-1-oxopropan-2-
yl)benzyl butyrate

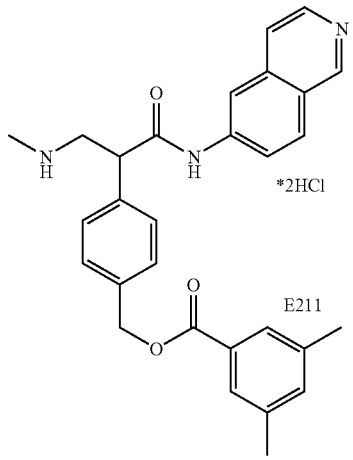

E211

4-(1-(isoquinolin-6-ylamino)-3-
(methylamino)-1-oxopropan-2-
yl)benzyl 3,5-dimethylbenzoate

Example 212

3-(tert-butoxycarbonylamino)-2-(3-((triisopropylsilyloxy)methyl)phenyl)propanoic acid (E212) was prepared.

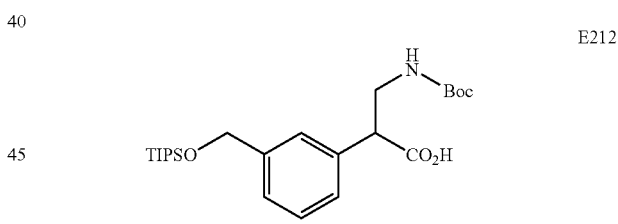

E212

Using commercially available compounds and largely the procedures set forth in Examples 198-203 and substituting the appropriate starting materials 3-(tert-butoxycarbonylamino)-2-(3-((triisopropylsilyloxy)methyl)phenyl)propanoic acid (E212) was made.

Examples 213-216

Using commercially available compounds and largely the procedures set forth in Examples 204-206 and substituting the appropriate starting materials, the compounds E213-E216 have been made, shown in Table 7.

TABLE 7

Compounds E213-E216.

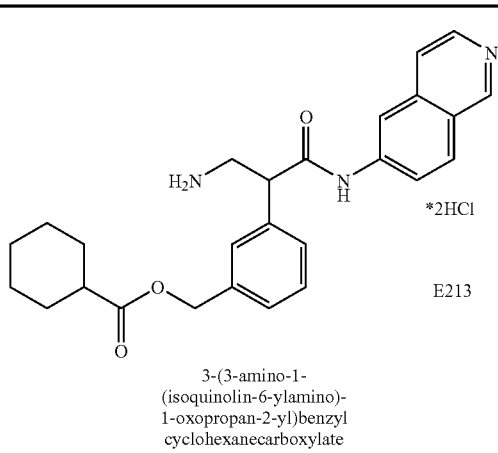

E213
3-(3-amino-1-(isoquinolin-6-ylamino)-1-oxopropan-2-yl)benzyl cyclohexanecarboxylate

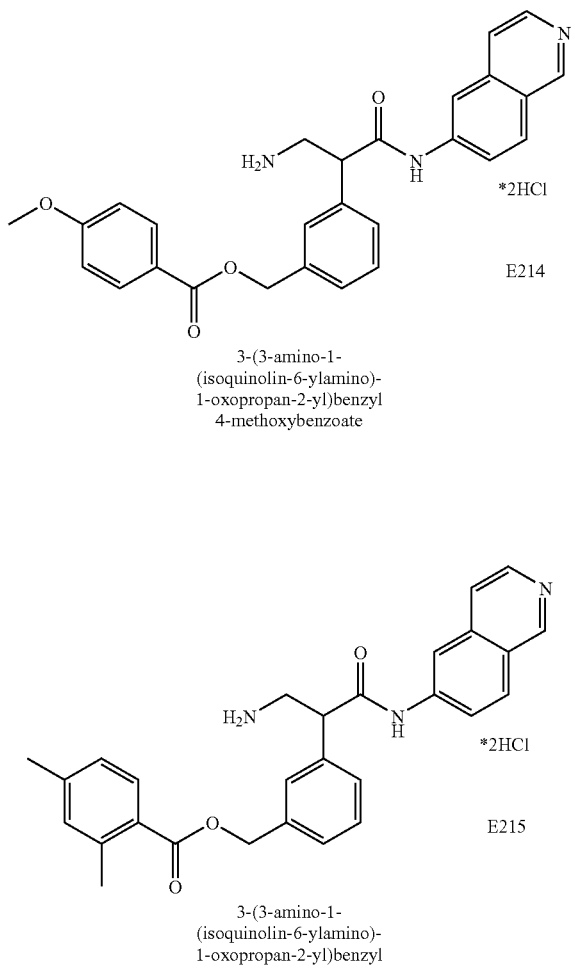

E214
3-(3-amino-1-(isoquinolin-6-ylamino)-1-oxopropan-2-yl)benzyl 4-methoxybenzoate E215
3-(3-amino-1-(isoquinolin-6-ylamino)-1-oxopropan-2-yl)benzyl 2,4-dimethylbenzoate

TABLE 7-continued

Compounds E213-E216.

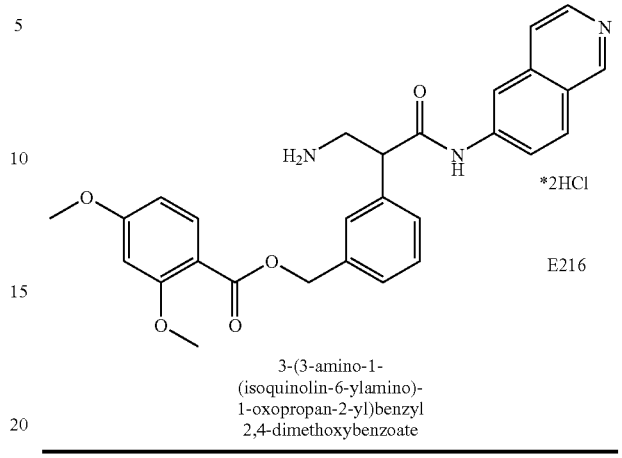

E216
3-(3-amino-1-(isoquinolin-6-ylamino)-1-oxopropan-2-yl)benzyl 2,4-dimethoxybenzoate

Examples 217-225

Using commercially available compounds and largely the procedures set forth in Examples 198-203 and Examples 204-206 and substituting the appropriate starting materials, the compounds E217-E225 could be made, shown in Table 8.

TABLE 8

Compounds E217-E225.

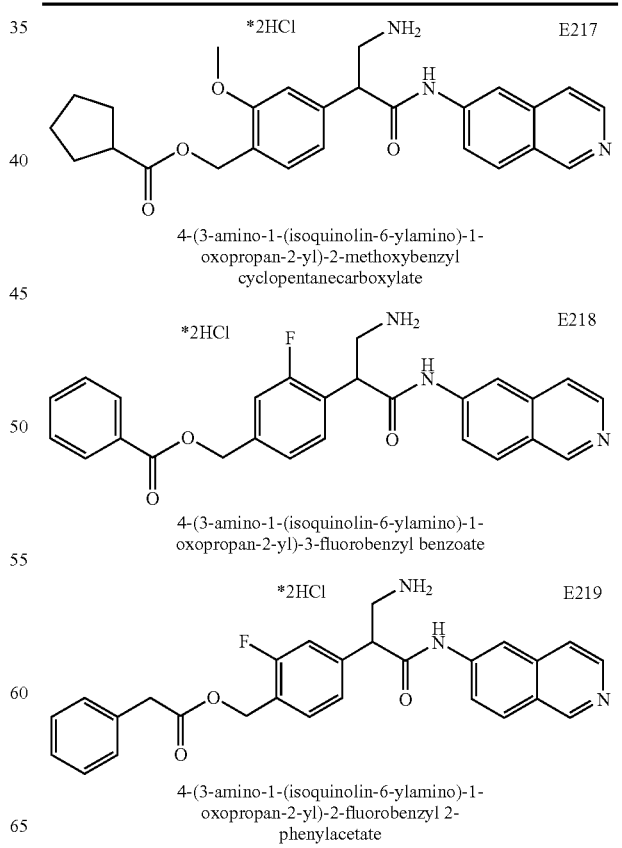

E217
4-(3-amino-1-(isoquinolin-6-ylamino)-1-oxopropan-2-yl)-2-methoxybenzyl cyclopentanecarboxylate E218
4-(3-amino-1-(isoquinolin-6-ylamino)-1-oxopropan-2-yl)-3-fluorobenzyl benzoate E219
4-(3-amino-1-(isoquinolin-6-ylamino)-1-oxopropan-2-yl)-2-fluorobenzyl 2-phenylacetate

TABLE 8-continued

Compounds E217-E225.

E220 *2HCl
4-(3-amino-1-(isoquinolin-6-ylamino)-1-oxopropan-2-yl)-3-methylbenzyl benzoate E221 *2HCl
3-(3-amino-1-(isoquinolin-6-ylamino)-1-oxopropan-2-yl)-4-methylbenzyl pivalate E222 *2HCl
5-(3-amino-1-(isoquinolin-6-ylamino)-1-oxopropan-2-yl)-2-fluorobenzyl cyclohexanecarboxylate E223 *2HCl
5-(3-amino-1-(isoquinolin-6-ylamino)-1-oxopropan-2-yl)-2-methoxybenzyl 4-methylbenzoate E224 *2HCl
3-(3-amino-1-(isoquinolin-6-ylamino)-1-oxopropan-2-yl)-5-fluorobenzyl 2-phenoxyacetate E225 *2HCl
3-(3-amino-1-(isoquinolin-6-ylamino)-1-oxopropan-2-yl)-2-fluorobenzyl 3-fluorobenzoate

Example 226

3-(isopropylamino)-N-(isoquinolin-6-yl)-2-phenylpropanamide dihydrochloride (E226) was prepared as shown below:

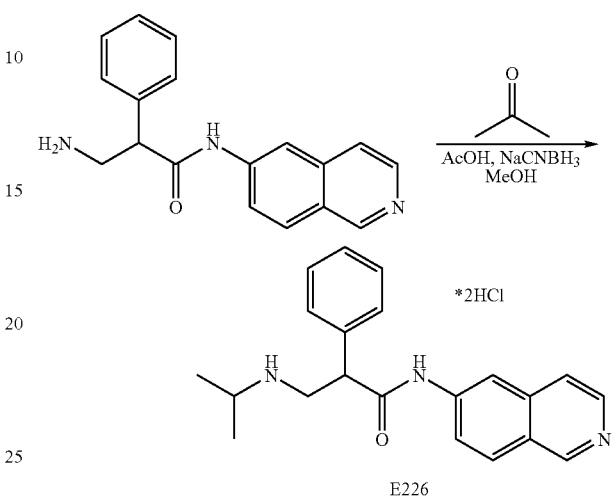

To 3-amino-N-(isoquinolin-6-yl)-2-phenylpropanamide in MeOH/AcOH was added acetone and NaCNBH$_3$. Then after 15 min the mixture was poured into NaHCO$_{3(sat)}$ and extracted with CH$_2$Cl$_2$. The organics were dried (Na$_2$SO$_4$), filtered, and evaporated. Column chromatography (SiO$_2$, 5% 2 N NH$_3$-MeOH/CH$_2$Cl$_2$) gave pure 3-(isopropylamino)-N-(isoquinolin-6-yl)-2-phenylpropanamide. The compound was taken up in CH$_2$Cl$_2$ and HCl (1 M in Et$_2$O) was added. The solution was evaporated to give 3-(isopropylamino)-N-(isoquinolin-6-yl)-2-phenylpropanamide dihydrochloride (E226).

Examples 227-230

Using commercially available compounds and largely the procedures set forth in Example 226 and substituting the appropriate starting materials, the compounds E227-E230 could be made, shown in Table 9.

TABLE 9

Compounds E227-E230.

E227 *2HCl o)-1-(isoquinolin-6-ylamino)-1-oxopropan-2-yl)be

TABLE 9-continued

Compounds E227-E230.

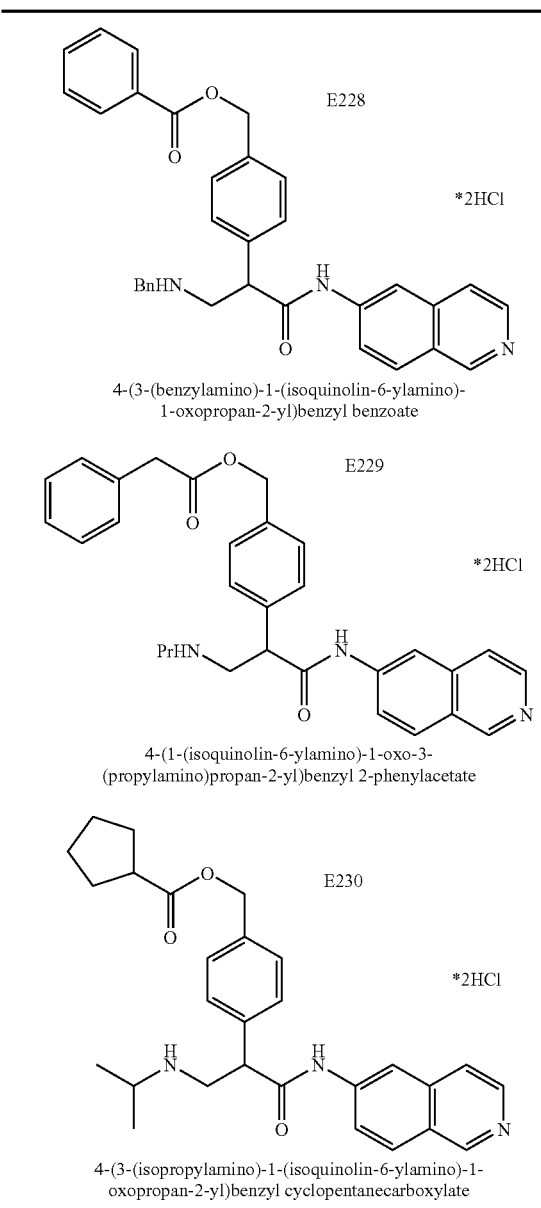

E228
4-(3-(benzylamino)-1-(isoquinolin-6-ylamino)-
1-oxopropan-2-yl)benzyl benzoate E229
4-(1-(isoquinolin-6-ylamino)-1-oxo-3-
(propylamino)propan-2-yl)benzyl 2-phenylacetate E230
4-(3-(isopropylamino)-1-(isoquinolin-6-ylamino)-1-
oxopropan-2-yl)benzyl cyclopentanecarboxylate

Examples 231-241

Figure 13:
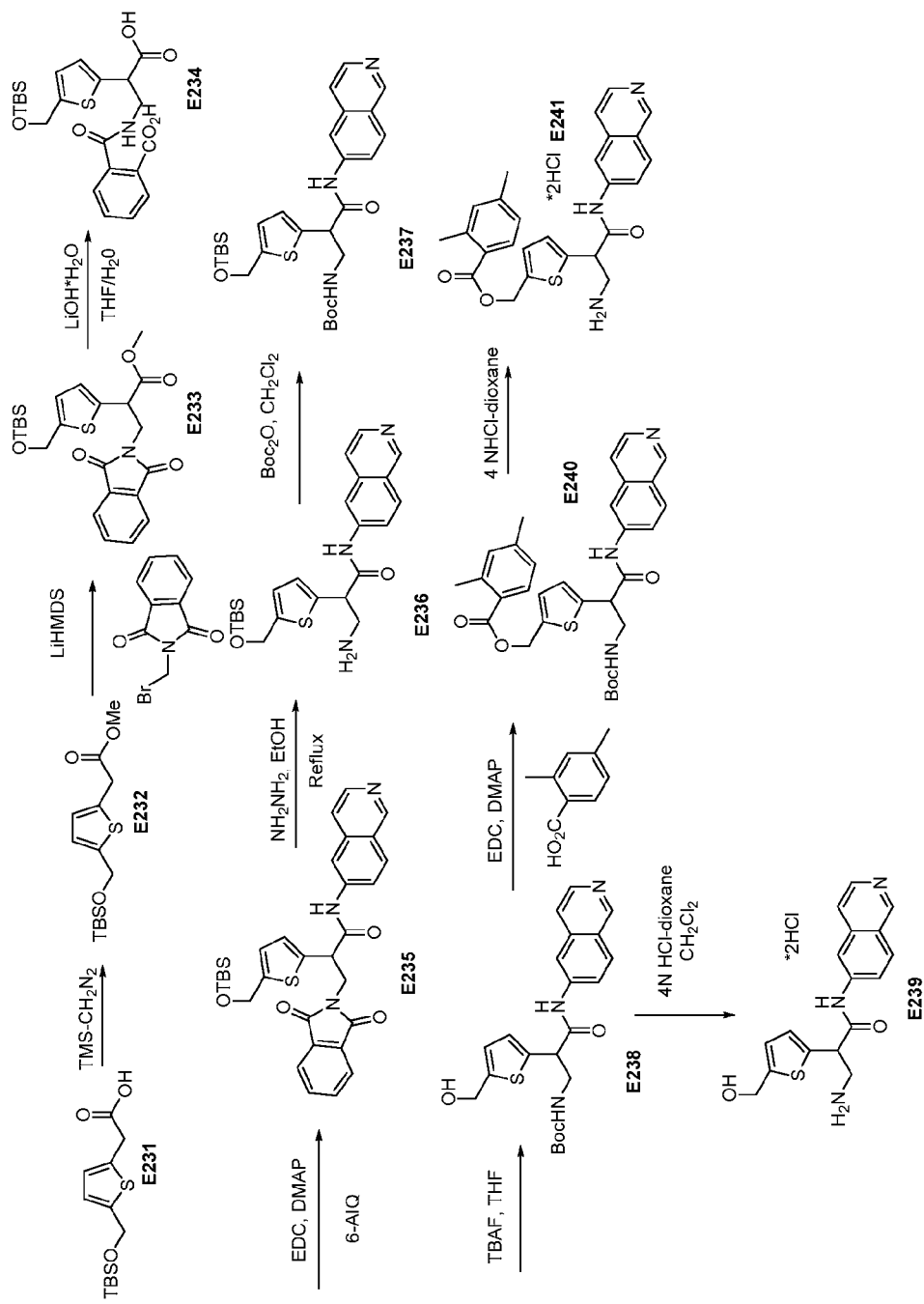
FIG. 13 is a scheme for the synthesis of compounds, including E231-E241.

Compounds E231-E241 were prepared according to the scheme in FIG. 13.

Methyl 2-(5-((tert-butyldimethylsilyloxy)methyl)thiophen-2-yl)acetate (E232) was prepared from E231 according to the below:

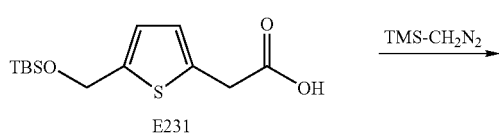

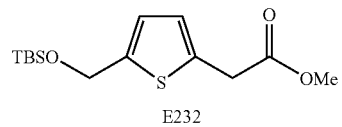

To 2-(5-((tert-butyldimethylsilyloxy)methyl)thiophen-2-yl) acetic acid (E231) in MeOH at 0° C. was added TMS-CH$_2$N$_2$ until the solution persisted in a yellow color and TLC indicated completion of the reaction. The solution stirred for 30 min and then was quenched with a few drops of AcOH. The solvents were evaporated and column chromatography (SiO$_2$, 0-15% EtOAc/Hexanes) gave pure methyl 2-(5-((tert-butyldimethylsilyloxy)methyl)thiophen-2-yl)acetate (E232).

Methyl 2-(5-((tert-butyldimethylsilyloxy)methyl) thiophen-2-yl)-3-(1,3-dioxoisoindolin-2-yl)propanoate (E233) was prepared from E232 according to the below:

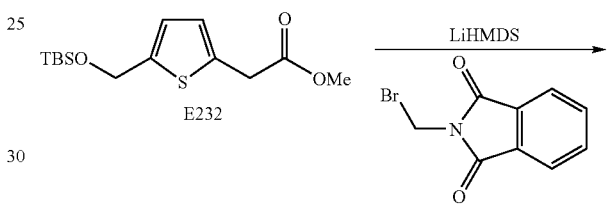

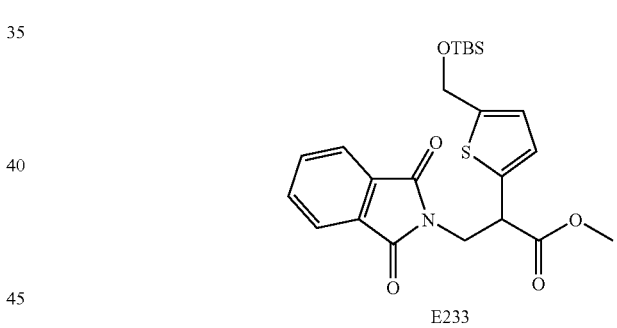

To a solution of LiHMDS in THF cooled to –78° C. was added a cooled solution (approx –78° C.) of methyl 2-(5-((tert-butyldimethylsilyloxy)methyl)thiophen-2-yl)acetate (E232) in THF via syringe. The solution was stirred at –78° C. for 30 min. Bromo-methylphthalimide was added directly to the anion, and the solution was immediately removed from the –78° C. bath and placed in an ice bath and stirred for 2 h. The reaction was then poured into NH$_4$Cl$_{(sat)}$ and extracted with EtOAc. The organics were dried (Na$_2$SO$_4$), filtered, and evaporated. Column chromatography (SiO$_2$, 15-20% EtOAc/Hexanes) gave pure methyl 2-(5-((tert-butyldimethylsilyloxy)methyl)thiophen-2-yl)-3-(1,3-dioxoisoindolin-2-yl) propanoate (E233).

2-(2-(5-(tert-butyldimethylsilyloxy)methyl)thiophen-2-yl)-2-carboxyethylcarbamoyl)benzoic acid (E234) was prepared from E233 according to the below:

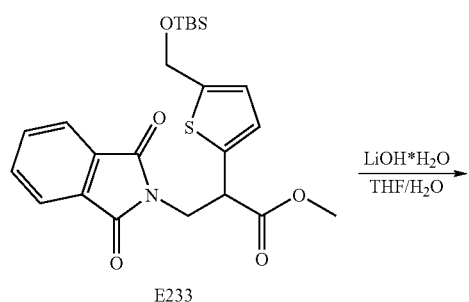

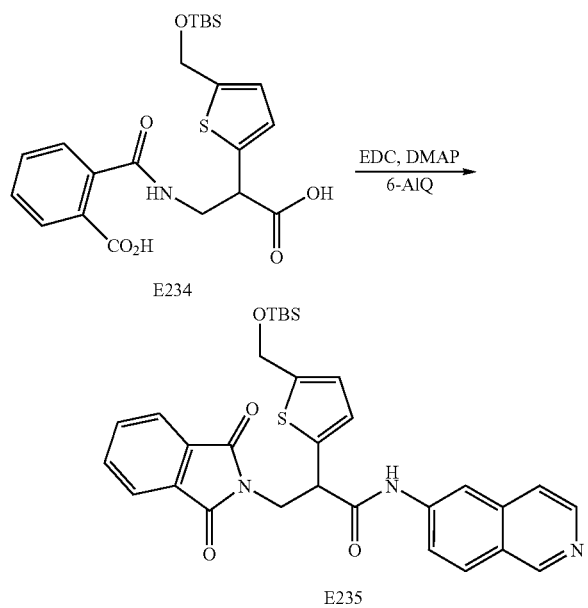

To methyl 2-(5-((tert-butyldimethylsilyloxy)methyl)thiophen-2-yl)-3-(1,3-dioxoisoindolin-2-yl)propanoate (E233) in THF/H$_2$O was added LiOH*H$_2$O, and the solution was stirred for 1.5 h or until complete conversion to product was visible by LC-MS. The solution was then poured into EtOAc/NH$_4$Cl(sat)/1 N HCl (3:1) and the aqueous layer was further extracted with EtOAc. The organics were dried (Na$_2$SO$_4$), filtered, evaporated, and dried to give crude 2-(2-(5-(tert-butyldimethylsilyloxy)methyl)thiophen-2-yl)-2-carboxyethylcarbamoyl)benzoic acid (E234).

2-(2-(5-(tert-butyldimethylsilyloxy)methyl)thiophen-2-yl)-3-(1,3-dioxoisoindolin-2-yl)-N-(isoquinolin-6-yl)propanamide (E235) was prepared from E234 according to the below:

To 2-(2-(5-(tert-butyldimethylsilyloxy)methyl)thiophen-2-yl)-2-carboxyethylcarbamoyl)benzoic acid (E234) in pyridine was added EDC, DMAP, and 6-aminoisoquinoline, and the solution was flushed with N$_2$, capped, and stirred overnight. The mixture was poured into EtOAc/NaHCO$_{3(sat)}$ and the aqueous layer was further extracted with EtOAc. The organics were dried (Na$_2$SO$_4$), filtered, and evaporated. Column chromatography (SiO$_2$, 4% MeOH/CH$_2$Cl$_2$) gave pure 2-(2-(5-(tert-butyldimethylsilyloxy)methyl)thiophen-2-yl)-3-(1,3-dioxoisoindolin-2-yl)-N-(isoquinolin-6-yl)propanamide (E235).

3-amino-2-(5-(((tert-butyldimethylsilyloxy)methyl)thiophen-2-yl)-N-(isoquinolin-6-yl)propanamide (E236) was prepared from E235 according to the below:

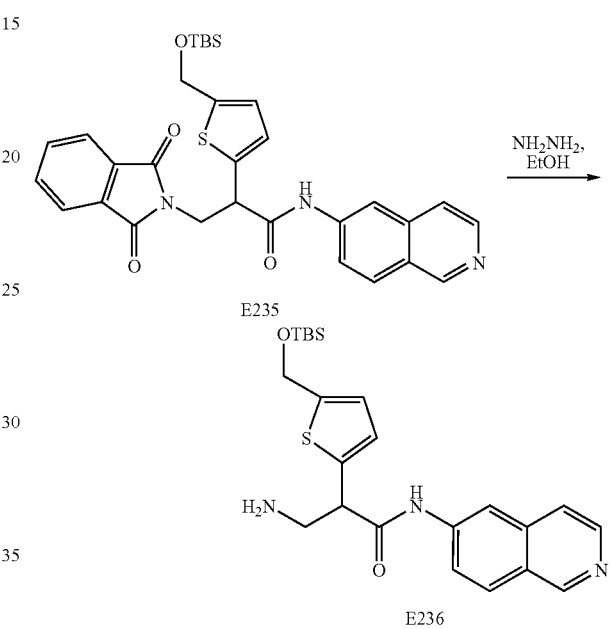

To 2-(2-(5-(tert-butyldimethylsilyloxy)methyl)thiophen-2-yl)-3-(1,3-dioxoisoindolin-2-yl)-N-(isoquinolin-6-yl)propanamide (E235) in EtOH was added NH$_2$—NH$_2$ and the solution was stirred for 7 h at room temperature then heated to 50° C. for 1 h. The solution was cooled, the solids were filtered, and the solvents were evaporated. Column chromatography (SiO$_2$, 5-8% 2 N NH$_3$-MeOH/CH$_2$Cl$_2$) gave pure 3-amino-2-(5-(((tert-butyldimethylsilyloxy)methyl)thiophen-2-yl)-N-(isoquinolin-6-yl)propanamide (E236).

Tert-butyl 2-(5-((tert-butyldimethylsilyloxy)methyl)thiophen-2-yl)-3-(isoquinolin-6-ylamino)-3-oxopropylcarbamate (E237) was prepared from E236 according to the below:

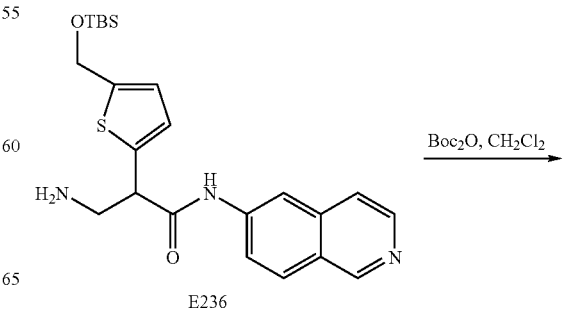

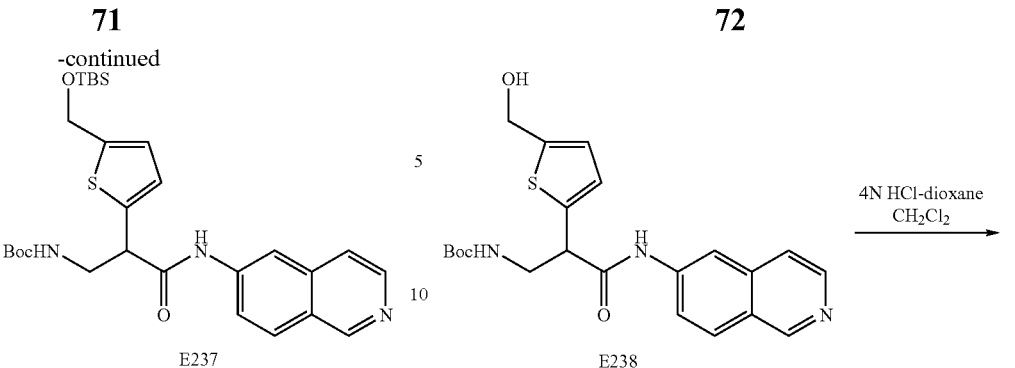

To 3-amino-2-(5-(((tert-butyldimethylsilyloxy)methyl) thiophen-2-yl)-N-(isoquinolin-6-yl)propanamide (E236) in CH$_2$Cl$_2$ at 0° C. was added a solution of Boc$_2$O in CH$_2$Cl$_2$ (also cooled to 0° C. before addition). The solution was stirred at 0° C. for 2 h and then poured into CH$_2$Cl$_2$ and NaHCO$_{3(sat)}$. The solution was further extracted with CH$_2$Cl$_2$ and the combined organics were dried (Na$_2$SO$_4$), filtered, and evaporated. Column chromatography (SiO$_2$, 3% MeOH/CH$_2$Cl$_2$) gave pure tert-butyl 2-(5-(((tert-butyldimethylsilyloxy)methyl) thiophen-2-yl)-3-(isoquinolin-6-ylamino)-3-oxopropylcarbamate (E237).

Tert-butyl 2-(5-(hydroxymethyl)thiophen-2-yl)-3-(isoquinolin-6-ylamino)-3-oxopropylcarbamate (E238) was prepared from E237 according to the below:

To tert-butyl 2-(5-(((tert-butyldimethylsilyloxy)methyl) thiophen-2-yl)-3-(isoquinolin-6-ylamino)-3-oxopropylcarbamate (E237) in THF at 0° C. was added TBAF and the solution was stirred for 0° C. for 30 min then warmed to room temperature for 2 h. The compound was poured into EtOAc and washed with NH$_4$Cl$_{(sat)}$, dried (Na$_2$SO$_4$), filtered, and evaporated. Column chromatography (SiO$_2$, 6% MeOH/CH$_2$Cl$_2$) gave pure tert-butyl 2-(5-(hydroxymethyl)thiophen-2-yl)-3-(isoquinolin-6-ylamino)-3-oxopropylcarbamate (E238).

3-amino-2-(5-(hydroxymethyl)thiophen-2-yl)-N-(isoquinolin-6-yl)propanamide dihydrochloride (E239) was prepared from E238 according to the below:

To a solution of tert-butyl 2-(5-(hydroxymethyl)thiophen-2-yl)-3-(isoquinolin-6-ylamino)-3-oxopropylcarbamate (E238) in CH$_2$Cl$_2$ was added 4 N HCl-dioxane and the solution was stirred for 4 h. The solvents were evaporated to give 3-amino-2-(5-(hydroxymethyl)thiophen-2-yl)-N-(isoquinolin-6-yl)propanamide dihydrochloride (E239).

(5-(3-tert-butoxylcarbonylamino)-1-(isoquinolin-6-ylamino)-1-oxopropan-2-yl)methyl 2,4 dimethylbenzoate (E240) was prepared from E239 according to the below:

To tert-butyl 2-(5-(hydroxymethyl)thiophen-2-yl)-3-(isoquinolin-6-ylamino)-3-oxopropylcarbamate (E238) in pyridine was added EDC, DMAP, and 2,4-dimethyl benzoic acid, and the solution was flushed with N₂, capped, and stirred overnight. The mixture was poured into EtOAc/NaHCO$_{3(sat)}$ and the aqueous layer was further extracted with EtOAc. The organics were dried (Na$_2$SO$_4$), filtered, and evaporated. Column chromatography (SiO$_2$, 4% MeOH/CH$_2$Cl$_2$) gave pure (5-(3-tert-butoxylcarbonylamino)-1-(isoquinolin-6-ylamino)-1-oxopropan-2-yl)methyl 2,4 dimethylbenzoate (E240).

(5-(3-amino-1-(isoquinolin-6-ylamino)-1-oxopropan-2-yl)thiophen-2-yl)methyl 2,4-dimethylbenzoate dihydrochloride (E241) was prepared from E240 according to the below:

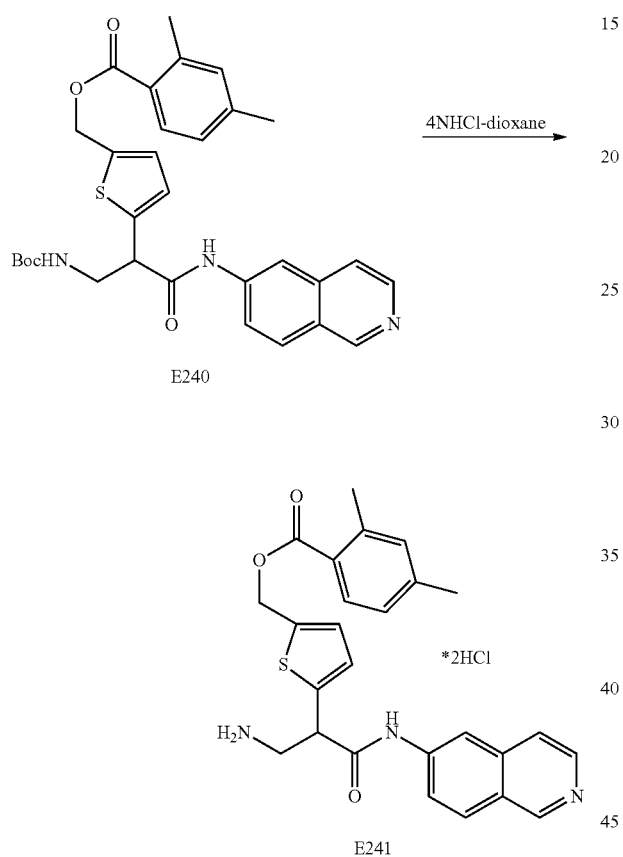

To (5-(3-tert-butoxylcarbonylamino)-1-(isoquinolin-6-ylamino)-1-oxopropan-2-yl)methyl 2,4 dimethylbenzoate (E240) in CH$_2$Cl$_2$ was added HCl (4 N in dioxane) and the solution was stirred overnight. The solvents were evaporated to give pure (5-(3-amino-1-(isoquinolin-6-ylamino)-1-oxopropan-2-yl)thiophen-2-yl)methyl 2,4-dimethylbenzoate dihydrochloride (E241).

Examples 242-248

Using commercially available compounds and largely the procedures set forth in Examples 231-241 and substituting the appropriate starting materials, E242-E248 could be synthesized, shown in Table 10.

TABLE 10

Compounds E242-E248.

| Example | R¹ | R² |
|---|---|---|
| 242 | —CH₂Ph | H |
| 243 | -3,5-diMePh | Me |
| 244 | cyclopentyl | Me |
| 245 | cyclohexyl | H |
| 246 | —(CH₂)₂CH₃ | Me |
| 247 | i-Pr | H |
| 248 | -Ph | Me |

Examples 249-253

Figure 14:
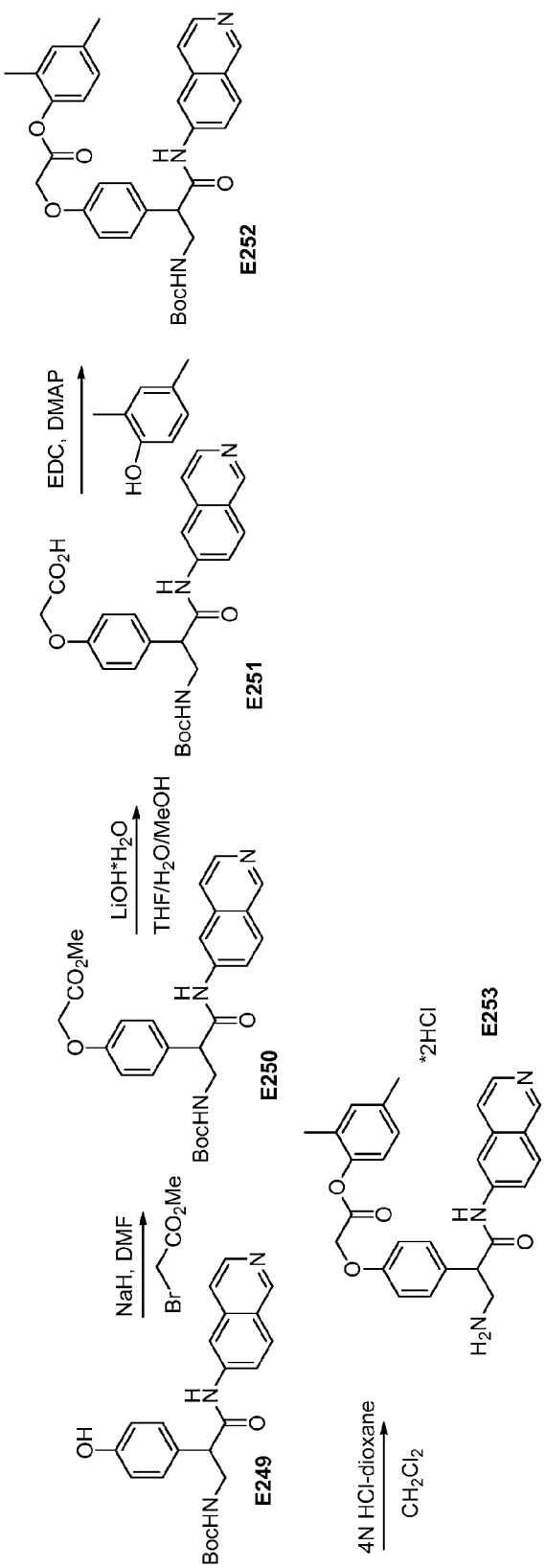
FIG. 14 is a scheme for the synthesis of compounds, including E249-253.

Methyl 2-(4-(3-(tert-butoxycarbonylamino)-1-(isoquinolin-6-ylamino)-1-oxopropan-2-yl)phenoxy)acetate (E250) was prepared from E249 according to the scheme in FIG. 14. To tert-butyl 2-(4-hydroxyphenyl)-3-(isoquinolin-6-ylamino)-3-oxopropylcarbamate (E249) in DMF cooled to −35° C. was added NaH, and the solution was stirred at −35° C. for 30 min. Then, methyl bromoacetate was added and the solution was warmed and stirred at 0° C. for 1 h. The solution was poured into NaHCO$_{3(sat)}$/EtOAc and further extracted with EtOAc. The combined organics were dried (Na$_2$SO$_4$), filtered, and evaporated. Column chromatography (SiO$_2$, 3-4% MeOH/CH$_2$Cl$_2$) gave pure methyl 2-(4-(3-(tert-butoxycarbonylamino)-1-(isoquinolin-6-ylamino)-1-oxopropan-2-yl)phenoxy)acetate (E250).

2-(4-(3-tert-butoxycarbonylamino)-1-(isoquinolin-6-ylamino)-1-oxopropan-2-yl)phenoxy)acetic acid (E251) was prepared from E250 according to the below:

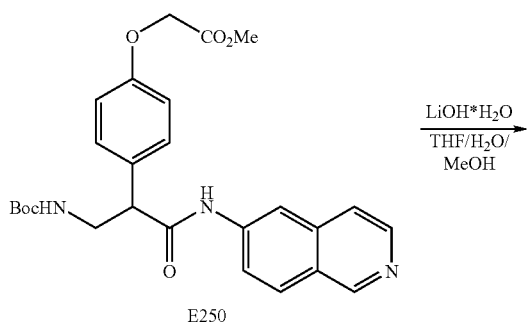

E250

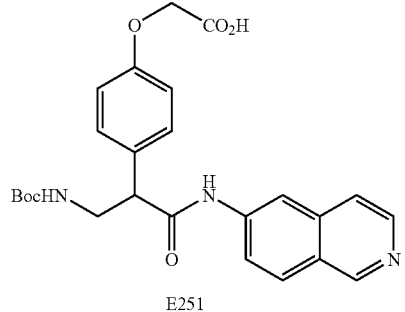

E251

To methyl 2-(4-(3-(tert-butoxycarbonylamino)-1-(isoquinolin-6-ylamino)-1-oxopropan-2-yl)phenoxy)acetate (E250) in THF/H$_2$O/MeOH at 0° C. was added LiOH*H$_2$O, and the solution was stirred for 2 h at 0° C. The mixture was then quenched with HCl (1 N, Et$_2$O) and evaporated. Column chromatography (SiO$_2$, 20% MeOH/CH$_2$Cl$_2$) gave pure 2-(4-(3-tert-butoxycarbonylamino)-1-(isoquinolin-6-ylamino)-1-oxopropan-2-yl)phenoxy)acetic acid (E251).

2,4-dimethylphenyl 2-(4-(3-(tert-butoxycarbonylamino)-1-(isoquinolin-6-ylamino)-1-oxopropan-2-yl)phenoxy)acetate (E252) was prepared from E251 according to the below:

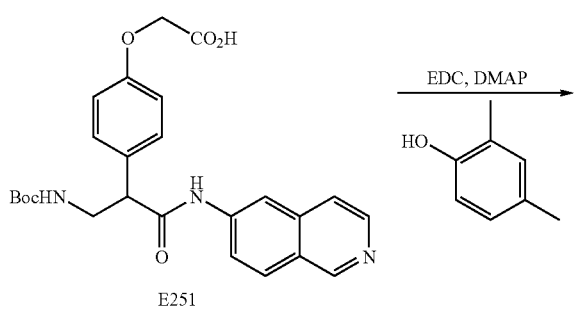

E251

E252

To 2-(4-(3-tert-butoxycarbonylamino)-1-(isoquinolin-6-ylamino)-1-oxopropan-2-yl)phenoxy)acetic acid (E251) in pyridine was added EDC, DMAP, and 2,4-dimethylphenol, and the solution was stirred for 5 h. The mixture was then poured into EtOAc/NaHCO$_{3(sat)}$ and extracted with EtOAc. The combined organics were dried (Na$_2$SO$_4$), filtered, and evaporated. Column chromatography (SiO$_2$, 2-3% MeOH/CH$_2$Cl$_2$) gave 2,4-dimethylphenyl 2-(4-(3-(tert-butoxycarbonylamino)-1-(isoquinolin-6-ylamino)-1-oxopropan-2-yl)phenoxy)acetate (E252).

2,4-dimethylphenyl 2-(4-(3-amino-1-(isoquinolin-6-ylamino)-1-oxopropan-2-yl)phenoxy)acetate dihydrochloride (E253) was prepared from E252 according to the below:

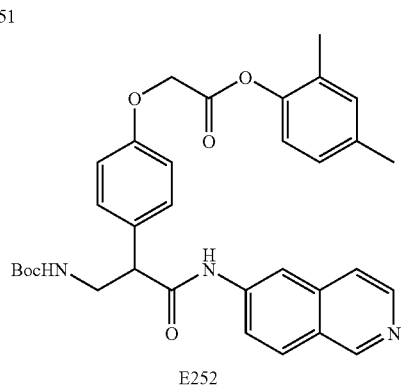

E252

E253

To 2,4-dimethylphenyl 2-(4-(3-(tert-butoxycarbonylamino)-1-(isoquinolin-6-ylamino)-1-oxopropan-2-yl)phenoxy)acetate (E252) in CH$_2$Cl$_2$ was added HCl (4 N, dioxane) and the solution was stirred overnight. The solvents were evaporated to give 2,4-dimethylphenyl 2-(4-(3-amino-1-(isoquinolin-6-ylamino)-1-oxopropan-2-yl)phenoxy)acetate dihydrochloride (E253).

Examples 254-273

Using commercially available compounds and largely the procedures set forth in Examples 249-253 and substituting the appropriate starting materials E254-E261 (shown in Table 11) were made and E262-E273 (shown in Table 12) could be synthesized.

TABLE 11

Compounds E254-E261.

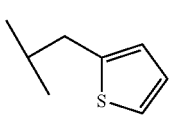

| Example | X | R |
|---|---|---|
| 254 | O | Me |
| 255 | O | H |
| 256 | O | -2,4-diMePh |
| 257 | O | -i-Pr |
| 258 | O | —CH₂Ph |
| 259 | O | -3,5-diMePh |
| 260 | NH | Ph |
| 261 | NH | —(CH₂)₃CH₃ |

TABLE 12

Compounds E262-E273.

| Example | X | R¹ | R² |
|---|---|---|---|
| 262 | O | Ph | H |
| 263 | O | 4-MeOPh | Me |
| 264 | O | 2,4-di-F—Ph | Me |
| 265 | O | —CH₂Ph | H |
| 266 | O | —CH₂CH=CH₂ | H |
| 267 | O | (thiophene-CH₂CH₂—) | Me |
| 268 | NH | 2,4-diMePh | Me |
| 269 | NH | 3,5-diMePh | Me |
| 270 | NH | 2-F—Ph | H |
| 271 | NH | —CH₂-4-MeOPh | Me |
| 272 | NH | -2-MeOPh | H |
| 273 | NH | -3-pyridyl | H |

Example 274

Using commercially available compounds and largely the procedures set forth in Examples 249-253 and substituting the appropriate starting materials E274 was made.

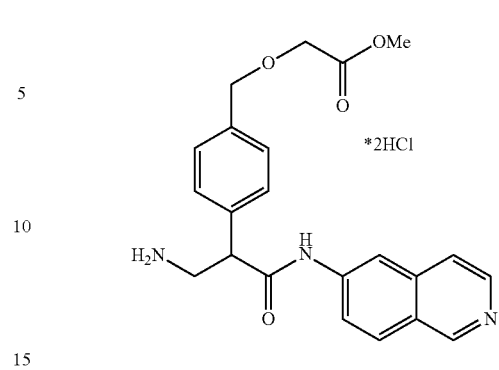

Examples 275-278

Figure 15:
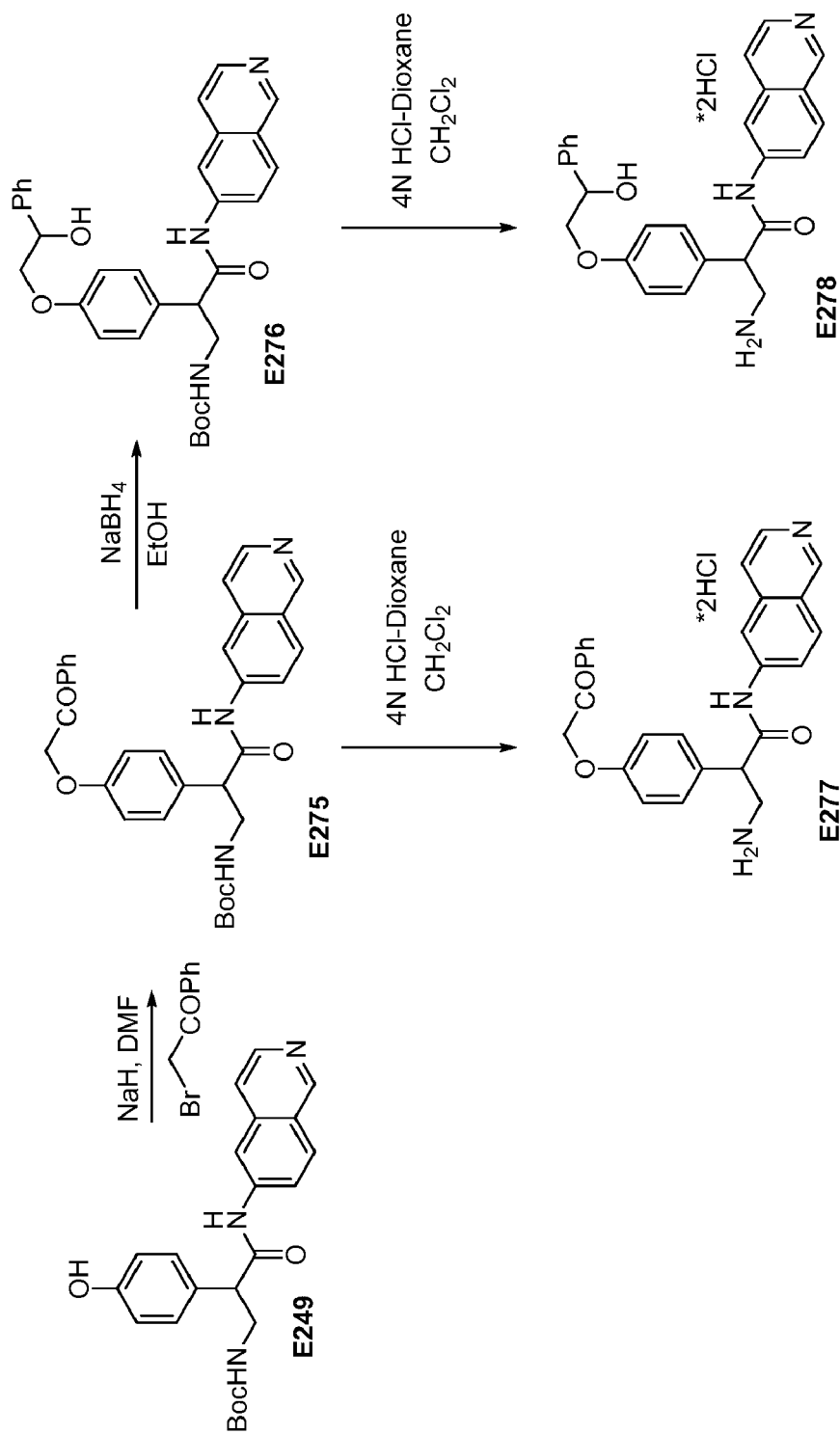
FIG. 15 is a scheme for the synthesis of compounds, including E275-E278.

Compounds E275-E278 were prepared according to the scheme presented in FIG. 15. Tert-butyl 3-(isoquinolin-6-ylamino)-3-oxo-2-(4-(2-oxo-2-phenylethoxy)phenyl)propylcarbamate (E275) was prepared from E249 according to the below:

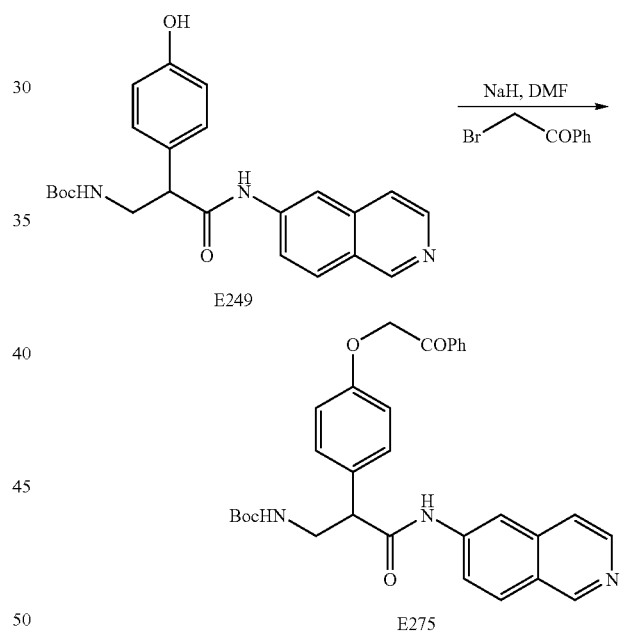

To tert-butyl 2-(4-hydroxyphenyl)-3-(isoquinolin-6-ylamino)-3-oxopropylcarbamate (E249) in DMF cooled to −35° C. was added NaH and the solution was stirred at −35° C. for 30 min. Then, 2-bromoacetophenone was added and the solution was warmed and stirred at 0° C. for 2 h. The solution was poured into NaHCO₃(sat)/EtOAc and further extracted with EtOAc. The combined organics were dried (Na₂SO₄), filtered, and evaporated. Column chromatography (SiO₂, 3% MeOH/CH₂Cl₂) gave tert-butyl 3-(isoquinolin-6-ylamino)-3-oxo-2-(4-(2-oxo-2-phenylethoxy)phenyl)propylcarbamate (E275).

3-amino-N-(isoquinolin-6-yl)-2-(4-(2-oxo-2-phenylethoxy)phenyl)propanamide dihydrochloride (E277) was prepared from E275 according to the below:

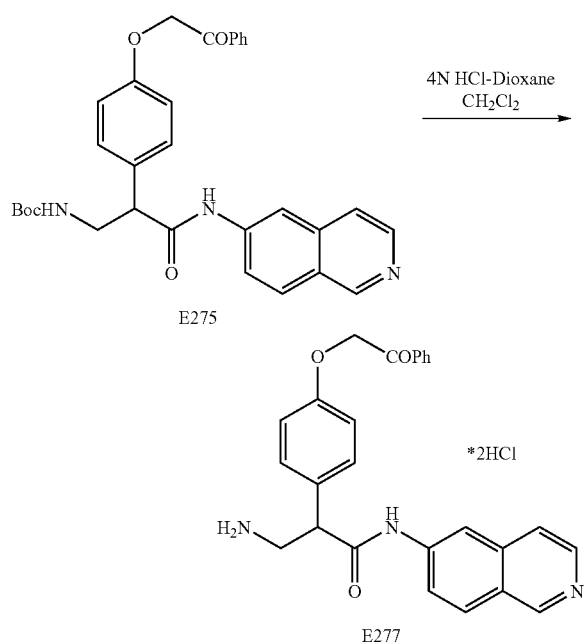

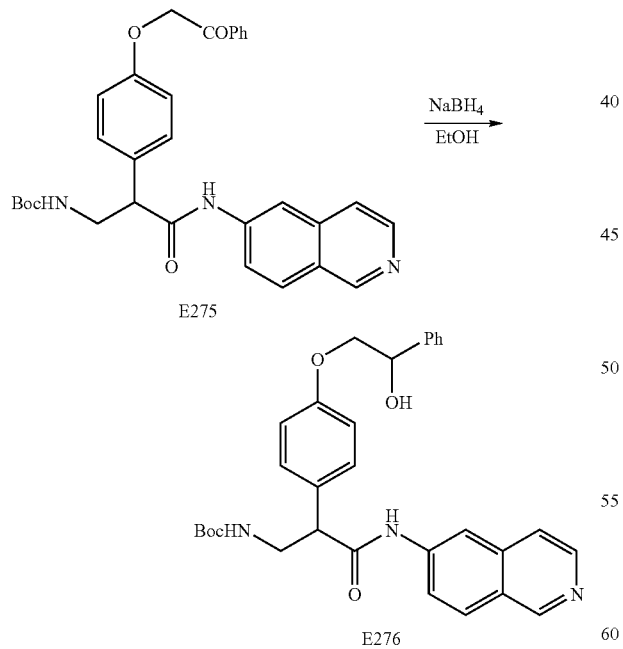

To tert-butyl 3-(isoquinolin-6-ylamino)-3-oxo-2-(4-(2-oxo-2-phenylethoxy)phenyl)propylcarbamate (E275) in CH$_2$Cl$_2$ was added HCl (4 N, dioxane) and the solution was stirred overnight. The solvents were evaporated to give pure 3-amino-N-(isoquinolin-6-yl)-2-(4-(2-oxo-2-phenylethoxy)phenyl)propanamide dihydrochloride (E277).

Tert-butyl 2-(4-(2-hydroxy-2-phenylethoxy)phenyl)-3-(isoquinolin-6-ylamino)-3-oxopropylcarbamate (E276) was prepared from E275 according to the below:

To tert-butyl 3-(isoquinolin-6-ylamino)-3-oxo-2-(4-(2-oxo-2-phenylethoxy)phenyl)propylcarbamate (E275) in EtOH was added NaBH$_4$ and the solution was stirred for 20 min at room temperature. The mixture was then poured into NaHCO$_{3(sat)}$ and extracted with CH$_2$Cl$_2$. The combined organics were dried (Na$_2$SO$_4$), filtered, and evaporated. Column chromatography (SiO$_2$, 5% MeOH/CH$_2$Cl$_2$) gave pure tert-butyl 2-(4-(2-hydroxy-2-phenylethoxy)phenyl)-3-(isoquinolin-6-ylamino)-3-oxopropylcarbamate (E276).

3-amino-2-(4-(2-hydroxy-2-phenylethoxy)phenyl)-N-(isoquinolin-6-yl)propanamide dihydrochloride (E278) was prepared from E276 according to the below:

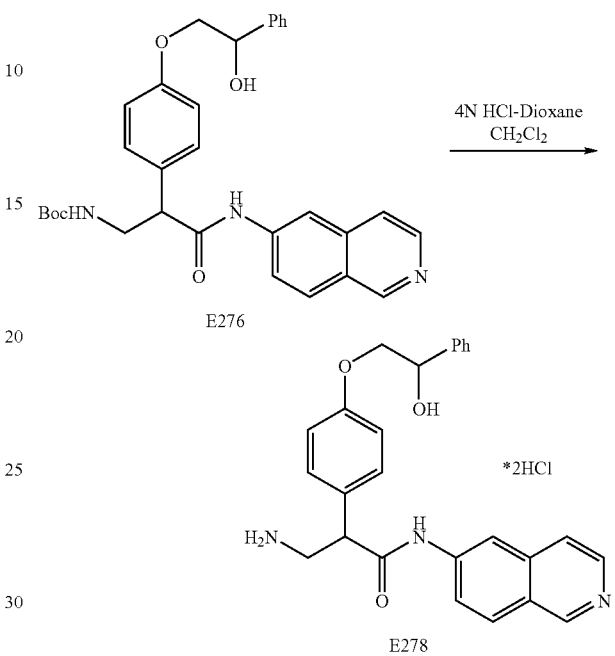

To tert-butyl 2-(4-(2-hydroxy-2-phenylethoxy)phenyl)-3-(isoquinolin-6-ylamino)-3-oxopropylcarbamate (E276) in CH$_2$Cl$_2$ was added HCl (4 N, dioxane) and the solution was stirred overnight. The solvents were evaporated to give 3-amino-2-(4-(2-hydroxy-2-phenylethoxy)phenyl)-N-(isoquinolin-6-yl)propanamide dihydrochloride (E278).

Examples 279-288

Using commercially available compounds and largely the procedures set forth in Examples 275-278 and substituting the appropriate starting materials E279-E282 (shown in Table 13) were made and E283-E288 (shown in Table 14) could be synthesized.

TABLE 13

Compounds E279-E282.

| Example | X | R |
|---|---|---|
| 279 | O | Ph |
| 280 | OH | Ph |
| 281 | O | -4-MeOPh |
| 282 | O | -2-MeOPh |

TABLE 14

Compounds E283-E288.

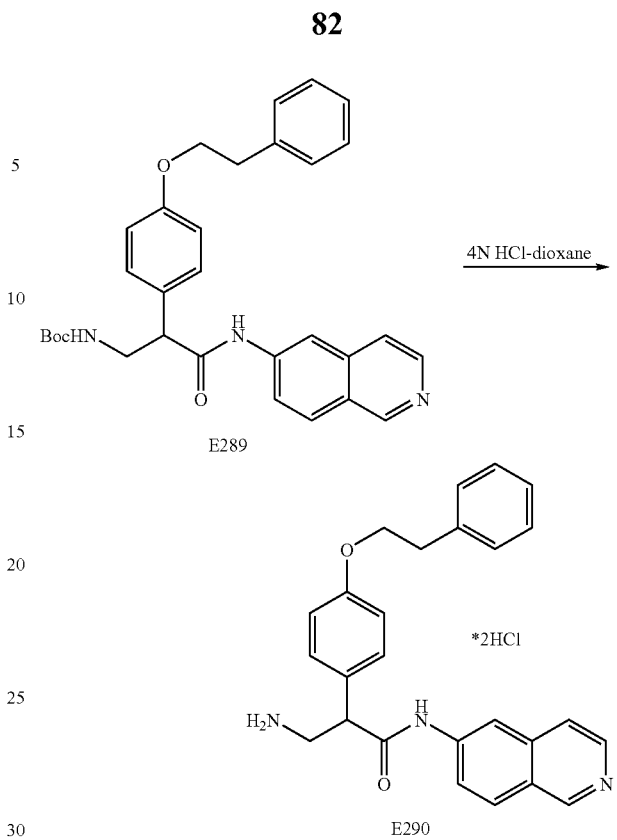

| Example | X | R1 | R2 |
|---|---|---|---|
| 283 | O | -2-F-Ph | Me |
| 284 | O | -2,4 diCl-Ph | H |
| 285 | O | -3-MePh | H |
| 286 | OH | -4-MeOPh | H |
| 287 | OH | -2-MeOPh | H |
| 288 | OH | -3-MePh | Me |

Examples 289-290

Figure 16:
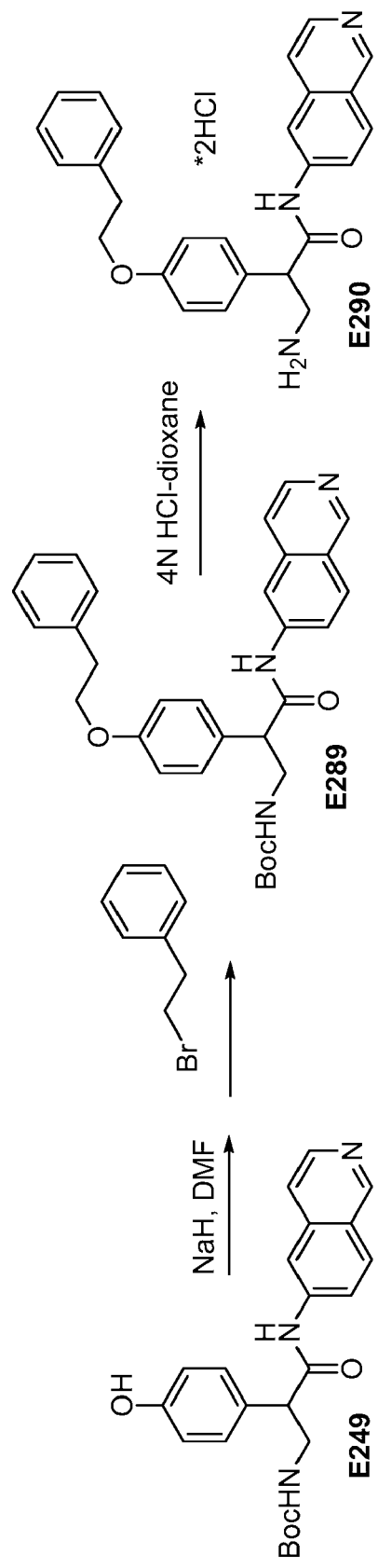
FIG. 16 is a scheme for the synthesis of compounds, including E289-E290.

Compounds E289 and E290 were prepared according to the scheme presented in FIG. 16.

Tert-butyl 3-(isoquinolin-6-ylamino)-3-oxo-2-(phenethoxyphenyl)propylcarbamate (E289) was prepared from E249 according to the below:

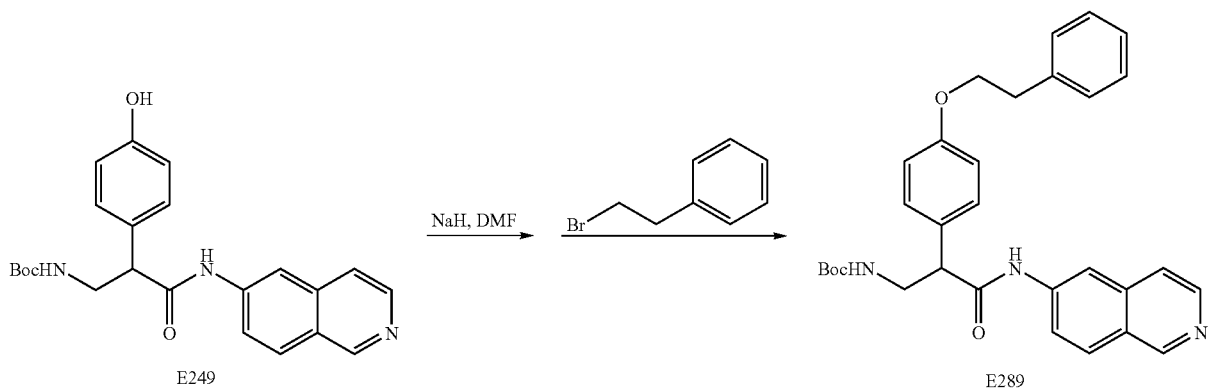 [SMILES: CC(C)(C)OC(=O)NCC(C(=O)Nc1ccc2cnccc2c1)c1ccc(O)cc1 ; BrCCc1ccccc1 ; CC(C)(C)OC(=O)NCC(C(=O)Nc1ccc2cnccc2c1)c1ccc(OCCc2ccccc2)cc1]

To tert-butyl 2-(4-hydroxyphenyl)-3-(isoquinolin-6-ylamino)-3-oxopropylcarbamate (E249) in DMF cooled to −35° C. was added NaH and the solution was stirred at −40° C. for 30 min. Then, 2-bromoethylbenzene was added and the solution was warmed and stirred at room temperature for 2 h. The solution was poured into $NaHCO_{3(sat)}$/EtOAc and further extracted with EtOAc. The combined organics were dried ($Na_2SO_4$), filtered, and evaporated. Column chromatography ($SiO_2$, 3-4% MeOH/$CH_2Cl_2$) gave pure tert-butyl 3-(isoquinolin-6-ylamino)-3-oxo-2-(phenethoxyphenyl)propylcarbamate (E289).

3-amino-N-(isoquinolin-6-yl)-2-(4-phenethoxyphenyl)propanamide dihydrochloride (E290) was prepared from E289 according to the below:

To tert-butyl 3-(isoquinolin-6-ylamino)-3-oxo-2-(phenethoxyphenyl)propylcarbamate (E289) in $CH_2Cl_2$ was added HCl (4 N, dioxane) and the solution was stirred overnight. The solvents were evaporated to give 3-amino-N-(isoquinolin-6-yl)-2-(4-phenethoxyphenyl)propanamide dihydrochloride (E290).

Examples 291-299

Using commercially available compounds and largely the procedures set forth in Examples 289-290 and substituting the appropriate starting materials E291-E292 (Table 15) were made and E294-E299 (Table 16) could be synthesized.

TABLE 15

Compounds E291-E292.

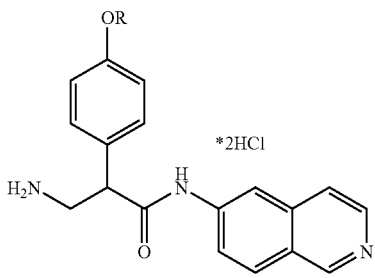

| Example | R |
|---|---|
| 291 | —(CH$_2$)$_2$Ph |
| 292 | —CH$_2$Ph** |

** E292 was synthesized from previous schemes carried out in which the benzyl was in place of the TIPS protecting group.

Using commercially available compounds and largely the procedures set forth in Examples 289-290 and substituting the appropriate starting materials E293 was made.

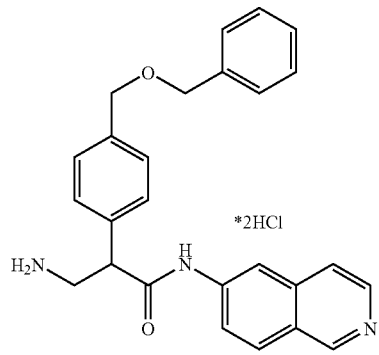

E293

TABLE 16

Compounds E294-E299.

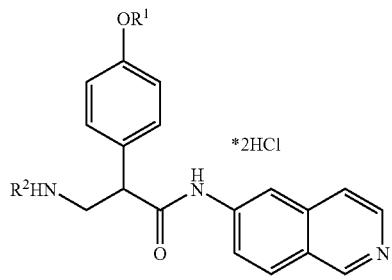

| Example | R1 | R2 |
|---|---|---|
| 294 | —CH$_2$-4-F-Ph | H |
| 295 | —CH$_2$-2-MePh | Me |
| 296 | —CH$_2$-2-CNPh | Me |
| 297 | —(CH$_2$)$_2$-4-MePh | H |
| 298 | —(CH$_2$)$_2$-2-FPh | H |

TABLE 16-continued

Compounds E294-E299.

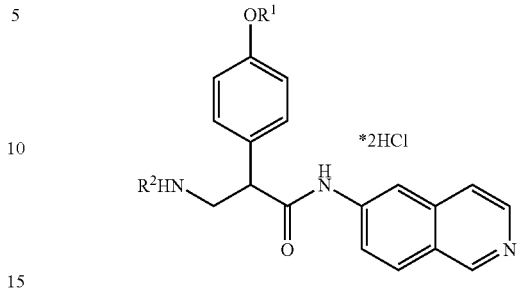

| Example | R1 | R2 |
|---|---|---|
| 299 | 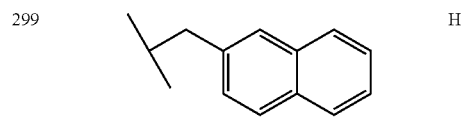 | H |

Examples 300-308

Figure 17:
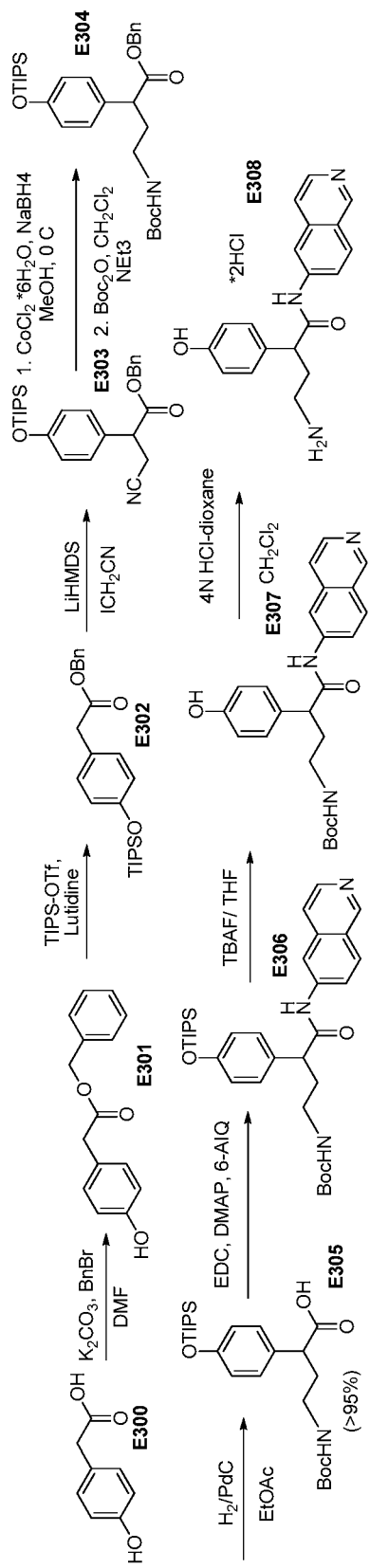
FIG. 17 is a scheme for the synthesis of compounds, including E300-E308.

Compounds E300-E308 were prepared according to the scheme in FIG. 17.

Benzyl 2-(4-hydroxyphenyl)acetate (E301) was prepared from E300 according to the below:

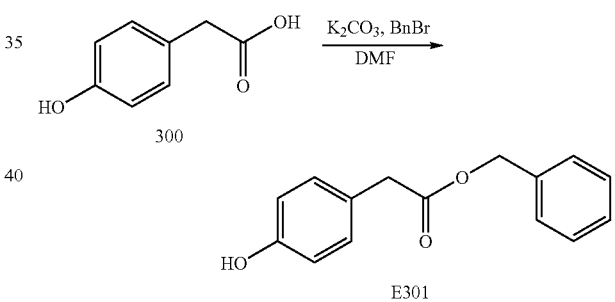

To 2-(4-hydroxyphenyl)acetic acid in DMF cooled to 0° C. was added K$_2$CO$_3$ and the solution was stirred for 30 min. Then, benzyl bromide was added and the solution stirred at 0° C. and was allowed to slowly warm to 15-20° C. After all the ice was melted the solution was poured into NH$_4$Cl$_{(sat)}$ and extracted with EtOAc. The combined organics were dried (Na$_2$SO$_4$), filtered, and evaporated. Column chromatography (SiO$_2$, 0-35% EtOAc/Hex) gave pure benzyl 2-(4-hydroxyphenyl)acetate (E301).

Benzyl 2-(4-(triisopropylsiloxy)phenyl)acetate (E302) was prepared from E301 according to the below:

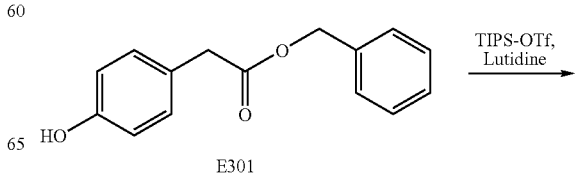

-continued

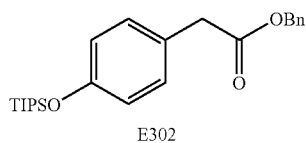
E302

To benzyl 2-(4-hydroxyphenyl)acetate (E301) in CH₂Cl₂ at 0° C. was added 2,6-lutidine and TIPS-OTf and the solution stirred for 2.5 h at 0° C. The mixture was poured into NH₄Cl$_{(sat)}$ and extracted with CH₂Cl₂. The combined organics were dried (Na₂SO₄), filtered, and evaporated. Column chromatography (SiO₂, 0-15% EtOAc/Hex) gave pure benzyl 2-(4-(triisopropylsiloxy)phenyl)acetate (E302).

Benzyl 3-cyano-2-(triisopropylsilyloxy)phenyl)propanoate (E303) was prepared from E302 according to the below:

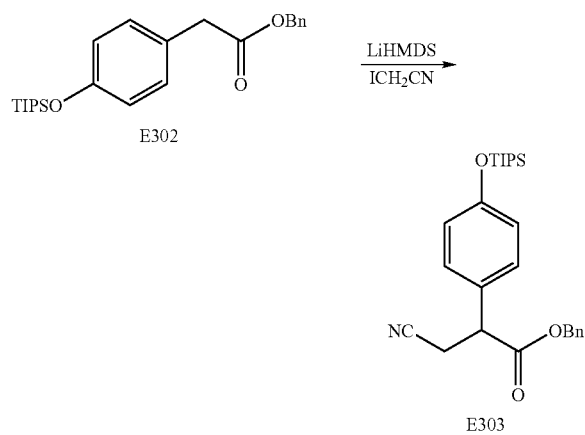

To a solution of LiHMDS in THF at −78° C. was added a solution of benzyl 2-(4-(triisopropylsiloxy)phenyl)acetate (E302) in THF also cooled to approx −78° C., and this mixture was allowed to stir at −78° C. for 30 min. Iodoacetonitrile was then added and the mixture was warmed to 0° C. and stirred for 2 h. The mixture was poured into NH₄Cl$_{(sat)}$ and extracted with EtOAc. The combined organics were dried (Na₂SO₄), filtered, and evaporated. Column chromatography (SiO₂, 0-25% EtOAc/Hex) gave pure benzyl 3-cyano-2-(triisopropylsilyloxy)phenyl)propanoate (E303).

Benzyl 4-(tertbutoxycarbonylamino)-2-(4-(triisopropylsilyloxy)phenyl)butanoate (E304) was prepared from E303 according to the below:

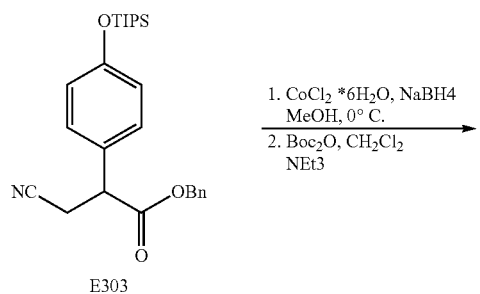

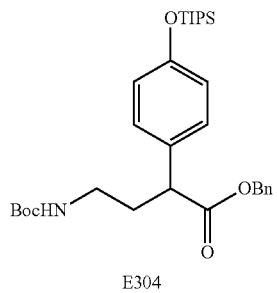
E304

To a solution of benzyl 3-cyano-2-(triisopropylsilyloxy)phenyl)propanoate (E303) in MeOH cooled to 0° C. was added CoCl₂*6H₂O and NaBH₄ and the solution was allowed to stir for 20 min. Then, HCl (1.25 N in MeOH) was added and the solution stirred an additional 20 min at 0° C. The solvents were evaporated and the mixture was taken up in CH₂Cl₂ and cooled to 0° C. Boc₂O and NEt₃ were added and the solution stirred at 0° C. for 1.5 h. The mixture was poured into NH₄Cl$_{(sat)}$ and extracted with CH₂Cl₂. The combined organics were dried (Na₂SO₄), filtered, and evaporated. Column chromatography (SiO₂, 10-20% EtOAc/Hexanes) gave pure benzyl 4-(tertbutoxycarbonylamino)-2-(4-(triisopropylsilyloxy)phenyl)butanoate (E304).

Preparation of 4-(tertbutoxycarbonylamino)-2-(4-(triisopropylsilyloxy)phenyl)butanoic acid (E305) was prepared from E304 according to the below:

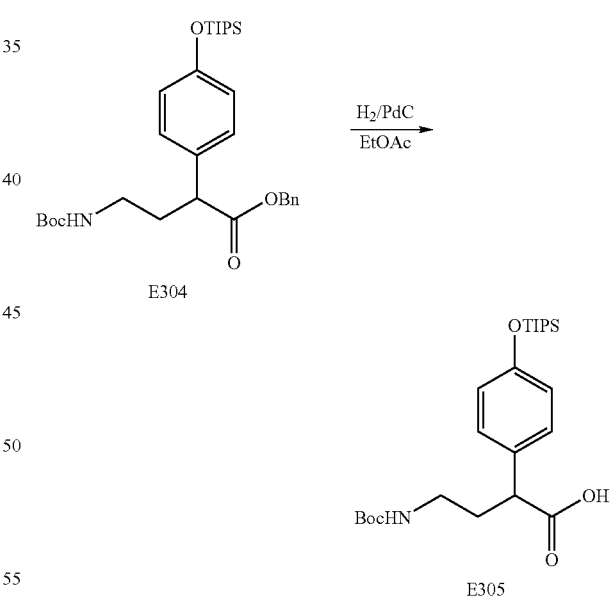

To benzyl 4-(tert-butoxycarbonylamino)-2-(4-(triisopropylsilyloxy)phenyl)butanoate (E304) in EtOAc was added Pd/C (10%) and the solution was kept under a H₂ atomosphere for 2 h. The mixture was filtered over Celite and the solvent was evaporated to give 4-(tert-butoxycarbonylamino)-2-(4-(triisopropylsilyloxy)phenyl)butanoic acid (E305).

Tert-butyl 4-(isoquinolin-6-ylamino)-4-oxo-3-(4-(triisopropylsilyloxy)phenyl)butylcarbamate (E306) was prepared from E305 according to the below:

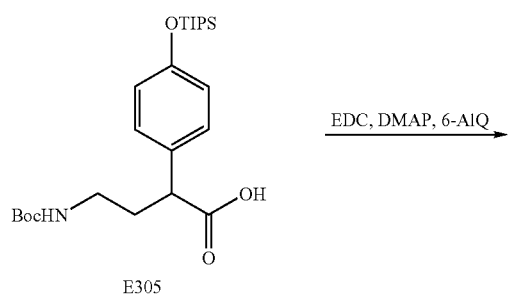

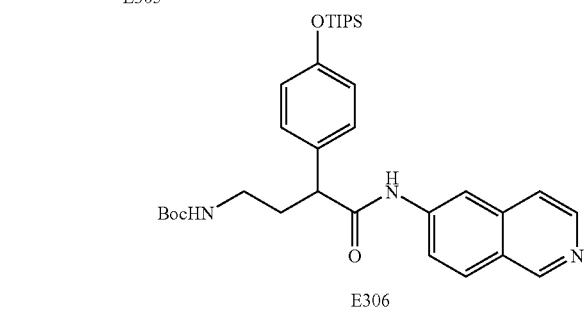

To 4-(tert-butoxycarbonylamino)-2-(4-(triisopropylsilyloxy)phenyl)butanoic acid (E305) in pyridine was added EDC, DMAP, and 6-AlQ, and the solution was stirred at room temperature overnight. The mixture was poured into NaHCO$_{3(sat)}$ and extracted with EtOAc. The combined organics were dried (Na$_2$SO$_4$), filtered, and evaporated. Column chromatography (SiO$_2$, 4% MeOH/CH$_2$Cl$_2$) gave pure tert-butyl 4-(isoquinolin-6-ylamino)-4-oxo-3-(4-(triisopropylsilyloxy)phenyl)butylcarbamate (E306).

Preparation of tert-butyl 3-(4-hydroxyphenyl)-4-(isoquinolin-6-ylamino)-4-oxobutylcarbamate (E307) was prepared from E306 according to the following:

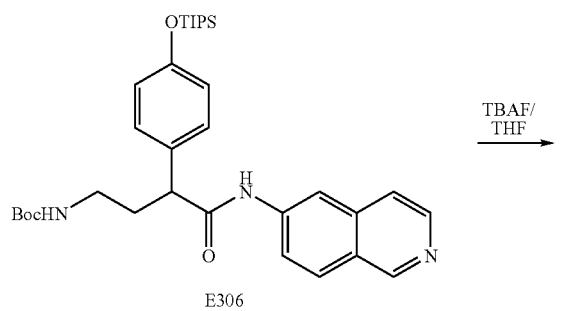

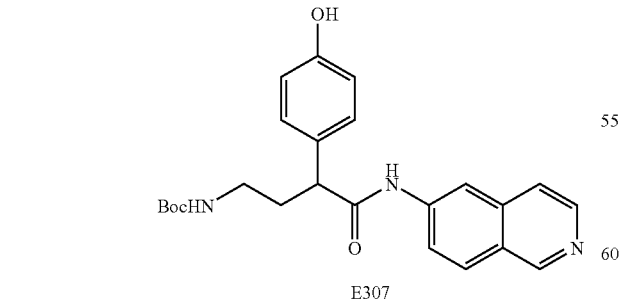

To tert-butyl 4-(isoquinolin-6-ylamino)-4-oxo-3-(4-(triisopropylsilyloxy)phenyl)butylcarbamate (E306) in THF at 0° C. was added TBAF and the solution was stirred at 0° C. for 30 min. The solution was poured into NH$_4$Cl$_{(sat)}$ and extracted with EtOAc. The combined organics were dried (Na$_2$SO$_4$), filtered, and evaporated. Column chromatography (SiO$_2$, 5-8% MeOH/CH$_2$Cl$_2$) gave pure tert-butyl 3-(4-hydroxyphenyl)-4-(isoquinolin-6-ylamino)-4-oxobutylcarbamate (E307).

Preparation of 4-amino-2-(4-hydroxyphenyl)-N-(isoquinolin-6-yl)butanamide dihydrochloride (E308) was prepared from E307 according to the below:

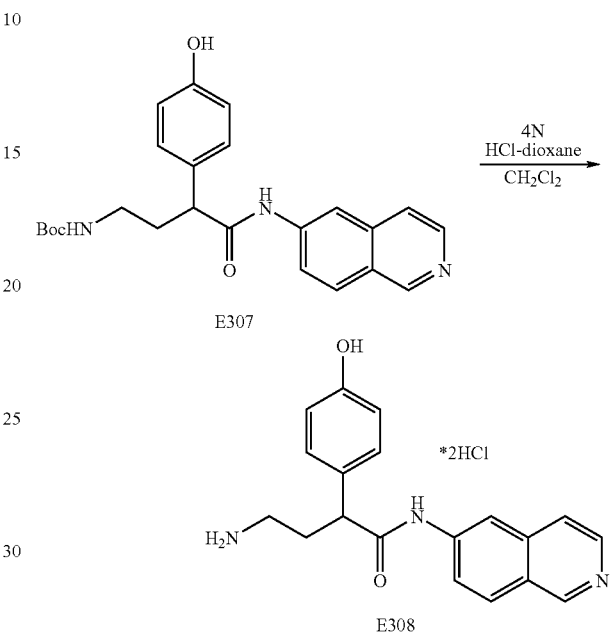

To tert-butyl 3-(4-hydroxyphenyl)-4-(isoquinolin-6-ylamino)-4-oxobutylcarbamate (E307) in CH$_2$Cl$_2$ was added HCl (4 N in dioxane) and 2 drops of H$_2$O and the solution was stirred overnight at room temperature. The solvents were evaporated to give 4-amino-2-(4-hydroxyphenyl)-N-(isoquinolin-6-yl)butanamide dihydrochloride (E308).

Examples 309-318

Using commercially available compounds and largely the procedures set forth in this application and substituting the appropriate starting materials E309-E318 could be synthesized.

TABLE 17

Compounds E309-E318.

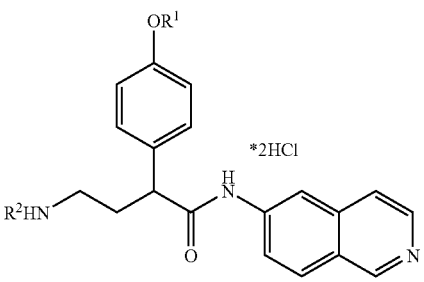

| Example | R1 | R2 |
|---|---|---|
| 309 | H | H |
| 310 | —CO-Ph | Me |

TABLE 17-continued

Compounds E309-E318.

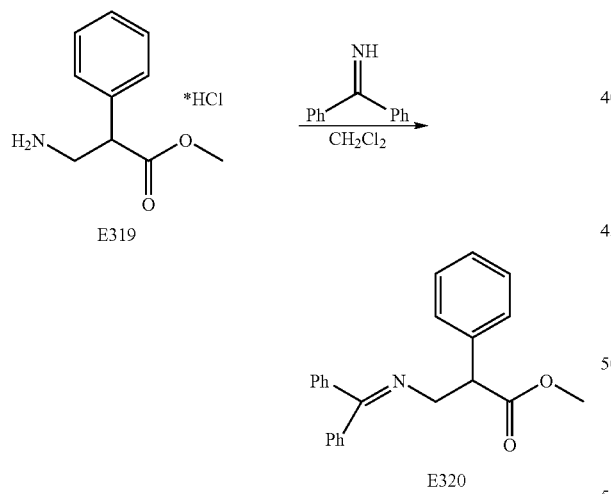

| Example | R1 | R2 |
|---|---|---|
| 311 | —CO-2,4-diMePh | H |
| 312 | —COCH$_2$Ph | H |
| 313 | —CO(CH$_2$)$_3$CH$_3$ | H |
| 314 | —CH$_2$COPh | Me |
| 315 | —CH$_2$CO-4-MeOPh | Me |
| 316 | —CH$_2$—CH(OH)—Ph | H |
| 317 | —CH$_2$-3-MeOPh | H |
| 318 | —(CH$_2$)$_2$Ph | Me |

Examples 319-325

Figure 18:
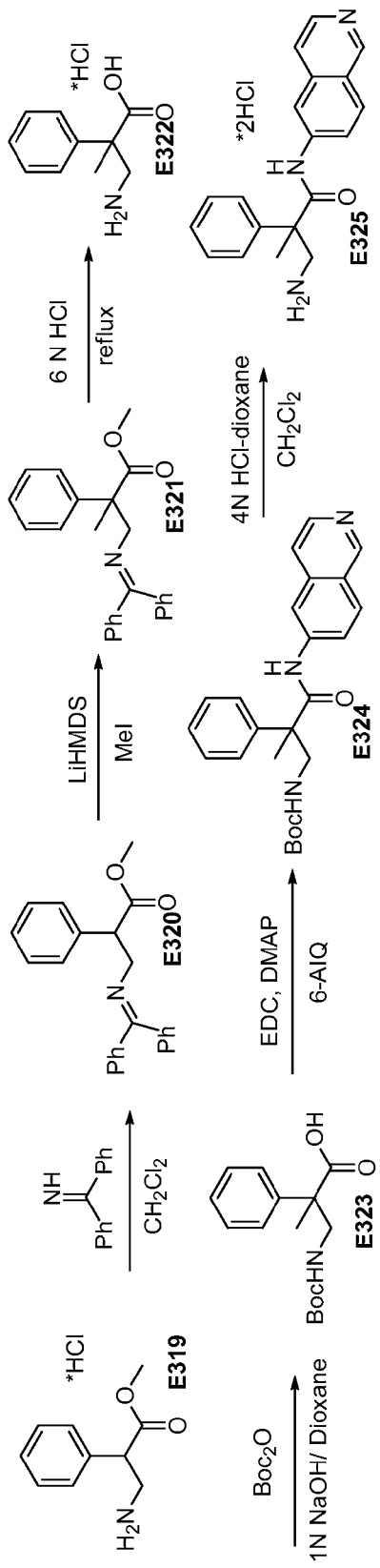
FIG. 18 is a scheme for the synthesis of compounds, including E319-E325.

Compounds E319-E325 were prepared according to the scheme in FIG. 18.

Preparation of methyl 3-(diphenylmethyleneamino)-2-phenylpropanoate (E320) was prepared from E319 according to the below:

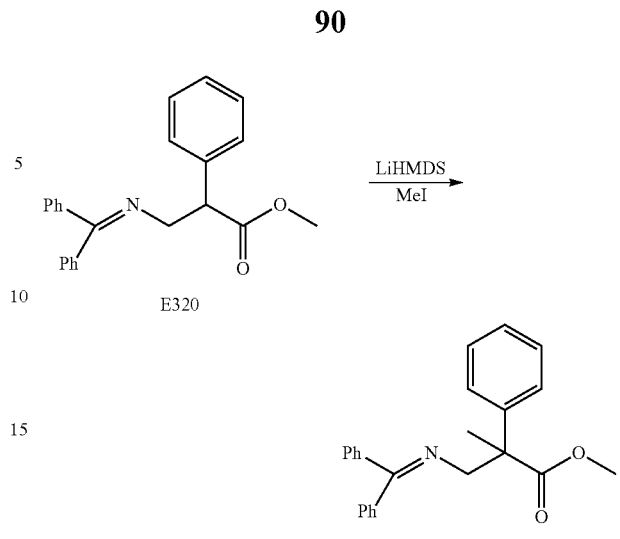

To methyl 3-amino-2-phenylpropanoate hydrochloride in CH$_2$Cl$_2$ was added benzophenone imine, and the solution was stirred overnight at room temperature. The mixture was then washed with H$_2$O and the organics were dried (Na$_2$SO$_4$), filtered, and evaporated. Column chromatography (SiO$_2$, 5-20% EtOAc/Hexanes) gave pure methyl 3-(diphenylmethyleneamino)-2-phenylpropanoate (E320).

Methyl 3-(diphenylmethyleneamino)-2-methyl-2-phenylpropanoate (E321) was prepared from E320 according to the below:

To a solution of LiHMDS in THF cooled to –78° C. was added a solution of methyl 3-(diphenylmethyleneamino)-2-phenylpropanoate (E320) in THF also cooled to approximately –78° C. This solution stirred for 30 min at –78° C., then methyl iodide was added directly and the solution was warmed to 0° C. After 3 h the solution was poured into NH$_4$Cl$_{(sat)}$ and extracted with EtOAc. The combined organics were dried (Na$_2$SO$_4$) filtered, and evaporated. Column chromatography (SiO$_2$, 0-15% EtOAc/Hexanes) gave pure methyl 3-(diphenylmethyleneamino)-2-methyl-2-phenylpropanoate (E321).

3-amino-2-methyl-2-phenylpropanoic acid hydrochloride (E322) was prepared from E321 according to the below:

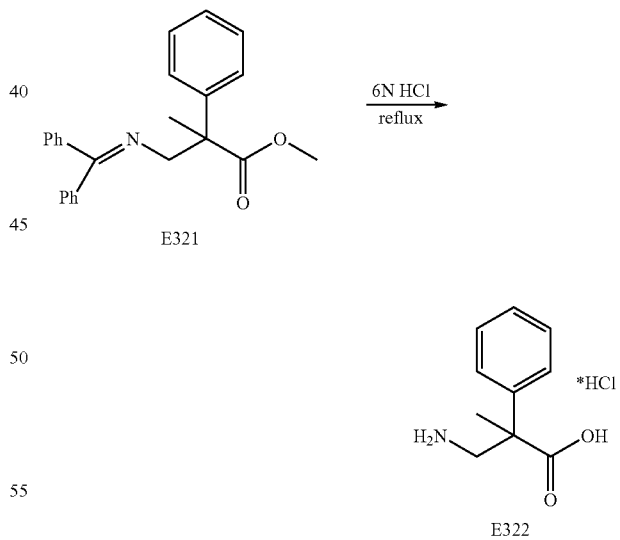

A mixture of methyl 3-(diphenylmethyleneamino)-2-methyl-2-phenylpropanoate (E321) and 6 N HCl was refluxed overnight. The solution was cooled and evaporated to give 3-amino-2-methyl-2-phenylpropanoic acid hydrochloride (E322).

3-(tert-butoxycarbonylamino)-2-methyl-2-phenylpropanoic acid (E323) was prepared from E322 according to the below:

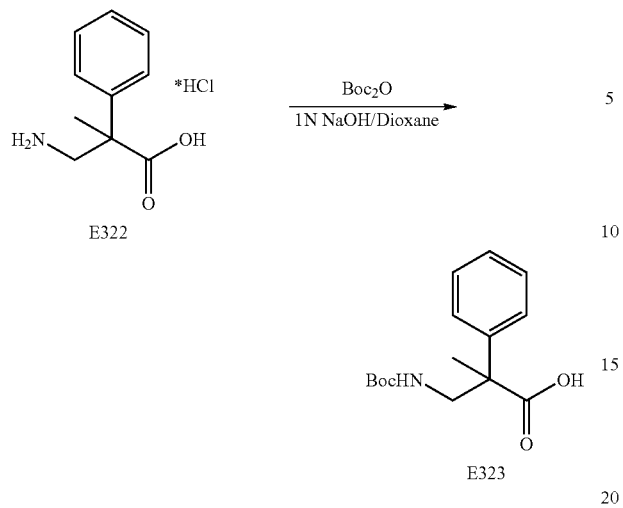

To a solution of Boc₂O in dioxane cooled to 0° C. was added a solution of 3-amino-2-methyl-2-phenylpropanoic acid hydrochloride (E322) in 1 N NaOH and this solution stirred 3 h and the solution was then washed with NaHCO$_{3(sat)}$/CH$_2$Cl$_2$. The aqueous layer was acidified with HCl (1 N) and extracted with CH$_2$Cl$_2$. These combined organics were dried (Na$_2$SO$_4$), filtered, and evaporated to give 3-(tert-butoxycarbonylamino)-2-methyl-2-phenylpropanoic acid (E323).

Tert-butyl 3-isoquinolin-6-yl)-2-methyl-3-oxo-2-phenylpropylcarbamate (E324) was prepared from E323 according to the below:

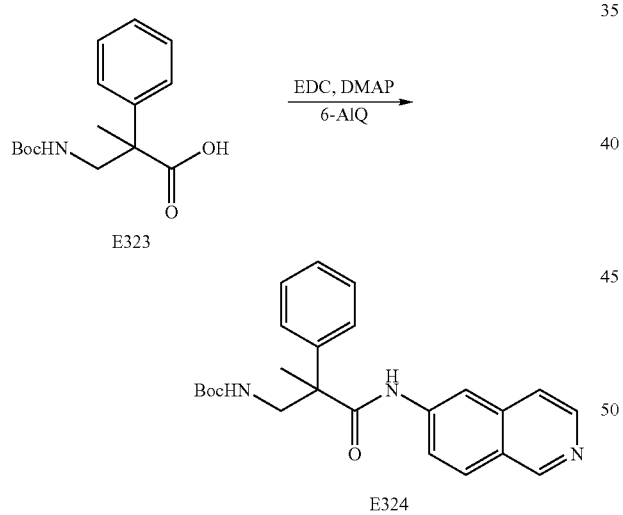

To 3-(tert-butoxycarbonylamino)-2-methyl-2-phenylpropanoic acid (E323) in pyridine was added EDC, DMAP, and 6-AlQ, and solution was stirred at room temperature for 48 h. The mixture was poured into NaHCO$_{3(sat)}$ and extracted with EtOAc. The combined organics were dried (Na$_2$SO$_4$), filtered, and evaporated. Column chromatography (SiO$_2$, 3% MeOH/CH$_2$Cl$_2$) gave pure tert-butyl 3-isoquinolin-6-yl)-2-methyl-3-oxo-2-phenylpropylcarbamate (E324).

3-amino-N-(isoquinolin-6-yl)-2-methyl-2-phenylpropanamide dihydrochloride (E325) was prepared from E324 according to the below:

To tert-butyl 3-isoquinolin-6-yl)-2-methyl-3-oxo-2-phenylpropylcarbamate (E324) in CH$_2$Cl$_2$ was added HCl (4 N in dioxane) and the solution was stirred overnight at room temperature. The solvents were evaporated to give 3-amino-N-(isoquinolin-6-yl)-2-methyl-2-phenylpropanamide dihydrochloride (E325).

Examples 326-334

Using commercially available compounds and largely the procedures set forth in the Examples above and substituting the appropriate starting materials, E326-E334 could be synthesized, shown in Table 18.

TABLE 18

Compounds E326-E334.

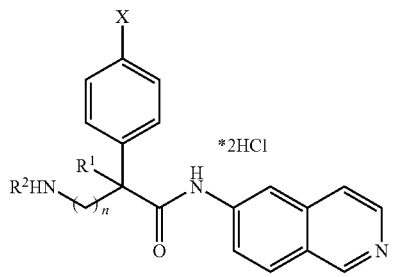

| Example | X | n | R1 | R2 |
|---|---|---|---|---|
| 326 | —OH | 1 | Me | Me |
| 327 | —CH$_2$OH | 1 | Me | H |
| 328 | —OCOPh | 2 | Me | H |
| 329 | —OCO-2,4-diMePh | 1 | —CH$_2$Ph | H |
| 330 | —OCOCH$_2$Ph | 1 | —CH$_2$Ph | H |
| 331 | —CH$_2$OCO-3,5-diMePh | 1 | Me | H |
| 332 | —CH$_2$OCO-2,4-diMePh | 1 | —CH$_2$-4-MeOPh | Me |
| 333 | —CH$_2$OCO-(CH$_2$)$_2$CH$_3$ | 1 | —CH$_2$-2-MeOPh | H |
| 334 | —CH$_2$OCO-2,4-diMePh | 2 | Me | H |

Examples 335-338

2-fluoro-4-nitrobenzamide (E335) was prepared according to the below:

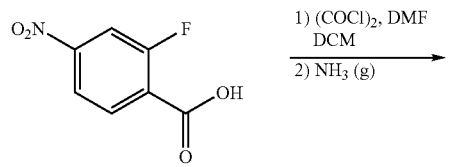

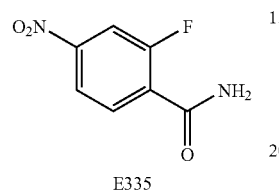

E335

To 2-fluoro-4-nitrobenzoic acid suspended in $CH_2Cl_2$ under Ar was added DMF then oxalyl chloride. The reaction was stirred at room temperature 1.5 h then the solvent was evaporated. The residue was dissolved in THF and ammonia gas was bubbled through the reaction for 15 min. The solvent was evaporated and the residue partitioned between EtOAc and water. The aqueous layer was extracted with EtOAc. The extracts were dried ($MgSO_4$), filtered, and evaporated. Column chromatography ($SiO_2$, 0-100% EtOAc/Hex) gave pure 2-fluoro-4-nitrobenzamide (E335).

4-amino-2-fluorobenzamide (E336) was prepared from E335 according to the below:

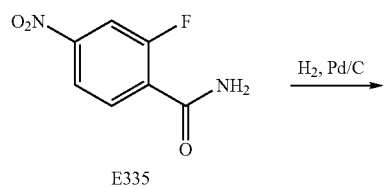

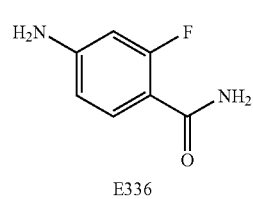

E336

2-fluoro-4-nitrobenzamide (E335) was dissolved in EtOH under Ar and 10% Pd/C added. The reaction was pump-purged with $H_2$ and left stirring at room temperature overnight. The catalyst was removed by filtration and the reaction concentrated to give pure 4-amino-2-fluorobenzamide (E336).

Tert-butyl 3-(4-carbamoyl-3-fluorophenylamino)-3-oxo-2-(4-((triisopropylsilyloxy)methyl)phenyl)propylcarbamate (E337) was prepared from E336 according to the below:

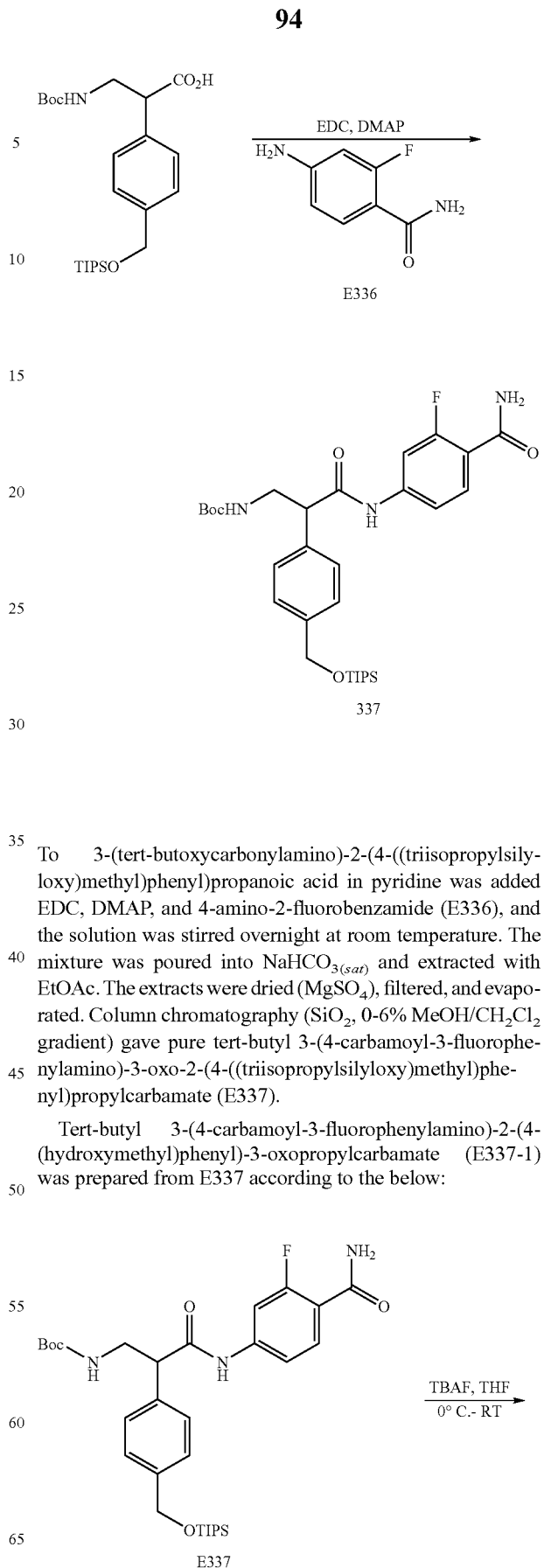

To 3-(tert-butoxycarbonylamino)-2-(4-((triisopropylsilyloxy)methyl)phenyl)propanoic acid in pyridine was added EDC, DMAP, and 4-amino-2-fluorobenzamide (E336), and the solution was stirred overnight at room temperature. The mixture was poured into $NaHCO_{3(sat)}$ and extracted with EtOAc. The extracts were dried ($MgSO_4$), filtered, and evaporated. Column chromatography ($SiO_2$, 0-6% $MeOH/CH_2Cl_2$ gradient) gave pure tert-butyl 3-(4-carbamoyl-3-fluorophenylamino)-3-oxo-2-(4-((triisopropylsilyloxy)methyl)phenyl)propylcarbamate (E337).

Tert-butyl 3-(4-carbamoyl-3-fluorophenylamino)-2-(4-(hydroxymethyl)phenyl)-3-oxopropylcarbamate (E337-1) was prepared from E337 according to the below:

-continued

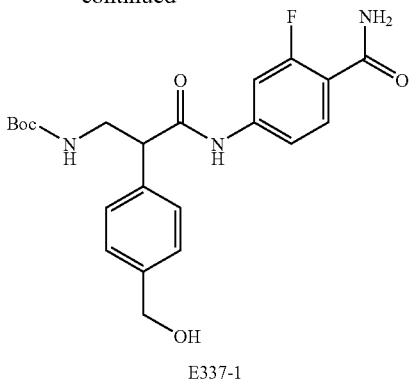

E337-1

To tert-butyl 3-(4-carbamoyl-3-fluorophenylamino)-3-oxo-2-(4-((thisopropylsilyloxy)methyl)phenyl)propylcarbamate (E337) in THF under $N_2$ at 0° C. was added TBAF, and the solution was stirred for 30 min at 0° C. The reaction was warmed to room temperature and stirred another 3.5 h. The compound was poured into EtOAc and washed with $NH_4Cl_{(sat)}$, dried ($MgSO_4$), filtered, and evaporated. Column chromatography ($SiO_2$, 0-20% MeOH/$CH_2Cl_2$ gradient) gave pure tert-butyl 3-(4-carbamoyl-3-fluorophenylamino)-2-(4-(hydroxymethyl)phenyl)-3-oxopropylcarbamate (E337-1)

4-(3-(tert-butoxycarbonylamino)-1-(4-carbamoyl-3-fluorophenylamino)-1-oxopropan-2-yl)benzyl 2,4-dimethylbenzoate (E337-2) was prepared from E337-1 according to the below:

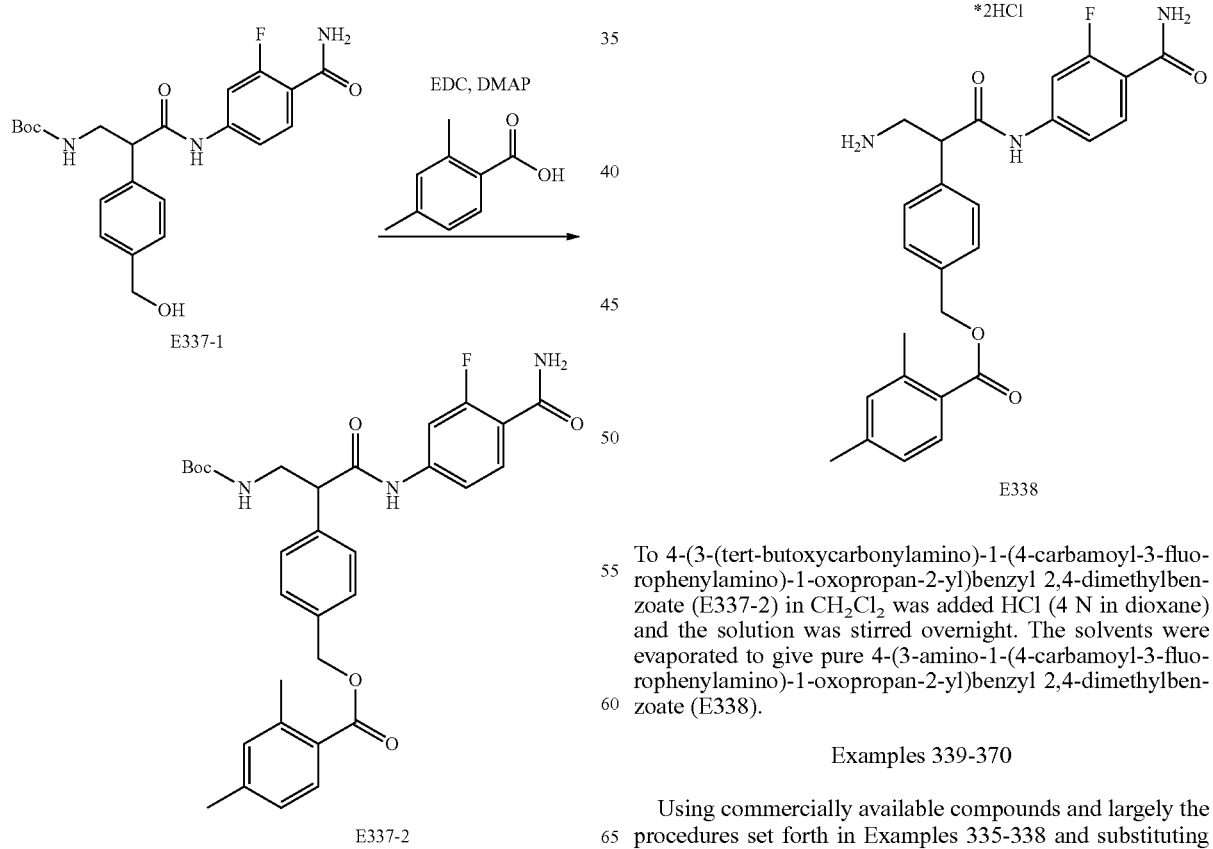

To tert-butyl 3-(4-carbamoyl-3-fluorophenylamino)-2-(4-(hydroxymethyl)phenyl)-3-oxopropylcarbamate (E337-1) in pyridine was added was added EDC, DMAP, and 2,4-dimethylbenzoic acid, and the solution was stirred overnight at room temperature. The mixture was poured into $NaHCO_{3(sat)}$ and extracted with EtOAc. The organics were dried ($MgSO_4$), filtered, and evaporated. Column chromatography ($SiO_2$, 0-5% MeOH/$CH_2Cl_2$ gradient) gave pure 4-(3-(tert-butoxycarbonylamino)-1-(4-carbamoyl-3-fluorophenylamino)-1-oxopropan-2-yl)benzyl 2,4-dimethylbenzoate (E337-2).

4-(3-amino-1-(4-carbamoyl-3-fluorophenylamino)-1-oxopropan-2-yl)benzyl 2,4-dimethylbenzoate (E338) was prepared from E337-2 according to the below:

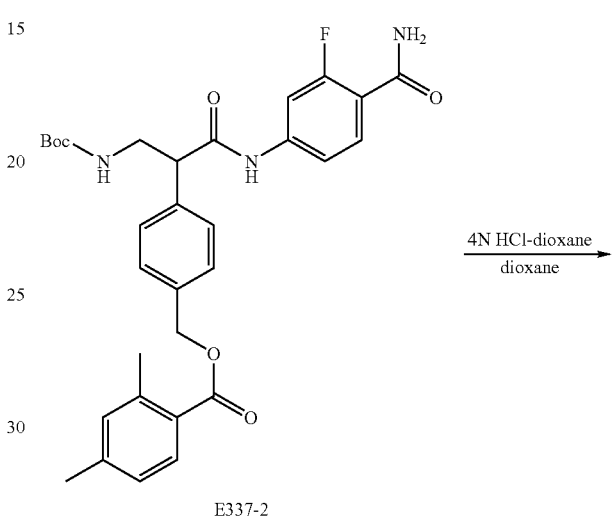

To 4-(3-(tert-butoxycarbonylamino)-1-(4-carbamoyl-3-fluorophenylamino)-1-oxopropan-2-yl)benzyl 2,4-dimethylbenzoate (E337-2) in $CH_2Cl_2$ was added HCl (4 N in dioxane) and the solution was stirred overnight. The solvents were evaporated to give pure 4-(3-amino-1-(4-carbamoyl-3-fluorophenylamino)-1-oxopropan-2-yl)benzyl 2,4-dimethylbenzoate (E338).

Examples 339-370

Using commercially available compounds and largely the procedures set forth in Examples 335-338 and substituting the appropriate starting materials, the compounds E339-E354 (Table 19) and E355-E370 (Table 20) could be made.

TABLE 19

Compounds E339-E354.

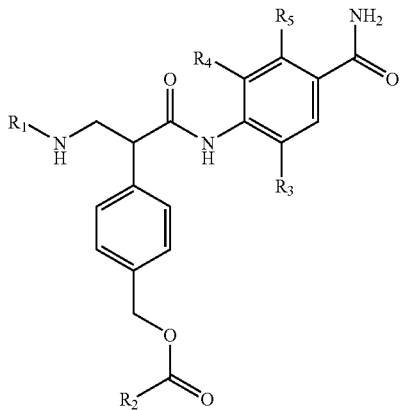

| Example | R1 | R2 | R3 | R4 | R5 |
|---|---|---|---|---|---|
| 339 | H | Bu | H | H | F |
| 340 | Me | Bu | H | H | F |
| 341 | H | Ph | H | H | H |
| 342 | Me | Ph | H | H | H |
| 343 | H | 3,5-diMePh | F | H | H |
| 344 | H | 2,4-diMePh | H | F | H |
| 345 | H | Bn | H | H | F |
| 346 | H | cyclohexyl | Me | H | H |
| 347 | Me | cyclopentyl | H | Me | H |
| 348 | Me | 3-MePh | H | H | Me |
| 349 | H | 4-MePh | H | H | H |
| 350 | H | 3-thienyl | H | H | H |
| 351 | Me | 2,4-diFPh | H | H | H |
| 352 | H | 3,5-diClPh | H | H | H |
| 353 | Me | 2-thienyl | H | H | H |
| 354 | H | 4-MeOPh | H | H | H |

TABLE 20

Compounds E355-E370.

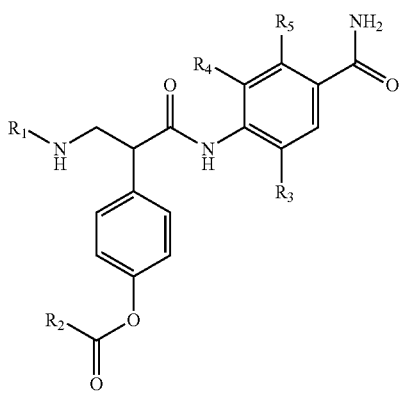

| Example | R1 | R2 | R3 | R4 | R5 |
|---|---|---|---|---|---|
| 355 | H | Bu | H | H | F |
| 356 | Me | Bu | H | H | F |
| 357 | H | Ph | H | H | H |
| 358 | Me | Ph | H | H | H |
| 359 | H | 3,5-diMePh | F | H | H |
| 360 | H | 2,4-diMePh | H | F | H |
| 361 | H | Bn | H | H | F |
| 362 | H | cyclohexyl | Me | H | H |
| 363 | Me | cyclopentyl | H | Me | H |
| 364 | Me | 3-MePh | H | H | Me |
| 365 | H | 4-MePh | H | H | H |
| 366 | H | 3-thienyl | H | H | H |
| 367 | Me | 2,4-diFPh | H | H | H |
| 368 | H | 3,5-diClPh | H | H | H |
| 369 | Me | 2-thienyl | H | H | H |
| 370 | H | 4-MeOPh | H | H | H |

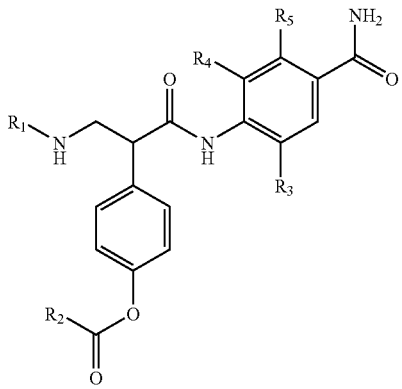

Examples 371-377

Figure 19:
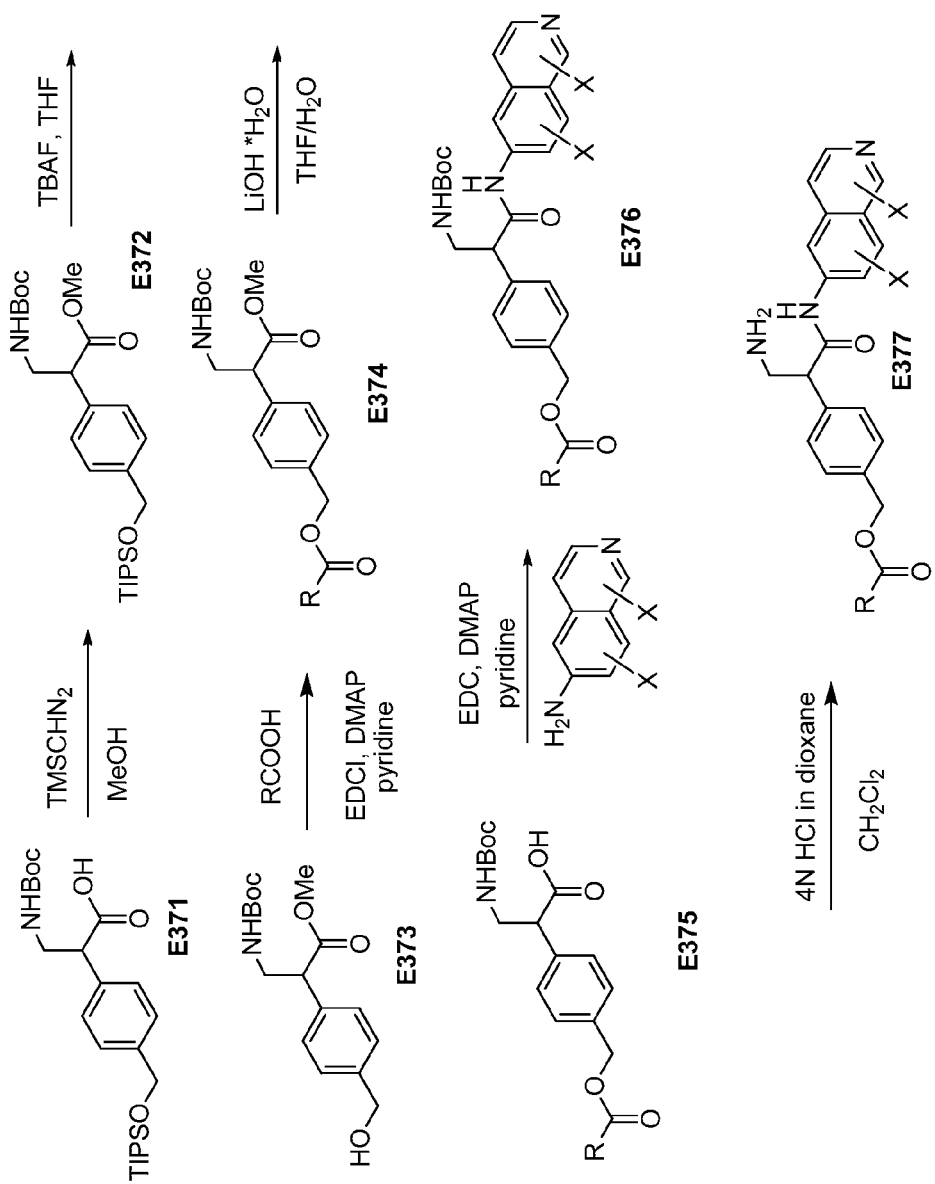
FIG. 19 is a scheme for the synthesis of compounds, including E371-E377.

Compounds E371-E377 were prepared according to the scheme in FIG. 19.

For the preparation of methyl 3-(tert-butoxycarbonylamino)-2-(4-((triisopropylsilyloxy)methyl)phenyl)propanoate (E372), to a 0° C. solution of methyl 3-(tert-butoxycarbonylamino)-2-(4-((triisopropylsilyloxy)methyl)phenyl) propanoic acid (E371) in MeOH was added a 2.0 M solution of trimethylsilyldiazomethane in hexanes. The solution was stirred for 20 min at room temperature and then quenched by the addition of a few drops of AcOH. The solution was concentrated and the residue, methyl 3-(tert-butoxycarbonylamino)-2-(4-((triisopropylsilyloxy)methyl)phenyl)propanoate (E372), was used without purification.

For the preparation of methyl 3-(tert-butoxycarbonylamino)-2-(4-(hydroxymethyl)phenyl)propanoate (E373), to a 0° C. solution of methyl 3-(tert-butoxycarbonylamino)-2-(4-((triisopropylsilyloxy)methyl)phenyl)propanoate (E372) in THF was added a 1 M solution of tetrabutylammonium fluoride in THF, and the reaction was stirred overnight at room temperature. The reaction was quenched with saturated aqueous $NH_4Cl$, and extracted with EtOAc (3×). The combined organics were washed with brine, dried over $Na_2SO_4$, and concentrated. The residue was purified by silica gel column chromatography (eluting with 0% to 50% EtOAc/hexanes) to yield methyl 3-(tert-butoxycarbonylamino)-2-(4-(hydroxymethyl)phenyl)propanoate (E373).

For the preparation of 4-(3-(tert-butoxycarbonylamino)-1-methoxy-1-oxopropan-2-yl)benzyl 2,4-dimethylbenzoate (E374, R=2,4-$Me_2$Ph), to a solution of methyl 3-(tert-butoxycarbonylamino)-2-(4-(hydroxymethyl)phenyl)propanoate (E373) in pyridine was added 1-[3-(dimethylamino)propyl]-3-ethylcarbodiimide hydrochloride (EDCl), 4-(dimethylamino)pyridine (DMAP), and 2,4-dimethylbenzoic acid. The reaction was stirred overnight at room temperature. After addition of EtOAc and saturated aqueous $NaHCO_3$, the mixture was extracted with EtOAc (3×). The combined organics were washed with brine, dried over $Na_2SO_4$, and concentrated. The residue was purified by silica gel column chromatography (eluting with 20% to 80% EtOAc/hexanes) to yield 4-(3-(tert-butoxycarbonylamino)-1-methoxy-1-oxopropan-2-yl)benzyl 2,4-dimethylbenzoate (E374, R=2,4-$Me_2$Ph).

For the preparation of 3-(tert-butoxycarbonylamino)-2-(4-((2,4-dimethylbenzoyloxy)methyl)phenyl)propanoic acid (E375, R=2,4-Me₂Ph), to a solution of 4-(3-(tert-butoxycarbonylamino)-1-methoxy-1-oxopropan-2-yl)benzyl 2,4-dimethylbenzoate (E374, R=2,4-Me₂Ph) in 2:1 THF/H₂O was added LiOH.H₂O and the solution was stirred at room temperature for 3 h. After addition of 1 N HCl (until the pH was acidic), the mixture was extracted with EtOAc (3×). The combined organics were washed with brine, dried over Na₂SO₄, filtered, and concentrated to yield 3-(tert-butoxycarbonylamino)-2-(4-((2,4-dimethylbenzoyloxy)methyl)phenyl)propanoic acid (E375, R=2,4-Me₂Ph).

For the preparation of 4-(3-(tert-butoxycarbonylamino)-1-(1-methoxyisoquinolin-6-ylamino)-1-oxopropan-2-yl)benzyl 2,4-dimethylbenzoate (E376, R=2,4-Me₂Ph, X=1-OMe), to a solution of 3-(tert-butoxycarbonylamino)-2-(4-((2,4-dimethylbenzoyloxy)methyl)phenyl)propanoic acid (E375, R=2,4-Me₂Ph) in pyridine was added EDCl, DMAP, and 6-amino-1-methoxyisoquinoline. The solution was stirred overnight at room temperature. The mixture was diluted with EtOAc and saturated aq. NaHCO₃ solution. The mixture was extracted with EtOAc (3×). The combined organics were washed with brine, dried over Na₂SO₄, and concentrated. The residue was purified by silica gel column chromatography (eluting with 0% to 80% EtOAc/hexanes) to yield 4-(3-(tert-butoxycarbonylamino)-1-(1-methoxyisoquinolin-6-ylamino)-1-oxopropan-2-yl)benzyl 2,4-dimethylbenzoate (E376, R=2,4-Me₂Ph, X=1-OMe).

For the preparation of 4-(3-amino-1-(1-methoxyisoquinolin-6-ylamino)-1-oxopropan-2-yl)benzyl 2,4-dimethylbenzoate (E377, R=2,4-Me₂Ph, X=1-OMe), to a solution of 4-(3-(tert-butoxycarbonylamino)-1-(1-methoxyisoquinolin-6-ylamino)-1-oxopropan-2-yl)benzyl 2,4-dimethylbenzoate (E376, R=2,4-Me₂Ph, X=3-Me) in CH₂Cl₂ was added 4N HCl in dioxane and the solution was stirred overnight at room temperature. The solution was concentrated. The residue was diluted with dichloromethane and concentrated again to yield 4-(3-amino-1-(1-methoxyisoquinolin-6-ylamino)-1-oxopropan-2-yl)benzyl 2,4-dimethylbenzoate (E377, R=2,4-Me₂Ph, X=2-OMe) as the hydrochloride salt.

Examples 378-380

Using largely the procedures shown above, the following compounds E378-E380 were synthesized, shown in Table 21.

TABLE 21

Compounds E378-E380.

| Example | R |
| --- | --- |
| 378 | 3-methylisoquinolin-6-yl |
| 379 | 1-methoxyisoquinolin-6-yl |
| 380 | 1-hydroxyisoquinolin-6-yl |

Examples 381-397

Using largely the procedures shown above, the following compounds E381-E397 could be synthesized, shown in Table 22.

TABLE 22

Compounds E381-E397.

| Example | R |
| --- | --- |
| 381 | 4-chloro-1-hydroxyisoquinolin-6-yl |
| 382 | 7-chloro-1-hydroxyisoquinolin-6-yl |

TABLE 22-continued
Compounds E381-E397.
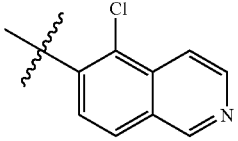 [SMILES: *c1ccc2cnccc2c1Cl]
| Example | R |
|---|---|
| 383 | 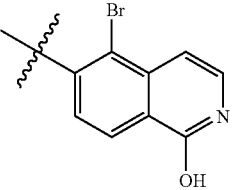 [SMILES: *c1ccc2c(O)nccc2c1Br] |
| 384 | 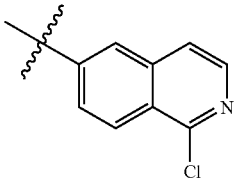 [SMILES: *c1ccc2c(Cl)nccc2c1] |
| 385 | 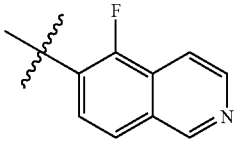 [SMILES: *c1ccc2cnccc2c1F] |
| 386 | 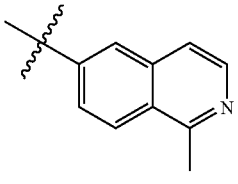 [SMILES: *c1ccc2c(C)nccc2c1] |
| 387 | 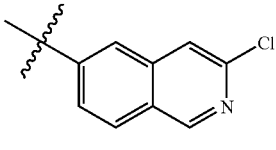 [SMILES: *c1ccc2cnc(Cl)cc2c1] |
| 388 | 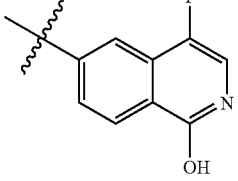 |
| 389 | 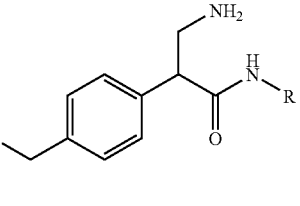 |
TABLE 22-continued
Compounds E381-E397.
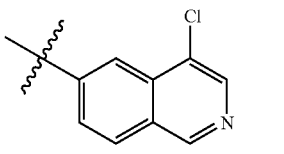 [SMILES: *c1ccc2cncc(F)c2c1]
| Example | R |
|---|---|
| 390 | 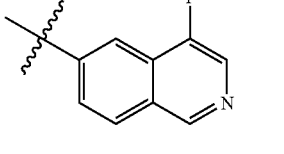 |
| 391 | 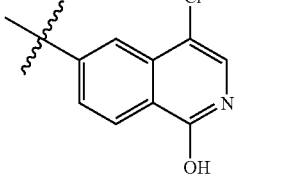 |
| 392 | 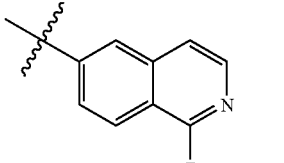 |
| 393 | 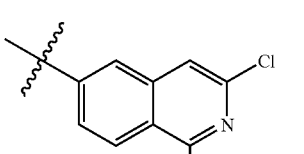 |
| 394 | 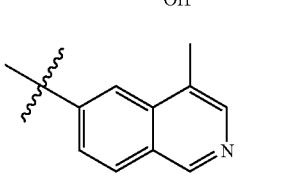 |
| 395 | 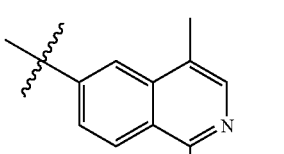 |
| 396 | 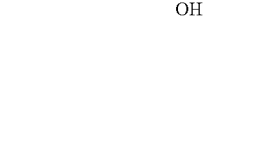 |

TABLE 22-continued

Compounds E381-E397.

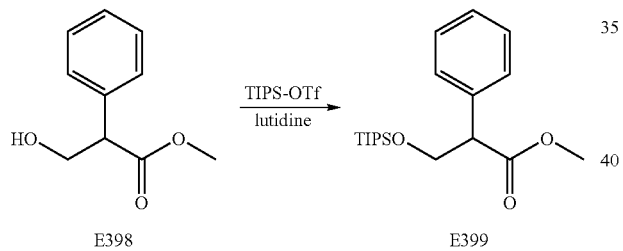

| Example | R |
|---|---|
| 397 | 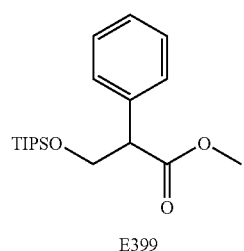 |

Examples 398-404

Figure 20:
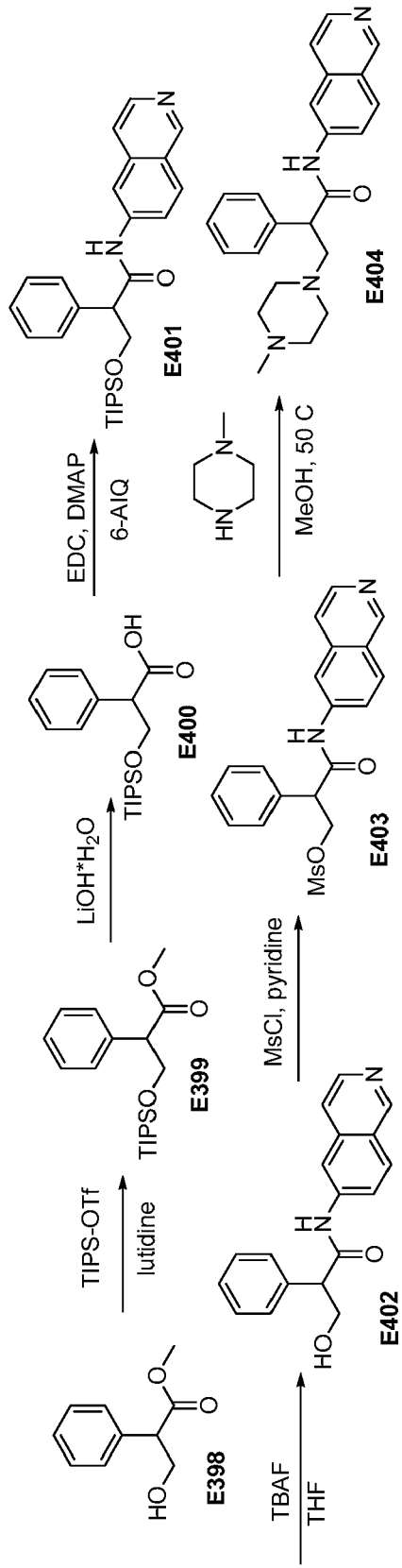
FIG. 20 is a scheme for the synthesis of compounds, including E398-E404.

Compounds E399-E404 were prepared according to the scheme in FIG. 20.

Methyl 2-phenyl-3-(triisopropylsilyloxy)propanoate (E399) was prepared from E398 according to the below:

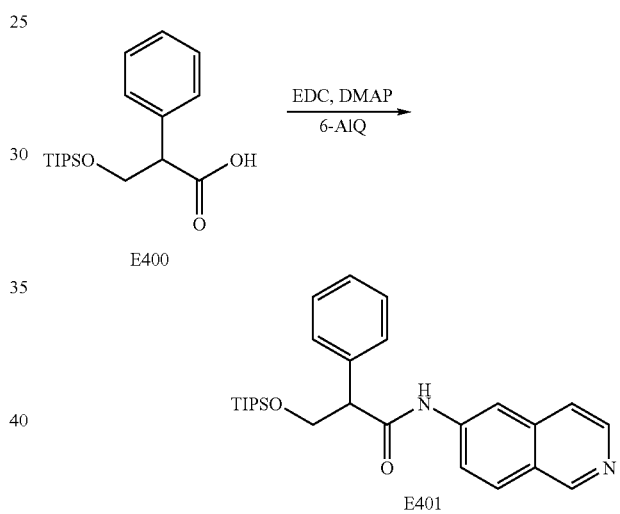

To methyl 3-hydroxy-2-phenylpropanolate in CH$_2$Cl$_2$ was at 0° C. was added 2,6-lutidine and TIPS-OTf, and this solution was stirred for 2 h at room temperature. The mixture was poured into NH$_4$Cl$_{(sat)}$ and extracted with CH$_2$Cl$_2$. The organics were dried (Na$_2$SO$_4$), filtered, and evaporated. Column chromatography 0-10% EtOAc/Hex gave pure methyl 2-phenyl-3-(triisopropylsilyloxy)propanoate (E399).

2-phenyl-3-(triisopropylsilyloxy)propanoic acid (E400) was prepared from E399 according to the below:

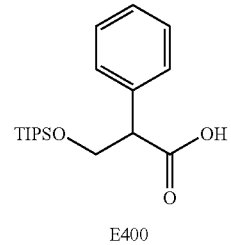

To methyl 2-phenyl-3-(triisopropylsilyloxy)propanoate (E399) in THF/H$_2$O/MeOH was added LiOH*H$_2$O and the solution was stir at room temperature overnight. The solution was poured into NH$_4$Cl$_{(sat)}$/HCl (1 N) (3:1) and extracted with EtOAc. The combined organics were dried (Na$_2$SO$_4$), filtered, and evaporated. Column chromatography (0%-4% MeOH/CH$_2$Cl$_2$) gave pure 2-phenyl-3-(triisopropylsilyloxy)propanoic acid (E400).

N-(isoquinolin-6-yl)-2-phenyl-3-(triisopropylsilyloxy)propanamide (E401) was prepared from E400 according to the below:

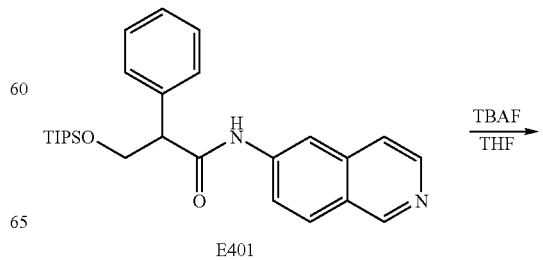

To 2-phenyl-3-(triisopropylsilyloxy)propanoic acid (E400) in pyridine was added EDC, DMAP, and 6-aminoisoquinoline, and the solution was flushed with N$_2$, capped, and stirred overnight. The mixture was poured into NaHCO$_{3(sat)}$ and extracted with EtOAC. The combined organics were dried (Na$_2$SO4), filtered, and evaporated. Column chromatography (3-4% MeOH/CH$_2$Cl$_2$) gave pure N-(isoquinolin-6-yl)-2-phenyl-3-(triisopropylsilyloxy)propanamide (E401).

3-hydroxy-N-(isoquinolin-6-yl)-2-phenylpropanamide (E402) was prepared from E401 according to the below:

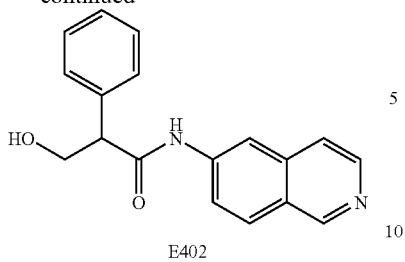

E402

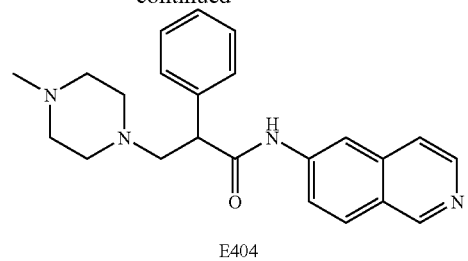

E404

To N-(isoquinolin-6-yl)-2-phenyl-3-(triisopropylsilyloxy) propanamide (E401) in THF cooled to 0° C. was added TBAF and this solution was stirred for 3 h at 0° C. The mixture was poured into EtOAc/NH$_4$Cl$_{(sat)}$ washed with NH$_4$Cl$_{(sat)}$. The organics were dried (Na$_2$SO$_4$), filtered, and evaporated. Column chromatography (0-10% MeOH/CH$_2$Cl$_2$) gave pure 3-hydroxy-N-(isoquinolin-6-yl)-2-phenylpropanamide (E402).

3-(isoquinolin-6-ylamino)-3-oxo-2-phenylpropyl methanesulfonate (E403) was prepared from E402 according to the below:

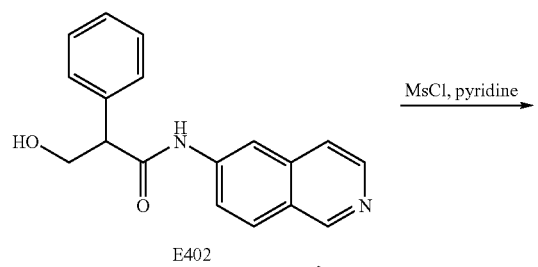

To 3-hydroxy-N-(isoquinolin-6-yl)-2-phenylpropanamide (E402) in pyridine at 0° C. was added MsCl, and this solution was stirred at 0° C. for 2.5 h. The mixture was poured into NaHCO$_{3(sat)}$ and extracted with EtOAc. The combined organics were dried (Na$_2$SO$_4$), filtered, and evaporated to give 3-(isoquinolin-6-ylamino)-3-oxo-2-phenylpropyl methanesulfonate (E403).

N-(isoquinolin-6-yl)-3-(4-methylpiperazin-1-yl)-2-phenylpropanamide (E404) was prepared from E403 according to the below:

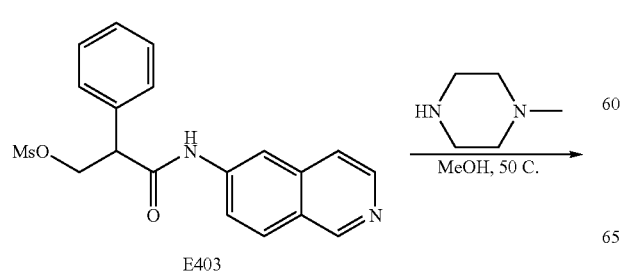

To 3-(isoquinolin-6-ylamino)-3-oxo-2-phenylpropyl methanesulfonate (E403) in methanol was added 1-methylpiperazine, and the solution was stirred overnight at 50° C. The solvents were evaporated and column chromatography 10-20% 2 N NH$_3$-MeOH/CH$_2$Cl$_2$ gave N-(isoquinolin-6-yl)-3-(4-methylpiperazin-1-yl)-2-phenylpropanamide (E404).

Examples 405-428

Using commercially available compounds and largely the procedures set forth in the previous examples and substituting the appropriate starting materials, the compounds E405-E410 (Table 23) and E411-E428 (Table 24 and Table 25) could be synthesized.

TABLE 23

Compounds E405-E410.

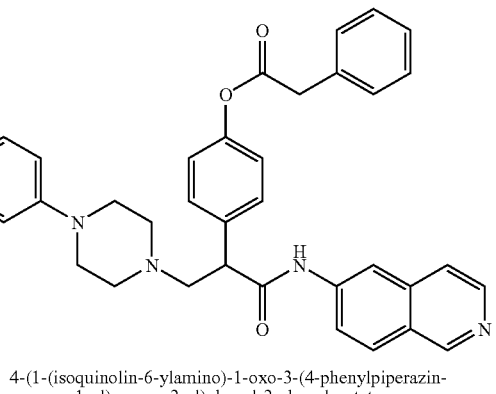

4-(1-(isoquinolin-6-ylamino)-1-oxo-3-(4-phenylpiperazin-1-yl)propan-2-yl)phenyl-2-phenylacetate

405

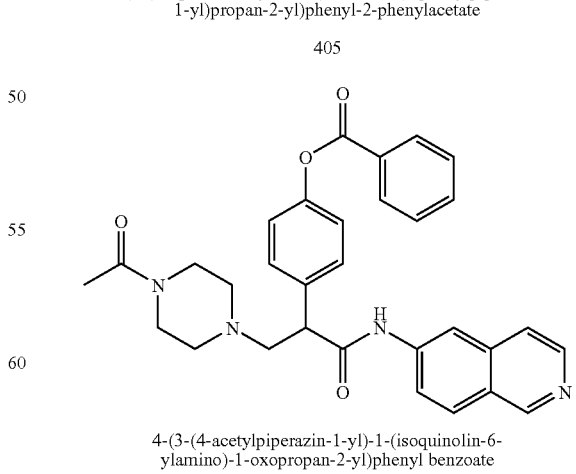

4-(3-(4-acetylpiperazin-1-yl)-1-(isoquinolin-6-ylamino)-1-oxopropan-2-yl)phenyl benzoate

406

TABLE 23-continued

Compounds E405-E410.

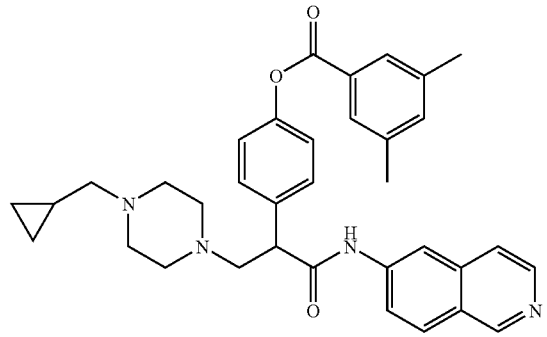

4-(3-(4-(cyclopropylmethyl)piperazin-1-yl)-1-(isoquinolin-6-
ylamino)-1-oxopropan-2-yl)phenyl 3,5-dimethylbenzoate

407

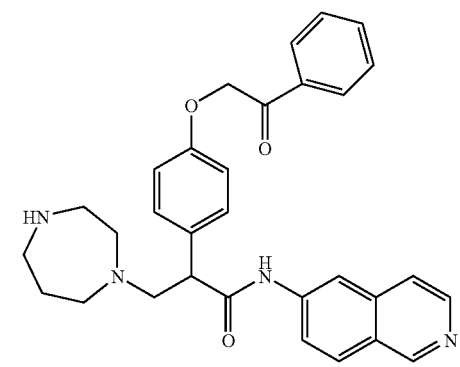

3-(1,4-diazepan-1-yl)-N-(isoquinolin-6-yl)-2-(4-
(2-oxo-2-phenylethoxy)phenyl)propanamide

408

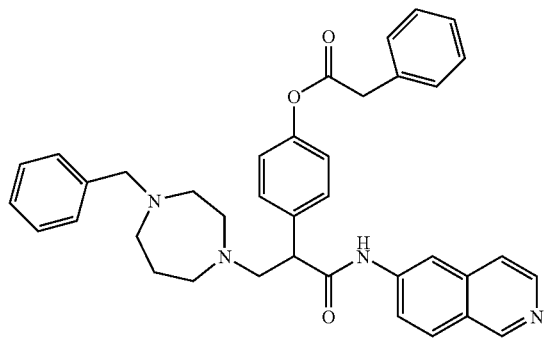

4-(3-(4-benzyl-1,4-diazepen-1-yl)-1-(isoquinolin-6-
ylamino)-1-oxopropan-2-yl)phenyl 2-phenylacetate

409

TABLE 23-continued

Compounds E405-E410.

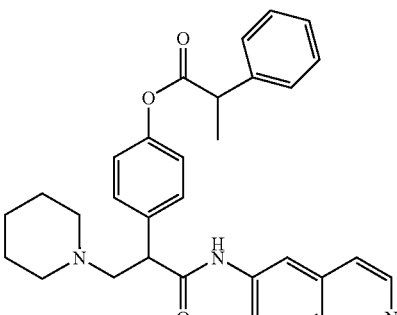

4-(1-(isoquinolin-6-ylamino)-1-oxo-3-(piperidin-
1-yl)propan-2-yl)phenyl 2-phenylpropanoate

410

TABLE 24

Compounds E411-E419.

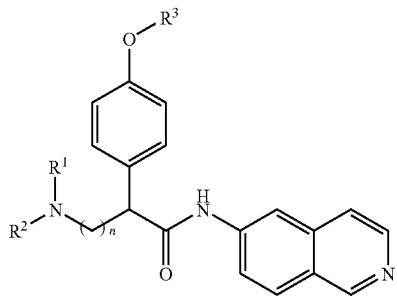

| Example | $R^1$ | $R^2$ | $R^3$ | n |
|---|---|---|---|---|
| 411 | Me | Me | CO-2,4diMePh | 1 |
| 412 | Me | Me | CO—CH2Ph | 1 |
| 413 | Me | $CH_2$-4-HOPh | CO—$(CH_2)_2CH_3$ | 1 |
| 414 | Me | $CH_2$-2-HOPh | $CH_2$—COPh | 1 |
| 415 | Me | $CH_2$-4-FPh | $CH_2$CO-4-MeOPh | 1 |
| 416 | Et | $CH_2$—Ph | $CH_2$C(OH)-2-MeOPh | 2 |
| 417 | Et | Me | $CH_2CH_2$Ph | 2 |
| 418 | Me | $CH_2$-3-pyridyl | COBn | 2 |
| 419 | Me | $CH_2$-4-pyridyl | COPh | 2 |

TABLE 25

Compounds E420-E428.

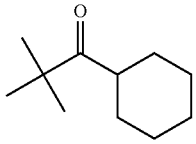

| Example | R¹ | R² | R³ | n |
|---|---|---|---|---|
| 420 | Me | Me | CO-2,4diMePh | 1 |
| 421 | Me | Me |  | 1 |
| 422 | Me | CH₂-4-MeOPh | CO—(CH2)2CH3 | 2 |
| 423 | Me | CH₂-2-HOPh | CO-4-MePh | 1 |
| 424 | Me | CH₂-3-FPh | COPh | 1 |
| 425 | Et | CH2—Ph | CO-3,5-diMePh | 2 |
| 426 | Et | Me | CO—Bn | 1 |
| 427 | Me | 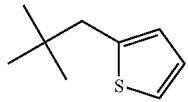 | CO(CH₂)₂CH3 | 2 |
| 428 | Me | CH₂-4-pyridyl | CO(CH₂)₂Ph | 1 |

Examples 429-433

Figure 21:
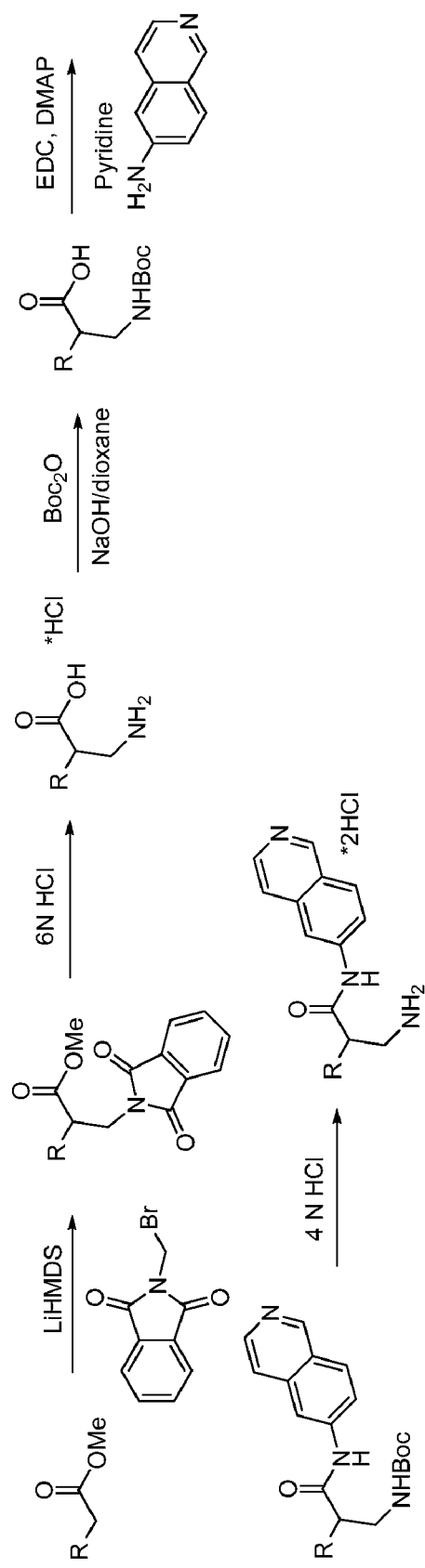
FIG. 21 is a general scheme for the synthesis of compounds, including compounds E429-E433.

Compounds E429-E433 were prepared according to the scheme in FIG. 21, which is a modified procedure of Calmes et al., *Eur. J. Org. Chem.* 2000, 2459-2466.

Methyl 3-(1,3-dioxoisoindolin-2-yl)-2-(thiophen-3-yl)propanoate (E429) was prepared according to the below:

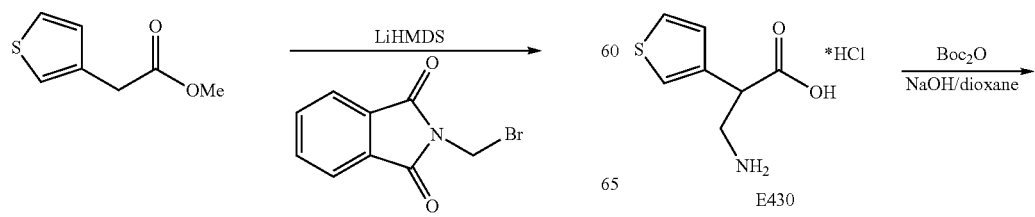

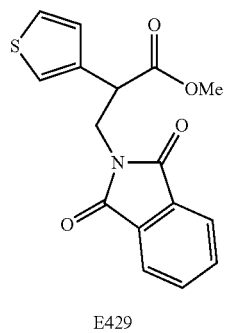

E429

To pure methyl 2-(thiophen-3-yl)acetate in THF cooled to −78° C. was added LiHMDS and the solution stirred at −78° C. for 30 min. Then N-(bromomethyl)phthalimide was added directly and the solution was allowed to warm to 0° C. The mixture was poured into NaHCO$_{3(sat)}$ extracted with EtOAc, dried (Na₂SO₄), filtered, and evaporated. Column chromatography (SiO₂, 0-40% EtOAc/Hex) gave pure methyl 3-(1,3-dioxoisoindolin-2-yl)-2-(thiophen-3-yl)propanoate (E429).

3-amino-2-(thiophen-3-yl)propanoic acid hydrochloride (E430) was prepared from E429 according to the below:

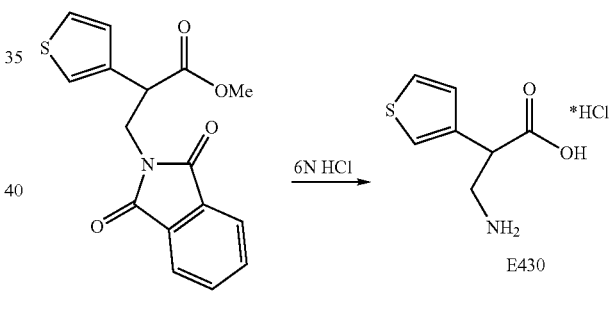

To methyl 3-(1,3-dioxoisoindolin-2-yl)-2-(thiophen-3-yl)propanoate (E429) was added 6 N HCl and the solution was refluxed for 4 h. The solvents were evaporated to give 3-amino-2-(thiophen-3-yl)propanoic acid (E430).

3-(tert-butoxycarbonylamino)-2-(thiophen-3-yl)propanoic acid (E431) was prepared from E430 according to the below:

-continued

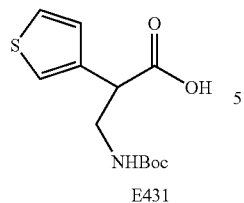
E431

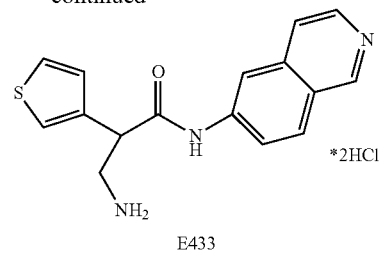
E433

To Boc₂O in dioxane at 0° C. was added a cooled solution (0° C.) of 3-amino-2-(thiophen-3-yl)propanoic acid hydrochloride (E430) in 1 N NaOH. The solution was stirred at 0° C. for 30 min, then at room temperature for 4 h. The mixture was acidified with HCl and extracted with EtOAc and NH₄Cl$_{(sat)}$. The organics were dried (Na₂SO₄), filtered, and evaporated to give pure of 3-(tert-butoxycarbonylamino)-2-(thiophen-3-yl)propanoic acid (E431).

Tert-butyl 3-(isoquinolin-6-ylamino)-3-oxo-2-(thiophen-3-yl)propylcarbamate (E432) was prepared from E431 according to the below:

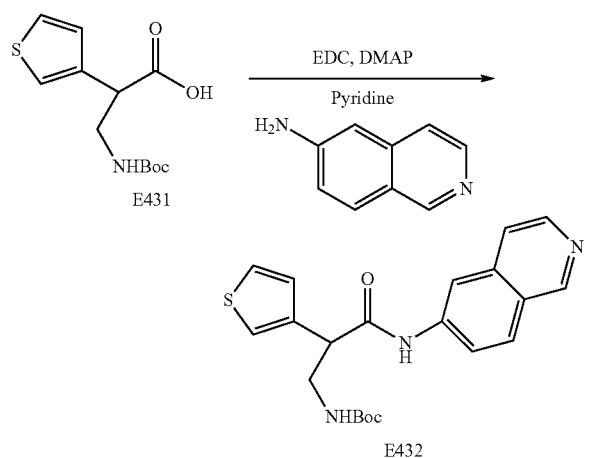

To 3-(tert-butoxycarbonylamino)-2-(thiophen-3-yl)propanoic acid (E431) in pyridine was added was added EDC, DMAP, and 6-aminoisoquinoline, and the solution was stirred overnight at room temperature. The mixture was poured into NaHCO₃$_{(sat)}$ and extracted with EtOAc. The organics were dried (Na₂SO₄), filtered, and evaporated. Column chromatography (SiO₂, 3% MeOH/CH₂Cl₂) gave pure tert-butyl 3-(isoquinolin-6-ylamino)-3-oxo-2-(thiophen-3-yl)propylcarbamate (E432).

3-amino-N-(isoquinolin-6-yl)-2-(thiophen-3-yl)propanamide dihydrochloride (E433) was prepared from E432 according to the below:

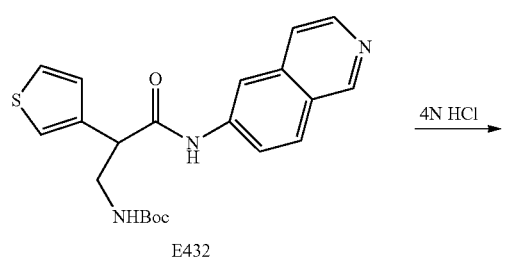

To tert-butyl 3-(isoquinolin-6-ylamino)-3-oxo-2-(thiophen-3-yl)propylcarbamate (E432) in CH₂Cl₂ was added HCl (4 N in dioxane) and the solution was stirred for 8-10 h. The solvents were evaporated to give pure 3-amino-N-(isoquinolin-6-yl)-2-(thiophen-3-yl)propanamide dihydrochloride (E433).

Examples 434-456

Using commercially available compounds and largely the procedures set forth in Examples 429-433 and substituting the appropriate starting materials, the following compounds E434-E441 (Table 26) and E442-E456 (Table 27) were made.

TABLE 26

Compounds E434-E441.

| Example | X  | R₄            | R₂     | R₁     |
|---------|----|---------------|--------|--------|
| 434     | H  | (±)-3-thienyl | Me     | Me     |
| 435     | H  | (±)-3-thienyl | H      | H      |
| 436     | H  | C₆H₅          | H      | H      |
| 437     | H  | C₆H₅          | Me     | Me     |
| 438     | F  | C₆H₅          | H      | H      |
| 439     | F  | C₆H₅          | Me     | Me     |
| 440     | H  | (±)-2-thienyl | H      | H      |
| 441     | Cl | (±)-2-thienyl | Me     | Me     |

TABLE 27

Compounds E442-E456.

| Example | X  | R₄              | R₂     | R₁ |
|---------|----|-----------------|--------|----|
| 442     | H  | (R)-C₆H₅        | H      | H  |
| 443     | H  | (S)-C₆H₅        | H      | H  |
| 444     | OH | p-fluoro-C₆H₄   | Me     | Me |
| 445     | H  | p-fluoro-C₆H₄   | benzyl | H  |

TABLE 27-continued

Compounds E442-E456.

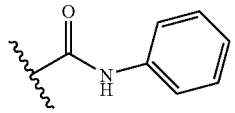 [SMILES: *C(=O)Nc1ccccc1]

| Example | X | R$_4$ | R$_2$ | R$_1$ |
|---|---|---|---|---|
| 446 | H | Benzyl | Me | H |
| 447 | H | p-fluoro benzyl | Me | H |
| 448 | OH | 3-pyridyl | H | H |
| 449 | H | 4-pyridyl | Me | Me |
| 450 | OH | 3-furyl | H | H |
| 451 | H | cyclopropyl | Me | Me |
| 452 | H | cyclopentyl | Me | Me |
| 453 | OH | cyclohexyl | H | H |
| 454 | H | 3-benzo[b]thiophene | Me | Me |
| 455 | H | ![structure] | H | H |
| 456 | OH | 2-oxazole | H | H |

Example 457

Topical pharmaceutical compositions for lowering intraocular pressure are prepared by conventional methods and formulated as follows:

| Ingredient | Amount (wt %) |
|---|---|
| Active ingredient | 0.50 |
| Dextran 70 | 0.1 |
| Hydroxypropyl methylcellulose | 0.3 |
| Sodium chloride | 0.77 |
| Potassium chloride | 0.12 |
| Disodium EDTA | 0.05 |
| Benzalkonium chloride | 0.01 |
| HCl and/or NaOH | pH 5.5-6.5 |
| Purified water | q.s. to 100% |

A compound according to this invention is used as the active ingredient. When the composition is topically administered to the eyes once daily, the above composition decreases intraocular pressure in a patient suffering from glaucoma.

Example 458

Example 457 is repeated using E6 according to this invention. When administered as a drop 2 times per day, the above composition substantially decreases intraocular pressure and serves as a neuroprotective agent.

Example 459

Example 457 is repeated using a gamma amino acid isoquinolyl amide according to this invention. When administered as a drop twice per day, the above composition substantially decreases intraocular pressure.

Example 460

Example 457 is repeated using a benzamide according to this invention. When administered as a drop twice per day, the above composition substantially decreases allergic symptoms and relieves dry eye syndrome.

Example 461

Example 457 is repeated using E19 according to this invention. When administered as a drop as needed, the above composition substantially decreases hyperemia, redness, and ocular irritation.

Example 462

Example 457 is repeated using E18 according to this invention. When administered as a drop 4 times per day, the above composition substantially decreases intraocular pressure and serves as a neuroprotective agent.

Example 463

Example 457 is repeated using E21 according to this invention. When administered as a drop twice per day, the above composition substantially decreases intraocular pressure.

Example 464

Example 457 is repeated using E115 according to this invention. When administered as a drop twice per day, the above composition substantially decreases ocular pressure, allergic symptoms, and relieves dry eye syndrome.

Reference Example 2

Cell-Based Porcine Trabecular Meshwork (PTM) Assay

The anterior section of porcine eyes are harvested within 4 h post-mortem. The iris and ciliary body are removed and trabecular meshwork cells are harvested by blunt dissection. Finely minced trabecular meshwork tissue are plated into collagen-coated 6-well plates in Medium-199 containing 20% fetal bovine serum (FBS). After two passages at confluence, cells are transferred to low-glucose DMEM containing 10% FBS. Cells are used between passage 3 and passage 8.

Cells are plated into fibronectin-coated, glass multiwell plates the day before compound testing under standard culture conditions. Compounds are added to cells in the presence of 1% FBS-containing DMEM and 1% DMSO. When compounds are incubated with the cells for the duration determined to be optimal, the media and compound is removed and cells fixed for 20 min in 3% methanol-free paraformaldehyde. Cells are rinsed twice with phosphate buffered saline (PBS) and cells are permeabilized with 0.5% Triton X-100 for two min. Following an additional two washes with PBS, F-actin is stained with Alexa-fluor 488-labelled phalloidin and nuclei are stained with DAPI.

Data is reduced to the mean straight actin-fiber length and normalized to DMSO-treated control cells (100%) and 50 µM Y-27632 (0%). Y-27632 is a rho-kinase inhibitor known to result in the depolymerization of F-actin in these cells.

Reference Example 3

Norepinephrine Transporter (NET) Membrane Radioligand Binding Assays

Total cell membranes are prepared from MDCK cells expressing the recombinant human norepinehrine transporter (hNET) grown to confluence in 150 mm tissue culture dishes. Cells are scraped into standard medium and pelleted at 1600 g. The medium is discarded and the pellet resuspended in 5 mL per plate of ice-cold binding buffer (100 mM NaCl, 50 mM Tris, pH 7.4 at room temperature) by trituration, and the cells are repelleted at 20,000 g. Supernatant is discarded and cells are resuspended in binding buffer (50 mM Tris-HCl, pH 7.4, 100 mM NaCl, 1 µM leupeptin, 10 µM PMSF) and homogenized with a polytron (Brinkman) at 25,000 revs/min for 5 s. Centrifugation, resuspension, and homogenization are repeated and a sample of suspension is used for Bradford protein determination (BioRad). Samples of membrane suspensions are frozen at −80° C. prior to use. Typical yields are about 100 µg membrane protein per 106 cells. Assays performed in duplicate are initiated with 0.2 nM [125I]RTI-55. Non-specific binding is determined by the inclusion of 10 µM desipramine. Incubation is carried out for 3 h at 4° C. Assays are terminated by rapid filtration over GF/B glass-fiber filters soaked in 0.5% polyethylineimine using an automated cell harvester (Brandel) followed by three rapid 5 mL washes in ice-cold binding buffer. Bound radioactivity is measured by gamma emission spectrometry.

Reference Example 4

Serotonin Transporter (SERT) Membrane Radioligand Binding Assays

Total cell membranes are prepared from HEK-293 cells expressing the recombinant human serotonin transporter (hSERT) grown to confluence in 150 mm tissue culture dishes. Cells are scraped into standard medium and pelleted at 1600 g. The medium is discarded and the pellet resuspended in 5 mL per plate of ice-cold binding buffer (100 mM NaCl, 50 mM Tris, pH 7.4 at room temperature) by trituration, and the cells are repelleted at 20,000 g. Supernatant is discarded and cells are resuspended in binding buffer (50 mM Tris-HCl, pH 7.4, 120 mM NaCl, 5 mM KCl) and homogenized with a polytron (Brinkman) at 25,000 revs/min for 5 s. Centrifugation, resuspension, and homogenization are repeated, and a sample of suspension is used for Bradford protein determination (BioRad). Samples of membrane suspensions are frozen at −80° C. prior to use. Typical yields are about 100 µg membrane protein per 106 cells. Assays performed in duplicate are initiated with 0.4 nM [3H]paroxetine. Non-specific binding is determined by the inclusion of 10 µM imipramine. Incubation is carried out for 60 min at 25° C. Assays are terminated by rapid filtration over GF/B glass-fiber filters soaked in 0.5% polyethylineimine using an automated cell harvester (Brandel) followed by three rapid 5 mL washes in ice-cold binding buffer. Bound radioactivity is measured by beta emission spectrometry.

Reference Example 5

Pharmacological Activity for Glaucoma Assay

Pharmacological activity for glaucoma treatment can be demonstrated using assays designed to test the ability of the subject compounds to decrease intraocular pressure. Examples of such assays are described in the following reference, incorporated herein by reference: C. Liljebris, G. Selen, B. Resul, J. Sternschantz, and U. Hacksell, "Derivatives of 17-phenyl-18,19,20-trinorprostaglandin $F_2$ Ispropyl Ester: Potential Anti-glaucoma Agents", *Journal of Medicinal Chemistry* 1995, 38 (2): 289-304.

Reference Example 6

Functional Screen for NET Activity Modulators

At the center of the cellular assay used to characterized inhibition of the human norepinephrine transporter (hNET) is a fluorophore which mimics a biogenic amine and is actively transported in to the cell. After incubation with a potential inhibitor, the dye solution is added in the presence of a fluorescence masking dye. When the fluorescent dye is transported into the cell and removed from the masking dye, light is emitted at a wavelength of 510 nm when excited with light of 425 nm. Inhibitors of the norepinephrine transporter prevent this time-dependent increase in fluorescence. (Blakely R D, DeFelice L J, and Galli A. A. *Physiol*. 2005. 20,225-231).

HEK-293 cells recombinantly over-expressing the human Norepinephrine Transporter are grown in phenol red-free DMEM medium (Gibco #21063-029) containing 10% fetal bovine serum (Atlanta Biologicals #S11050), 100 units/mL penicillin/streptomycin (Gibco #15140-122), and 250 µg/mL G-418 (Gibco #10131027) at 37° C. and 5% $CO_2$.

One day prior to testing, cells are plated into black, clear bottom plates (Costar #3904) at a density of 100,000 per well. On the morning of the assay, culture media is removed and replaced with 100 µL of HBSS (1× Hank's Balanced Salt Solution containing 20 mM HEPES) (10× HBSS Gibco #14065, 1 M HEPES Gibco #15630-80) containing test compound. Cells are exposed to the test compound (or DMSO in control wells) for 30 min. At the end of the pre-incubation period, 10 µL of 10× dye solution is added and thoroughly mixed with the compound solution. After a 30 min incubation period, fluorescence is quantified using an Analyst HT fluorescence plate reader (Molecular Devices, Sunnyvale, Calif.).

While the invention has been described in detail and with reference to specific embodiments thereof, it will be apparent to one skilled in the art that various changes and modifications can be made without departing from the spirit and scope of the invention.

What is claimed is:
1. A compound according to Formula I:

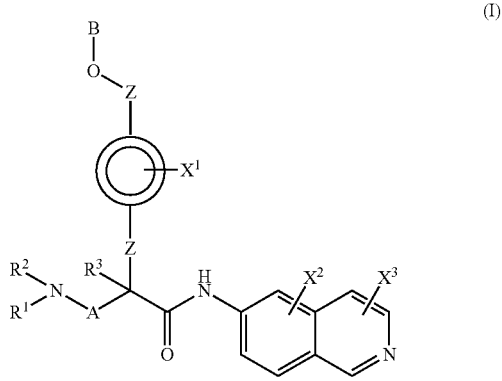

and salts thereof, wherein $R^1$, $R^2$, and $R^3$ are independently hydrogen, $C_1$-$C_4$ alkyl, aryl, $C_1$-$C_4$ alkyl aryl, $C_1$-$C_4$ alkyl heteroaryl, $C_1$-$C_4$ alkyl heterocyclyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, $C_1$-$C_4$ carboxyl, or form a ring with each other or with A;

wherein A is $C_1$-$C_4$ alkyl, $C_1$-$C_4$ alkyl aryl, $C_1$-$C_4$ alkyl heteroaryl, or forms a ring structure with $R^1$, $R^2$ or $R^3$;

wherein B is hydrogen, an aryl group, a heteroaryl group, a cycloalkyl group, a heterocycloalkyl group, $C_1$-$C_{22}$ alkyl, $C_1$-$C_{22}$ alkyl aryl, $C_1$-$C_{22}$ alkyl heteroaryl, $C_2$-$C_{22}$ alkenyl, $C_2$-$C_{22}$ alkynyl, $C_1$-$C_{22}$ carbonyl, $C_1$-$C_{22}$ carbonylamino, $C_1$-$C_{22}$ alkoxy, $C_1$-$C_{22}$ sulfonyl, $C_1$-$C_{22}$ sulfonylamino, $C_1$-$C_{22}$ thioalkyl, or $C_1$-$C_{22}$ carboxyl;

wherein $X^1$, $X^2$, and $X^3$ are, independently, hydrogen, hydroxyl, halogen, $C_1$-$C_4$ alkyl, $C_2$-$C_4$ alkenyl, $C_2$-$C_4$ alkynyl, amino, aminocarbonyl, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl;

wherein the double circle

indicates an aromatic or heteroaromatic ring; and
wherein each Z is independently a bond, is $C_1$-$C_4$ alkyl, heteroalkyl, or an O atom.

2. A compound according to claim 1, wherein $R^1$ and $R^2$ are methyl or hydrogen, and wherein $X^1$, $X^2$, and $X^3$ are hydrogen.

3. A compound according to claim 1, wherein B is an aliphatic carbonyl group.

4. A compound according to claim 1, wherein B is a benzoic, pyridyl, naphthyl, benzothiophene, or thiazole carbonyl group.

5. A compound according to claim 1, wherein Z is a bond or —$CH_2$—.

6. A compound according to claim 1, wherein $X^1$, $X^2$ and $X^3$ are each hydrogen.

7. A compound according to claim 1, wherein A is —$CH_2CH_2$—.

8. A compound according to claim 1, wherein $R^1$ and $R^2$ are independently hydrogen or methyl.

9. A compound according to claim 1, wherein $R^3$ is hydrogen or $C_1$-$C_4$ alkyl.

10. A compound according to Formula III:

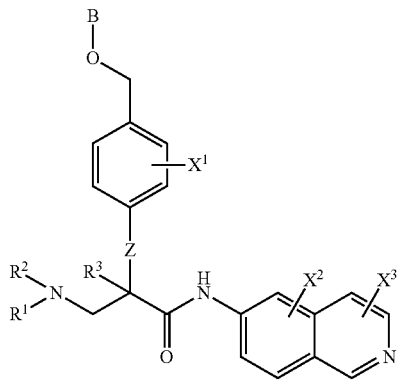

(III)

and salts and solvates thereof, wherein $R^1$ and $R^2$ are independently hydrogen, $C_1$-$C_4$ alkyl, $C_1$-$C_4$ alkyl aryl, $C_1$-$C_4$ alkyl heteroaryl, $C_1$-$C_4$ alkyl heterocyclyl, or $R^1$ and $R^2$ together form a ring, either cycloalkyl or heterocycloalkyl;

wherein $R^3$ is hydrogen, $C_1$-$C_4$ alkyl, $C_1$-$C_4$ alkyl aryl, $C_1$-$C_4$ alkyl heteroaryl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl, or $R^3$ may from a ring with itself or $R^1$ or $R^2$;

wherein $X^1$, $X^2$, and $X^3$ are, independently, hydrogen, hydroxyl, halogen, $C_1$-$C_4$ alkyl, $C_2$-$C_4$ alkenyl, $C_2$-$C_4$ alkynyl, amino, aminocarbonyl, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl;

wherein B is hydrogen, $C_1$-$C_{18}$ alkyl, $C_1$-$C_{18}$ alkyl aryl, $C_1$-$C_{18}$ alkyl heteroaryl, $C_1$-$C_{18}$ carbonyl, $C_1$-$C_{18}$ carbonylamino, $C_1$-$C_{18}$ sulfonyl, $C_1$-$C_{18}$ sulfonylamino, or $C_1$-$C_{18}$ carboxyl; and wherein each Z is independently a bond, is $C_1$-$C_4$ alkyl, heteroalkyl, or an O atom.

11. A compound according to Formula IV:

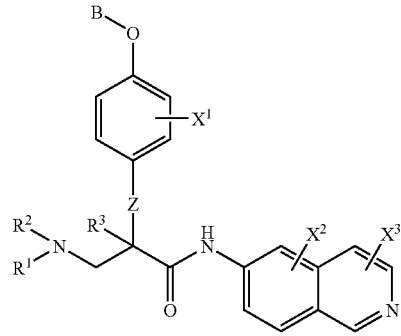

(IV)

and salts thereof, wherein $R^1$ and $R^2$ are independently hydrogen, $C_1$-$C_4$ alkyl, $C_1$-$C_4$ alkyl aryl, $C_1$-$C_4$ alkyl heteroaryl, $C_1$-$C_4$ alkyl heterocyclyl, or $R^1$ and $R^2$ together form a ring, either cycloalkyl or heterocyclyl;

wherein $R^3$ is a hydrogen, $C_1$-$C_4$ alkyl, $C_1$-$C_4$ alkyl aryl, $C_1$-$C_4$ alkyl heteroaryl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl;

wherein $X^1$, $X^2$, and $X^3$ are, independently, hydrogen, hydroxyl, halogen, $C_1$-$C_4$ alkyl, $C_2$-$C_4$ alkenyl, $C_2$-$C_4$ alkynyl, amino, aminocarbonyl, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl, or $C_1$-$C_4$ carboxyl;

wherein B is hydrogen, $C_1$-$C_{18}$ alkyl, $C_1$-$C_{18}$ alkyl aryl, $C_1$-$C_{18}$ alkyl heteroaryl, $C_1$-$C_{18}$ carbonyl, $C_1$-$C_{18}$ carbonylamino, $C_1$-$C_{18}$ sulfonyl, $C_1$-$C_{18}$ sulfonylamino, or $C_1$-$C_{18}$ carboxyl; and wherein Z is a bond, $C_1$-$C_4$ alkyl, heteroalkyl, or an O atom.

12. A compound according to claim 11, wherein B is $C_1$-$C_2$ alkyl aryl, $C_2$-carbonyl, $C_2$-carbonyl amino, $C_2$-carboxyl, or $C_2$-hydroxyl aryl.

13. A compound according to Formula V:

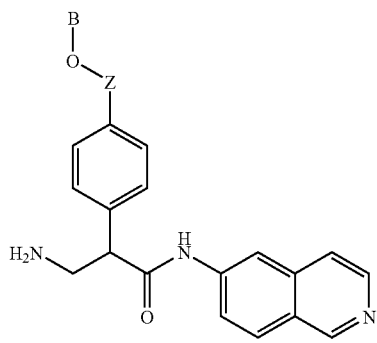

(V)

wherein Z is a bond or —CH$_2$—; and
B is an aryl group, a heteroaryl group, a cycloalkyl group, a heterocycloalkyl group, C$_1$-C$_{22}$ alkyl, C$_1$-C$_{22}$ alkyl aryl, C$_1$-C$_{22}$ alkyl heteroaryl, C$_2$-C$_{22}$ alkenyl, C$_2$-C$_{22}$ alkynyl, C$_1$-C$_{22}$ carbonyl, C$_1$-C$_{22}$ carbonylamino, C$_1$-C$_{22}$ alkoxy, C$_1$-C$_{22}$ sulfonyl, C$_1$-C$_{22}$ sulfonylamino, C$_1$-C$_{22}$ thioalkyl, or C$_1$-C$_{22}$ carboxyl.

14. A compound selected from the group consisting of:

E482

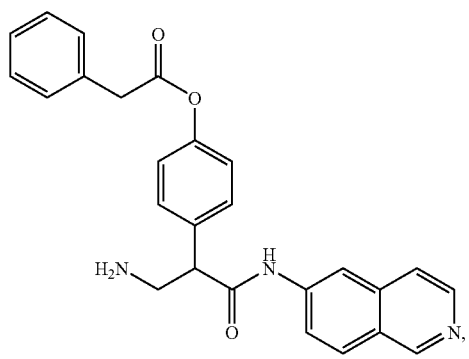

4-(3-amino-1-(isoquinolin-6-ylamino)-1-oxopropan-2-yl)phenyl 2-phenylacetate

E483

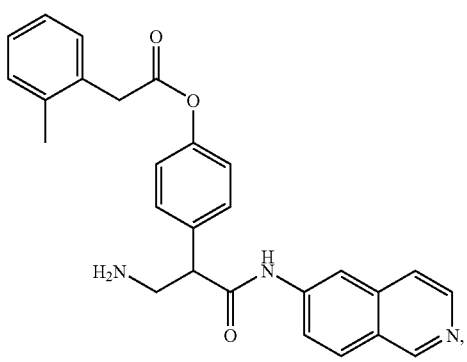

4-(3-amino-1-(isoquinolin-6-ylamino)-1-oxopropan-2-yl)phenyl 2-o-tolylacetate

E484

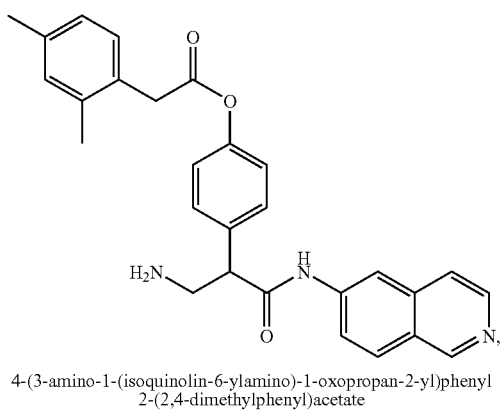

4-(3-amino-1-(isoquinolin-6-ylamino)-1-oxopropan-2-yl)phenyl 2-(2,4-dimethylphenyl)acetate

E485

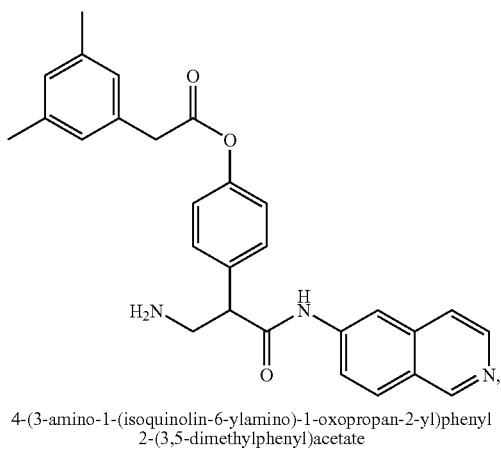

4-(3-amino-1-(isoquinolin-6-ylamino)-1-oxopropan-2-yl)phenyl 2-(3,5-dimethylphenyl)acetate

E486

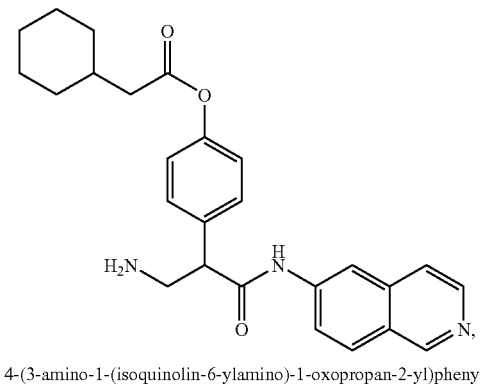

4-(3-amino-1-(isoquinolin-6-ylamino)-1-oxopropan-2-yl)phenyl 2-cyclohexylacetate

E487

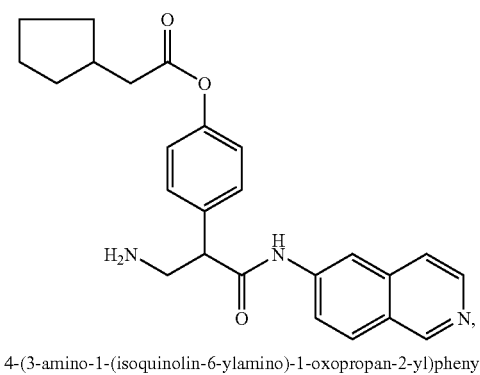

4-(3-amino-1-(isoquinolin-6-ylamino)-1-oxopropan-2-yl)phenyl 2-cyclopentylacetate -continued

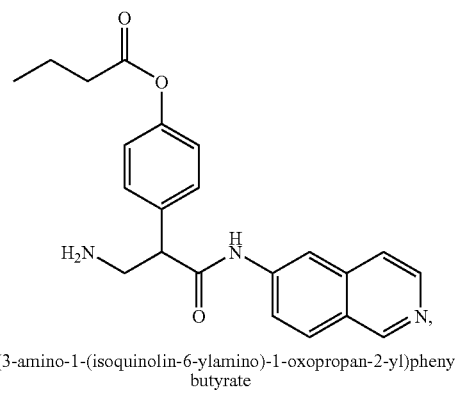

4-(3-amino-1-(isoquinolin-6-ylamino)-1-oxopropan-2-yl)phenyl butyrate

E488

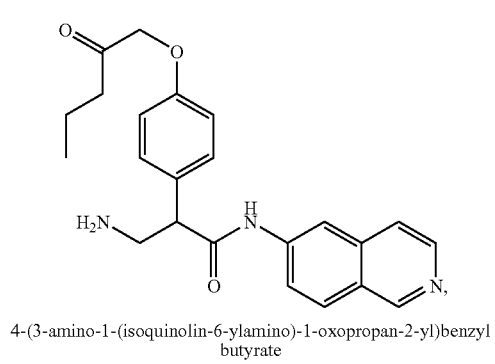

4-(3-amino-1-(isoquinolin-6-ylamino)-1-oxopropan-2-yl)benzyl butyrate

E489

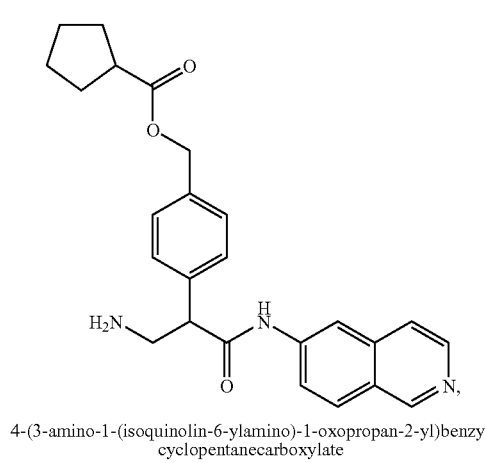

4-(3-amino-1-(isoquinolin-6-ylamino)-1-oxopropan-2-yl)benzyl cyclopentanecarboxylate

E490

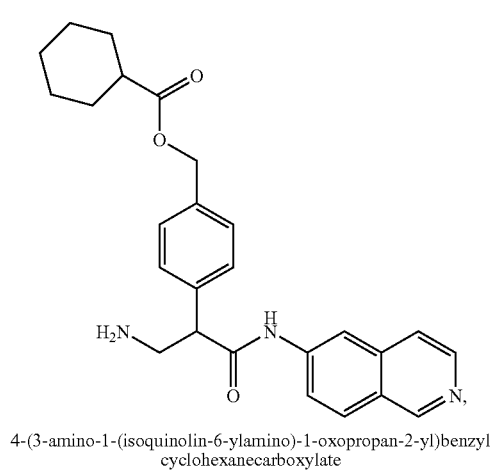

4-(3-amino-1-(isoquinolin-6-ylamino)-1-oxopropan-2-yl)benzyl cyclohexanecarboxylate

E491

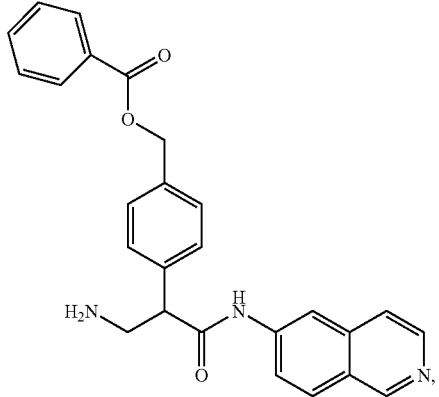

4-(3-amino-1-(isoquinolin-6-ylamino)-1-oxopropan-2-yl)benzyl benzoate

E492

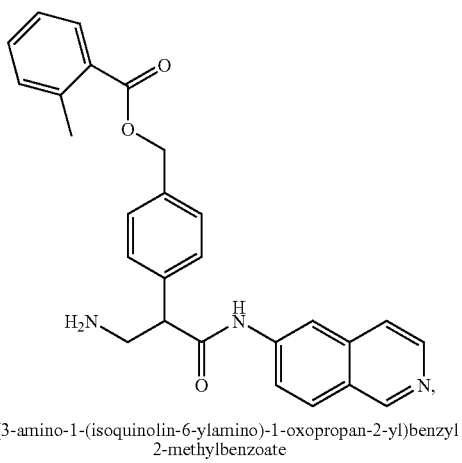

4-(3-amino-1-(isoquinolin-6-ylamino)-1-oxopropan-2-yl)benzyl 2-methylbenzoate

E493

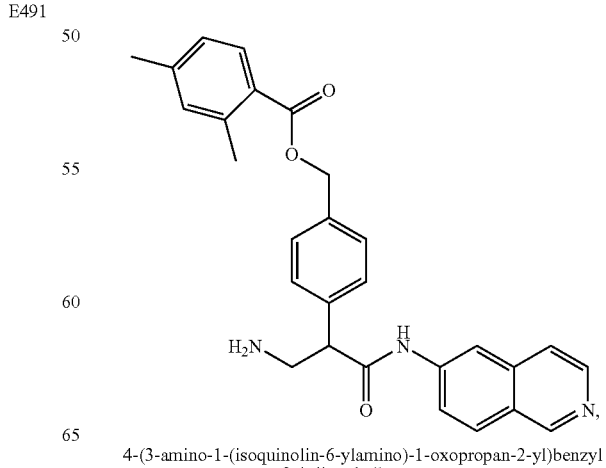

4-(3-amino-1-(isoquinolin-6-ylamino)-1-oxopropan-2-yl)benzyl 2,4-dimethylbenzoate

E494

E495

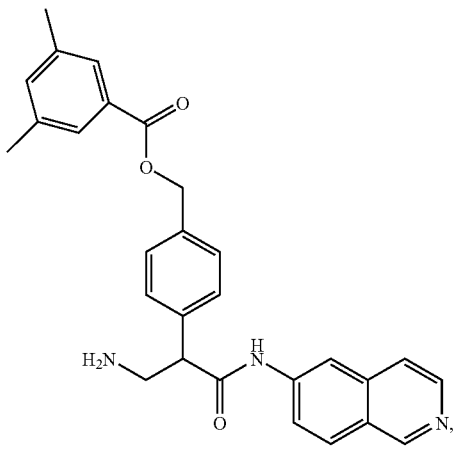

4-(3-amino-1-(isoquinolin-6-ylamino)-1-oxopropan-2-yl)benzyl 3,5-dimethylbenzoate

E496

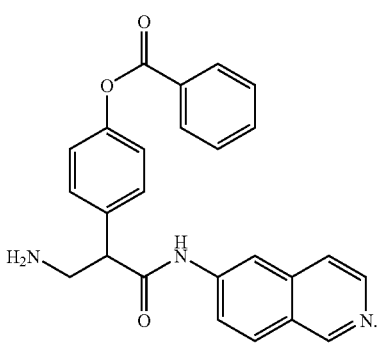

4-(3-amino-1-(isoquinolin-6-ylamino)-1-oxopropan-2-yl)benzyl 4-methylbenzoate

E497

15. A compound according to Formula (VI):

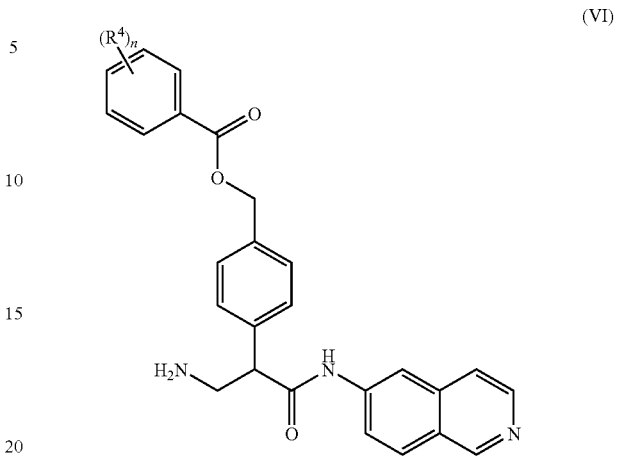

(VI)

wherein $R^4$ is methyl and n is 2.

16. 4-(3-Amino-1-(isoquinolino-6-ylamino)-1-oxopropan-2-yl)benzyl 2,4-dimethylbenzoate.

17. A pharmaceutical composition comprising a compound according to claim 1 and a pharmaceutically acceptable carrier.

18. A method for treating a disease in a subject comprising: administering to a subject an effective amount of a compound according to claim 1; wherein the disease comprises eye disease.

19. The method of claim 18, wherein the eye disease comprises glaucoma or a neurodegenerative eye disease.

20. A method of modulating kinase activity comprising: contacting a cell with a compound according to claim 1 in an amount effective to modulate kinase activity.

21. The method of claim 20, wherein the cell is in a subject.

22. A method of reducing intraocular pressure comprising: contacting a cell with a compound according to claim 1 in an amount effective to reduce intraocular pressure.

23. The method of claim 22, wherein the cell is in a subject.

24. The compound according to claim 1, wherein $R_1$, $R_2$, and $R_3$ are each hydrogen; A is $CH_2$; Z is bond; $X_1$, $X_2$, and $X_3$ are each hydrogen; and

is phenyl.

25. The compound of claim 24, wherein B is methyl.

26. The compound of claim 24, wherein B is $C_1$-$C_4$ carbonyl.

27. The compound of claim 26, wherein B is —C(O)-phenyl, —C(O)-dimethylphenyl, —C(O)—CH$_2$-phenyl, —C(O)-cyclohexyl, or —C(O)-methylphenyl.

28. The compound according to claim 10, wherein $R_1$, $R_2$, and $R_3$ are each hydrogen; Z is bond; and $X_1$, $X_2$, and $X_3$ are each hydrogen.

29. The compound of claim 28, wherein B is $C_1$-$C_4$ carbonyl.

30. The compound of claim 29, wherein B is —C(O)-cyclopenyl, —C(O)-cyclohexyl, —C(O)-dimethylphenyl, —C(O)-buytl, —C(O)-phenyl, —C(O)-methoxyphenyl, —C(O)-adamantyl, —C(O)-propyl, or —C(O)—CH$_2$-phenyl.

31. The compound according to claim 10, wherein $R_1$ is $CH_3$; $R_2$ and $R_3$ are each hydrogen; Z is bond; $X_1$, $X_2$, and $X_3$ are each hydrogen; and B is $C_1$-$C_4$ carbonyl.
32. The compound according to claim 1, wherein the compound is selected from the following:
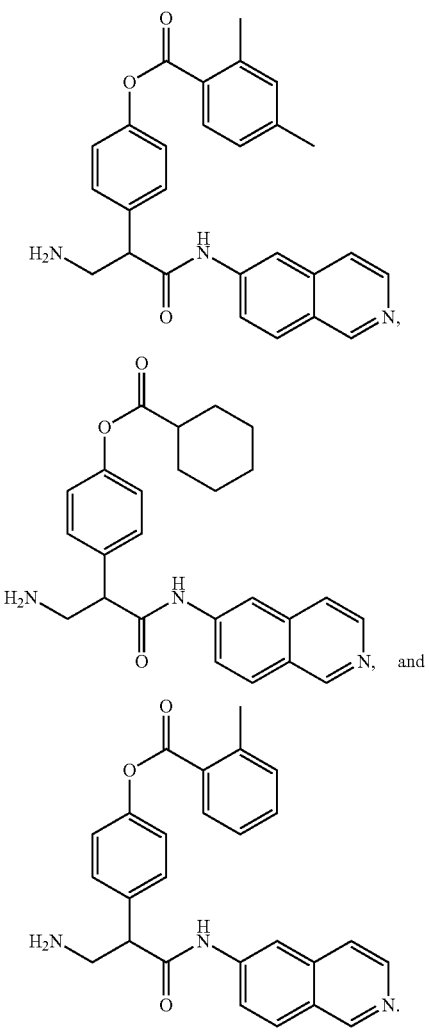
33. The compound according to claim 10, wherein the compound is selected from the following:
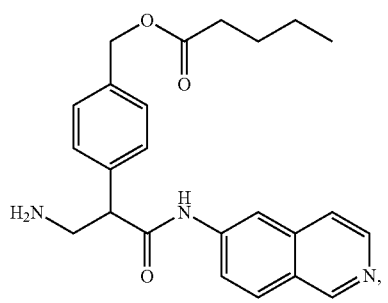
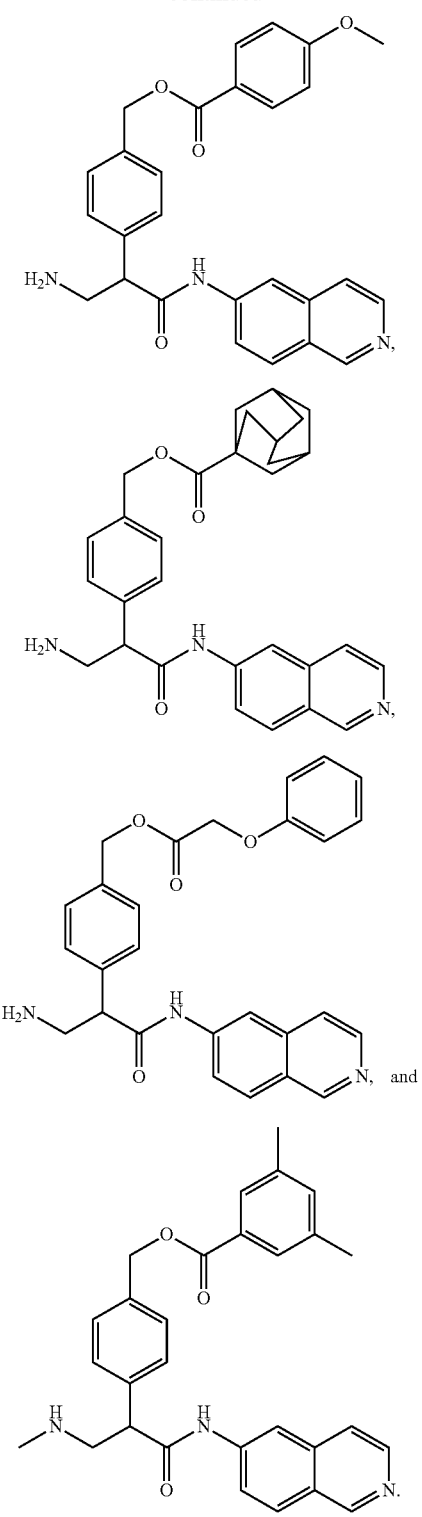
* * * * *